United States Patent
Bonnafous et al.

(10) Patent No.: US 9,944,712 B2
(45) Date of Patent: Apr. 17, 2018

(54) TLR3 BINDING AGENTS

(71) Applicant: INNATE PHARMA, Marseille (FR)

(72) Inventors: Cécile Bonnafous, Marseille (FR);
Laurent Gauthier, Marseille (FR);
Yannis Morel, Marseille (FR); Carine Paturel, Marcy l'Etoile (FR); Ivan Perrot, Cassis (FR)

(73) Assignee: Innate Pharma, Marseille (FR)

( * ) Notice: Subject to any disclaimer, the term of this patent is extended or adjusted under 35 U.S.C. 154(b) by 361 days.

(21) Appl. No.: 14/403,171

(22) PCT Filed: May 30, 2013

(86) PCT No.: PCT/EP2013/061173
§ 371 (c)(1),
(2) Date: Nov. 21, 2014

(87) PCT Pub. No.: WO2013/178736
PCT Pub. Date: Dec. 5, 2013

(65) Prior Publication Data
US 2015/0140000 A1 May 21, 2015

Related U.S. Application Data

(60) Provisional application No. 61/653,652, filed on May 31, 2012, provisional application No. 61/670,289, filed on Jul. 11, 2012, provisional application No. 61/679,923, filed on Aug. 6, 2012.

(51) Int. Cl.
*A61K 39/395* (2006.01)
*C07K 16/28* (2006.01)
*A61K 47/68* (2017.01)
*C07K 14/705* (2006.01)
*A61K 39/00* (2006.01)

(52) U.S. Cl.
CPC ...... *C07K 16/2896* (2013.01); *A61K 39/3955* (2013.01); *A61K 47/6849* (2017.08); *A61K 2039/505* (2013.01); *C07K 16/2803* (2013.01); *C07K 2317/34* (2013.01); *C07K 2317/565* (2013.01); *C07K 2317/76* (2013.01); *C07K 2317/77* (2013.01); *C07K 2317/92* (2013.01)

(58) Field of Classification Search
CPC .......... A61K 2039/505; A61K 39/3955; A61K 39/39558; C07K 16/18; C07K 16/28; C07K 2317/51; C07K 2317/515; C07K 2317/56; C07K 16/2896; C07K 2317/565; C07K 16/2866
See application file for complete search history.

(56) References Cited

U.S. PATENT DOCUMENTS

| | | |
|---|---|---|
| 3,773,919 A | 11/1973 | Boswell et al. |
| 4,816,567 A | 3/1989 | Cabilly et al. |
| 5,229,275 A | 7/1993 | Goroff |
| 5,491,084 A | 2/1996 | Chalfie et al. |
| 5,567,610 A | 10/1996 | Borrebaeck et al. |
| 5,660,827 A | 8/1997 | Thorpe et al. |
| 6,162,963 A | 12/2000 | Kucherlapati et al. |
| 6,267,958 B1 | 7/2001 | Andya et al. |
| 6,486,382 B1 | 11/2002 | Gordan-Kamm et al. |
| 8,076,460 B2 | 12/2011 | Matsumoto et al. |
| 8,221,755 B2 | 7/2012 | Dunlop et al. |
| 8,222,375 B2 | 7/2012 | Terrett et al. |
| 8,354,508 B2 | 1/2013 | Diedrich et al. |
| 8,409,567 B2 | 4/2013 | Cunningham et al. |
| 8,460,659 B2 | 6/2013 | Cunningham et al. |
| 8,540,986 B2 | 9/2013 | Cunningham et al. |
| 8,586,041 B2 | 11/2013 | van de Winkel et al. |
| 8,802,103 B2 | 8/2014 | Gurney et al. |
| 8,828,400 B2 | 9/2014 | Leuchs et al. |
| 9,238,693 B2 | 1/2016 | Cunningham et al. |
| 9,255,153 B2 | 2/2016 | Cunningham et al. |
| 9,388,246 B2 | 7/2016 | Gauthier et al. |
| 9,481,731 B2 | 11/2016 | Cunningham et al. |
| 9,522,957 B2 | 12/2016 | Cunningham et al. |
| 2002/0136719 A1 | 9/2002 | Shenoy et al. |
| 2005/0123536 A1 | 6/2005 | Law et al. |
| 2005/0180972 A1 | 8/2005 | Wahl et al. |
| 2009/0105460 A1 | 4/2009 | Matsumoto et al. |
| 2010/0166778 A1 | 7/2010 | Cunningham et al. |
| 2011/0008352 A1 | 1/2011 | Cunningham et al. |
| 2012/0034232 A1 | 2/2012 | Gauthier et al. |
| 2012/0064095 A1 | 3/2012 | Cunningham et al. |
| 2013/0090457 A1 | 4/2013 | Cunningham et al. |

(Continued)

FOREIGN PATENT DOCUMENTS

| | | |
|---|---|---|
| WO | WO 1998/50547 A2 | 11/1998 |
| WO | WO 1998/56418 | 12/1998 |

(Continued)

OTHER PUBLICATIONS

Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*

(Continued)

*Primary Examiner* — Bridget E Bunner
(74) *Attorney, Agent, or Firm* — Knobbe Martens Olson & Bear LLP

(57) ABSTRACT

Disclosed herein are anti-TLR3 antibodies as well as methods of making and using them. The antibodies are particularly adapted to the treatment of autoimmune or inflammatory diseases using anti-TLR3 antibodies.

28 Claims, 12 Drawing Sheets

(56) References Cited

U.S. PATENT DOCUMENTS

| | | |
|---|---|---|
| 2013/0244281 A1 | 9/2013 | Cunningham et al. |
| 2013/0280263 A1 | 10/2013 | Cunningham et al. |
| 2014/0017250 A1 | 1/2014 | Cunningham et al. |
| 2014/0065154 A1 | 3/2014 | Gauthier et al. |
| 2014/0093508 A1 | 4/2014 | Cunningham et al. |
| 2014/0212426 A1 | 7/2014 | Cunningham et al. |
| 2016/0347853 A1 | 12/2016 | Gauthier et al. |
| 2017/0058041 A1 | 3/2017 | Cunningham et al. |

FOREIGN PATENT DOCUMENTS

| | | |
|---|---|---|
| WO | WO 2003/106499 A1 | 12/2003 |
| WO | WO 2006/060513 A2 | 6/2006 |
| WO | WO 2007/051164 A2 | 5/2007 |
| WO | WO 2008/049897 | 5/2008 |
| WO | WO 2009/130616 | 10/2009 |
| WO | WO 2010/051470 A2 | 5/2010 |
| WO | WO 2010/127113 A2 | 11/2010 |
| WO | WO 2011/004028 | 1/2011 |
| WO | WO 2012/095432 A2 | 7/2012 |
| WO | WO 2013/178736 | 12/2013 |
| WO | WO 2014/052188 | 4/2014 |

OTHER PUBLICATIONS

Ngo et al. Computational complexity, protein structure prediction, and the Levinthal paradox. The Protein Folding Problem and Tertiary Structure Prediction, pp. 492-495, 1994.*
Burks et al. (PNAS 94:412-417 (1997)).*
Jang et al. (Molec. Immunol. 35:1207-1217 (1998)).*
Nomi et al. Toll-like receptor 3 signaling induces apoptosis in human head and neck cancer via survivin associated pathway. Oncol Reports 24: 225-231, 2009.*
Saloun et al. TLR3 can directly trigger apoptosis in human cancer cells. J Immunol 176: 4894-4901, 2006.*
Glavan et al. The exploitation of Toll-like receptor 3 signaling in cancer therapy. Curr Pharm Des 20(42):6555-6564, 2014.*
Tannock and Hill. The Basic Science of Oncology. 1998. New York: McGraw-Hill, pp. 357-358.*
U.S. Notice of Allowance dated May 6, 2016 in U.S. Appl. No. 13/102,019, filed May 5, 2011.
U.S. Office Action dated Jun. 16, 2016 in U.S. Appl. No. 13/979,370, filed Nov. 19, 2013.
U.S. Response dated May 25, 2016 in U.S. Appl. No. 13/751,718, filed Jan. 28, 2013.
U.S. Notice of Allowance dated Aug. 2, 2016 in U.S. Appl. No. 13/751,718, filed Jan. 28, 2013.
U.S. Response/RCE dated Apr. 5, 2016 in U.S. Appl. No. 13/973,187, filed Aug. 22, 2013.
U.S. Notice of Allowance dated Apr. 18, 2016 in U.S. Appl. No. 13/973,187, filed Aug. 22, 2013.
U.S. Response/RCE/IDS dated Jul. 18, 2016 in U.S. Appl. No. 13/973,187, filed Aug. 22, 2013.
U.S. 2nd Notice of Allowance dated Aug. 10, 2016 in U.S. Appl. No. 13/973,187, filed Aug. 22, 2013.
Housset et al., "The three-dimensional structure of a T-cell antigen receptor ValphaVbeta heterodimer reveals a novel arrangement of the Vbeta domain", EMBO J., (1997) 16(14):4205-4216.
Schuermann et al., "Structure of an anti-DNA Fab Complexed with a Non-DNA Ligand Provides Insights into Cross-Reactivity and Molecular Mimicry", Proteins: Structure, Function, and Bioinformatics (2004) 57:269-278.
U.S. Office Action dated Oct. 20, 2015 in U.S. Appl. No. 13/102,019, filed May 5, 2011.
U.S. Response dated Jan. 20, 2016 in U.S. Appl. No. 13/102,019, filed May 5, 2011.
U.S. Office Action dated Dec. 17, 2015 in U.S. Appl. No. 13/979,370, filed Nov. 19, 2013.
U.S. Response dated Mar. 15, 2016 in U.S. Appl. No. 13/979,370, filed Nov. 19, 2013.
U.S. Office Action dated Jan. 25, 2016 in U.S. Appl. No. 13/751,718, filed Jan. 28, 2013.
U.S. 3nd Notice of Allowance dated Aug. 27, 2015 in U.S. Appl. No. 13/777,513, filed Feb. 26, 2013.
U.S. 3rd Notice of Allowance dated Sep. 14, 2015 in U.S. Appl. No. 13/798,494, filed Mar. 13, 2013.
U.S. Notice of Allowance dated Jan. 6, 2016 in U.S. Appl. No. 13/973,187, filed Aug. 22, 2013.
Mayo Clinic, "Diseases and Conditions: Ischemic Colitis", Oct. 10, 2012 downloaded from http://www.mayoclinic.org/diseases-conditions/ischemic-colitis/basics/causes/con-20026677?p=1; 6 pages.
National Institute of Health, "Asthma", downloaded Jan. 20, 2012 from www.nhlbi.nih.gov/health/health-topics/topics/asthma/; 2 pages.
National Institute of Health, "Graft Versus Host Disease (GVHD): A Guide for Patients and Families after Stem Cell Transplant", 2007; 3 pages.
U.S. Office Action dated Jun. 9, 2015 in U.S. Appl. No. 13/979,370, filed Nov. 19, 2013.
U.S. Response dated Aug. 10, 2015 in U.S. Appl. No. 13/979,370, filed Nov. 19, 2013.
U.S. Response dated May 20, 2015 in U.S. Appl. No. 13/751,718, filed Jan. 28, 2013.
U.S. Office Action dated Jun. 2, 2015 in U.S. Appl. No. 13/751,718, filed Jan. 28, 2013.
U.S. Response dated Oct. 1, 2015 in U.S. Appl. No. 13/751,718, filed Jan. 28, 2013.
U.S. Office Action dated May 27, 2015 in U.S. Appl. No. 13/973,187, filed Aug. 22, 2013.
U.S. Response dated Sep. 25, 2015 in U.S. Appl. No. 13/973,187, filed Aug. 22, 2013.
"Submission Regarding Experimental Results", May 19, 2015, 5 pages; filed in U.S. Appl. No. 13/102,019 on May 20, 2015.
"Submission Regarding Experimental Results", Jun. 8, 2015, 5 pages; filed in U.S. Appl. No. 13/979,370 on Jun. 8, 2015.
"Submission Regarding Experimental Results", Jun. 8, 2015, 5 pages; filed in U.S. Appl. No. 14/403,171 on Jun. 8, 2015.
Datasheet MCA2267; AbD Serotec, from Table A of Submission Regarding Experimental Results, "Mouse Anti Human CD283", commercially available prior to Sep. 2008, printed Apr. 23, 2015; 3 pages.
Datasheet N-14; Santa Cruz Biotechnology, Inc from Table A of Submission Regarding Experimental Results, "TLR3 (N-14): sc-8691", commercially available prior to Sep. 2008, archived Aug. 2010; 1 page.
Datasheet Q-18; Santa Cruz Biotechnology, Inc. from Table A of Submission Regarding Experimental Results, TLR3 (Q-18): sc-12509, commercially available prior to Sep. 2008, archived Aug. 2010; 1 page.
Datasheet; R&D Systems, from Table A of Submission Regarding Experimental Results, "Polyclonal Goat IgG—Mouse TLR3 Antibody", Rev. Mar. 13, 2015, commercially available prior to Sep. 2008, Catalog #AF3005; 1 page.
Datasheet TLR3-7; Affymetrix eBioscience, from Table A of Submission Regarding Experimental Results, "Anti-Human CD283 (TLR3) Purified", TLR3-7, Catalog #14-9039, commercially available prior to Sep. 2008; 2 pages.
Datasheet 40C1285; Imgenex, from Table A of Submission Regarding Experimental Results, "TLR3 Antibody-NBP2-24875", commercially available prior to Sep. 2008, Updated Mar. 1, 2015; 5 pages.
Datasheet 619F7.06; Dendritics, from Table A of Submission Regarding Experimental Results, Munoclonal Anti-human, rat, mouse, dog, TLR3/CD283, Date of Commercial Availability unknown; 1 page.
Datasheet A01; ABNOVA, from Table A of Submission Regarding Experimental Results, TLR3 polyclonal antibody, commercially available prior to Sep. 2008, 1 page.
Datasheet L-13; Santa Cruz Biotechnology, Inc. from Table A of Submission Regarding Experimental Results, TLR3 (L-13): sc-16238, commercially available prior to Sep. 2008, 1 page.

(56) References Cited

OTHER PUBLICATIONS

Datasheet C-20; Santa Cruz Biotechnology, Inc. from Table A of Submission Regarding Experimental Results, TLR3 (C-20): se-8692, commercially available prior to Sep. 2008, 1 page.
Datasheet H-125; Santa Cruz Biotechnology, Inc. from Table A of Submission Regarding Experimental Results, TLR3 (H-125): sc-10740, commercially available prior to Sep. 2008, 1 page.
Kimura et al., "Toll-like receptor 3 stimulation causes corticosteroid-refractory airway neutrophilia and hyperresponsiveness in mice", Chest (Jul. 2013) 144(1): 99-105.
Kizawa et al., "Possible involvement of TLR3 pathway on corticosteroid refractory airway inflammation in mice", 83rd Annual Meeting of the Japanese-Pharmacological-Society, Mar. 1, 2010, p. 205P.
Morel, Y., "Blocking Anti-TLR3 mAb for Inflammation—Molecular Pattern Recognition Receptors", Apr. 11-12, 2013; online at URL:http://innate-pharma.com/sites/default/files/iph33_mprr_conference_2013_0.pdf; 30 pages.
Rossios et al., "TLR3 Activation Causes Corticosteroid Insensitivity in Human Bronchial Epithelial Cells", American Thoracic Society Inter'l Conference. May 9, 2013; Meeting Abstract #2394, Online at URL:http://atsjournals.org/doi/abs/10.1164/ajrccm-conference.2013.187.1_MeetingAbstracts.A2394.
Chinese Office Action dated Jul. 2, 2013 for Application No. 201080030919.5.
International Search Report dated Aug. 7, 2014 for PCT/EP2014/059773, filed May 13, 2014.
U.S. Office Action dated Feb. 20, 2015 in U.S. Appl. No. 13/102,019, filed May 5, 2011.
U.S. Response dated May 20, 2015 in U.S. Appl. No. 13/102,019, filed May 5, 2011.
U.S. Office Action dated Feb. 20, 2015 in U.S. Appl. No. 13/751,718, filed Jan. 28, 2013.
U.S. 2nd Notice of Allowance dated Apr. 27, 2015 in U.S. Appl. No. 13/777,513, filed Feb. 26, 2013.
U.S. Notice of Allowance dated Mar. 11, 2015 in U.S. Appl. No. 13/798,494, filed Mar. 13, 2013.
U.S. 2nd Notice of Allowance dated Apr. 23, 2015 in U.S. Appl. No. 13/798,494, filed Mar. 13, 2013.
U.S. Office Action dated Jan. 29, 2015 in U.S. Appl. No. 13/973,187, filed Aug. 22, 2013.
U.S. Response dated Mar. 30, 2015 in U.S. Appl. No. 13/973,187, filed Aug. 22, 2013.
Akira et al., "Toll-like receptor signalling", Nat Rev Immunol. (2004) 4:499-511.
Alamanos et al., "Epidemiology of adult rheumatoid arthritis", Autoimmun Rev. (2005) 4(3):130-136.
Albert, Matthew L., "Death-defying immunity: do apoptotic cells influence antigen processing and presentation?", Nat. Rev. Immunol. (2004) 4:223-231.
Alexoupoulou et al., "Recognition of double-stranded RNA and activation of NK-κB by Toll-like receptor 3". Nature (2001) 413: 732-738.
Altschul et al., "Basic Local Alignment Search Tool", J Mol Biol. (1990) 215:403-410.
Amersham Biosciences, Antibody Purification Handbook, (2002) Publication No. 18-1037-46, Edition AC, 112 pages.
Andersen et al., "Structural characterization of both the non-proteolytic and proteolytic activation pathways of coagulation Factor XIII studied by hydrogen-deuterium exchange mass spectrometry"; Int J Mass Spectro. (2010 online) 302(1-3):139-148.
Angal et al., "A single amino acid substitution abolishes the heterogeneity of chimeric mouse/human (IgG4) antibody" Mol Immunol. (1993) 30(1):105-108.
Avis et al., Pharmaceutical Dosage Forms: Parenteral Medications, Dekker, New York, (1993), vol. 1, 2, and 3, TOC, 14 pages.
Barnes, Peter J. "The Cytokine Network in Chronic Obstructive Pulmonary Disease", Am J Respir Cell Mol Biol. (2009) 41: 631-638.

Bell et al., "The dsRNA binding site of human Toll-like receptor 3", Proc. Natl. Acad. Sci. USA, (2006) 103(23):8792-8797.
Bokarewa et al., "Arthritogenic dsRNA is present in synovial fluid from rheumatoid arthritis patients with an erosive disease course", Eur J Immunol. (2008) 38:3237-3244.
Botos et al., "The Toll-like receptor 3:dsRNA signaling complex", Bio Biophys Acta (2009) 1789(9-10):667-674.
Brorson et al., "Mutational Analysis of Avidity and Fine Specificity of Anti-Levan Antibodies", J Immunol. (1999) 163:6694-6701.
Brummell et al., "Probing the combining site of an anti-carbohydrate antibody by saturation-mutagenesis: Role of the heavy-chain CDR3 residues", Biochem. (1993) 32(4):1180-1187.
Bukhari et al., "Rheumatoid factor is the major predictor of increasing severity of radiographic erosions in rheumatoid arthritis", Arth Rheum. (2002) 46(4): 906-912.
Bunting et al., "Novel antagonist antibody to TLR3 blocks poly(I:C)-induced inflammation in vivo and in vitro", Cellular. Immunol. (2011) 267(1):9-16.
Carillo et al., "The Multiple Sequence Alignment Problem in Biology", Siam J. Appl Math. (1988) 48(5):1073-1082.
Carter et al., "Antibody-Drug Conjugates for Cancer Therapy", Cancer J. (2008) 14:154-169.
Carter et al., "Humanization of an anti-p185$^{HER2}$ antibody for human cancer therapy", Proc Natl Acad Sci. USA (1992) 89:4285-4289.
Cavassani et al., "TLR3 is an endogenous sensor of tissue necrosis during acute inflammatory events", J Exp Med. (2008) 205:2609-2621.
Chari, Ravi V.J., "Targeted Cancer Therapy: Conferring Specificity to Cytotoxic Drugs", Accts Chem Res. (2008) 41(1): 98-107.
Choe et al., "Crystal structure of human Toll-like receptor 3 (TLR3) ectodomain", Science (2005) 309(5734):581-585.
Chothia et al., "Canonical Structures for the Hypervariable Regions of Immunoglobulins", J Mol Biol. (1987) 196:901-917.
Clackson et al., "A Hot Spot of Binding Energy in a Hormone-Receptor Interface", Science (1995) 267:383-386.
Coligan et al., Eds., Current Protocols in Immunology, Greene Publishing Assoc. (1991) TOC. 12 pages.
Colman, P.M., "Effects of amino acid sequence changes on antibody-antigen interactions", Res Immunol. (1994) 145:33-36.
De Bouteiller et al., "Recognition of double-stranded RNA by human toll-like receptor 3 and downstream receptor signaling requires multimerization and an acidic Ph", J Biol Chem. (2005) 280(46):38133-38145.
Delgado et al., "Enhanced tumour specificity of an anti-carcinoembrionic antigen Fab' fragment by poly(ethylene glycol) (PEG) modification", Br J Cancer. (1996) 73(2):175-182.
Devereux et al., "A comprehensive set of sequence analysis programs for the VAX", Nucl Acids Res. (1984) 12(1):387-395.
Doronina et al., "Development of potent monoclonal antibody Auristatin conjugates for cancer therapy", Nat Biotech. (2003) 21(7):778-784 & Erratum Nat Biotech. (2003) 21(8):941.
Downard, Kevin M., "Contributions of mass spectrometry to structural immunology", J. Mass Spectrom. (2000) 35(4):493-503.
Duffy et al., "Down modulation of human TLR3 function by a monoclonal antibody," Cell Immunol., (2007) 248(2):103-114.
Ehring, Hanno, "Hydrogen Exchange/Electrospray Ionization Mass Spectrometry Studies of Structural Features of Proteins and Protein/Protein Interactions", Anal Biochem. (1999) 267(2):252-259.
Engen et al., "Investigating protein structure and dynamics by hydrogen exchange MS", Anal Chem. (2001) 73(9):256A-265A.
Fägerstam et al., "Detection of Antigen-Antibody Interactions by Surface Plasmon Resonance", J Mol Recogn. (1990) 3(5/6):208-214.
Francisco et al., "cAC10-vaMMAE, an anti-CD30-monomethyl auristatin E conjugate with potent and selective antitumor activity", Neoplasia, (2003) 102(4):1458-1465.
Gabriel, Sherine E., "The epidemiology of rheumatoid arthritis." Rheum. Dis. Clin North Am. (2001) 27(2):269-281.
Gennaro, ed., Remington's Pharmaceutical Sciences, 18th ed., Mack Publishing Co., Easton, PA; (1990) Cover and Table of Contents; pp. 5.

(56) References Cited

OTHER PUBLICATIONS

Coding, James W., "Monoclonal Antibodies: Principles and Practice," Academic Press, (1986) 2nd Edition, Chapter 3, pp. 59-103.
Goodman & Gilman's, The Pharmacological Bases of Therapeutics, 8th ed., Pergamon Press; (1990) Cover and Table of Contents; pp. 8.
Green et al., "Antigen-specific human monoclonal antibodies from mice engineered with human Ig heavy and light chain YACs", Nature Gen. (1994) 7:13-21.
Gribskov et al., (Eds.) Sequence Analysis Primer; Stockton Press (1991); Table of Contents, 7 pages.
Griffin et al., (Eds.) Methods in Molecular Biology-24: Computer Analysis of Sequence Data; Part I & II; Humana Press, New Jersey (1994) TOC, 8 pages.
Guex et al., "Swiss-Model and the Swiss-Pdb Viewer: An environment for comparative protein modeling", Electrophoresis (1997) 18:2714-2723.
Häcker et al., "Cell type-specific activation of mitogen-activated protein kinases by CpG-DNA controls interleukin-12 release from antigen-presenting cells", EMBO J. (1999) 18(24):6973-6982.
Hamblett et al., "Effects of Drug Loading on the Antitumor Activity of a Monoclonal Antibody Drug Conjugate", Clin Cancer Res. (2004) 10:7063-7070.
Harlow et al., (Eds.), Antibodies—A Laboratory Manual; Table of Contents, Cold Spring Harbor Laboratory Press, Cold Spring Harbor, NY (1988) TOC; 9 pages.
Heliövaara et al., "Rheumatoid factor, chronic arthritis and mortality", Ann. Rheum. Dis. (1995) 54: 811-814.
Huang et al., "NMR Identification of Epitopes of Lyme Disease Antigen OspA to Monoclonal Antibodies", J Mol Biol. (1998) 281:61-67.
Hulsmans et al., "The Course of Radiologic Damage During the First Six Years of Rheumatoid Arthritis", Arthritis Rheum. (2000) 43(9): 1927-1940.
Jakobovits et al., "Germ-line transmission and expression of a human-derived yeast artificial chromosome", Nature (1993) 362:255-258.
Jones et al., "Replacing the complementarity-determining regions in a human antibody with those from a mouse", Nature (1986) 321:522-525.
Kabat et al., (Eds.) Sequences of Proteins of Immunological Interest, 5th Edition; (1991) Table of Contents; 11 pages.
Karikó et al., "mRNA is an endogenous ligand for toll-like receptor 3", J Biol Chem. (2004) 279(13):12542-12550.
Keystone, E.C., "B cells in rheumatoid arthritis: from hypothesis to the clinic", Rheumatology (2005) 44 (Suppl. 2): ii8-ii12.
Kim et al., "TLR-3 enhances osteoclastogenesis through upregulation of RANKL expression from fibroblast-like synoviocytes in patients with rheumatoid arthritis", Immunol. Lett. (2009) 124:9-17.
Kiselar et al., "Direct Identification of Protein Epitopes by Mass Spectrometry without immobilization of Antibody and Isoltion of Antibody-peptide complexes", Anal Chem. (1999) 71(9):1792-1801.
Kobayashi et al., "Tryptophan H33 plays an important role in pyrimidine (6-4) pyrimidone photoproduct binding by a high-affinity antibody", Prot Engin. (1999) 12(10): 879-884.
Kröger et al., Epitope-mapping of transglutaminase with parallel label-free optical detection, Biosen Bioelectr. (2002) 17:937-944.
Lang et al., "Immunoprivileged status of the liver is controlled by Toll-like receptor 3 signaling", J Clin Invest. (2006) 116:2456-2463.
Law et al., "Efficient Elimination of B-Lineage Lymphomas by Anti-CD20-Auristatin Conjugates", Clin Canc Res. (2004) 10:7842-7851.
Leipert et al., "Investigation of the Molecular Recognition of Amino Acids by Cyclopeptides with Reflectometric Interference Spectroscopy", Angew. Chem. Int. Ed. (1998) 37:3308-3311.
Leong et al., "Adapting pharmacokinetic properties of a humanized anti-interleukin-8 antibody for therapeutic applications using site-specific pegylation", Cytokine (2001) 16:106-119.
Lesk, Arthur M. (Ed.) Computational Molecular Biology, Oxford University Press (1988); Table of Contents; 4 pages.
Lieberman et al. [Eds], Pharmaceutical Dosage Forms: Disperse Systems, vol. 1 and 2, Dekker, New York (1990) TOC, 12 pages.
Lonberg et al., "Antigen-specific human antibodies from mice comprising four distinct genetic modifications", Nature (1994) 368:856-859.
Luo et al., "Lateral Clustering of TLR3:dsRNA Signaling Units Revealed by TLR3ecd:3Fabs Quaternary Structure", J Mol Biol. (2012) 421(1): 112-124.
Luo et al., Supplementary information to Lateral Clustering of TLR3:dsRNA Signaling Units Revealed by TLR3ecd:3Fabs structure (2012), 6 pages.
Manca, F., "Interference of Monoclonal Antibodies with Proteolysis of Antigens in Cellular and in Acellular Systems", Ann 1st Super Sanita. (1991): 27(1):15-19.
Matsumoto et al., "Subcellular Localization of Toll-like Receptor 3 in Human Dendritic Cells", J Immunol. (2003) 171:3154-3162.
McCafferty et al., "Phage antibodies: Filamentous phage displaying antibody variable domains", Nature (1990) 348:552-554.
McDonald et al., "Recommended diagnostic criteria for multiple sclerosis: guidelines from the International Panel on the diagnosis of multiple sclerosis" Ann. Neurol. (2001) 50(1): 121-7.
Meng et al., "Toll-like receptor 3 upregulation in macrophages participates in the initiation and maintenance of pristine-induced arthritis in rats", Arth Res Thera. (2010) 12(3): R103; 12 pages.
Meyer et al., "Saturation Transfer Difference NMR Spectroscopy for Identifying Ligand Epitopes and Binding Specificities", Ernst Schering Res Found Workshop. (2004) 44:149-67.
Morrison et al., "Chimeric human antibody molecules: Mouse antigen-binding domains with human constant region domains", Proc Natl Acad Sci. USA (1984) 81:6851-6855.
Müller, Rolf., "Determination of Affinity and Specificity of Anti-Hapten Antibodies by Competitive Radioimmunoassay", Meth Enzymol. (1983) 92:589-601.
Murphy et al., "Regulation of interleukin 12 p40 expression through an NF-kappa B half-site", Mol Cell Biol. (1995) 15:5258-5267.
Nakamura et al., "Increased expression of Toll-like receptor 3 in intrahepatic biliary epithelial cells at sites of ductular reaction in diseased livers", Hepatol Int. (2008) 2(2): 222-230.
NCBI accession No. NM_003265. Retrieved May 24, 2011, from http://www.ncbi.nlm.nih.gov/nuccore/NM_003265.
NCBI accession No. NP_003256. Retrieved May 24, 2011, from http://www.ncbi.nlm.nih.gov/protein/NP_003256.
NCBI accession No. NP_612564; http://www.ncbi.nlm.nih.gov/protein/NP 612564, Feb. 9, 2014.
NCBI accession No. BAG55033; toll-like receptor 3; Dec. 5, 2008; 2 pages.
Nice et al., "Mapping of the antibody- and receptor-binding domains of granulocyte colony-stimulating factor using an optical biosensor", J Chromatogr. (1993) 646:159-168.
O'Connor et al., "Comparison of Arterial and Venous Blood Gases and the Effects of Analysis Delay and Air Contamination on Arterial Samples in Patients with Chronic Obstructive Pulmonary Disease and Healthy Controls", Respiration (2011) 81: 18-25.
O'Dell, James R., "Drug therapy: therapeutic strategies for rheumatoid arthritis." New Engl J Med. (2004) 350:2591-2602.
Paradowska et al., "Pro-inflammatory cytokines gene polymorphisms in Rheumatoid Arthritis" Centr Eur J Immunol. (2006) 31(3-4):117-122.
Pariente et al., "Development of the Crohn's Disease Digestive Damage score, the Lémann score"; Inflamm Bowel Dis. (2011) 17(6):1415-1422 [avail. Online Nov. 28, 2010].
Paulus et al., "Monitoring radiographic changes in early rheumatoid arthritis" J Rheumatol. (1996) 23: 801-805.
Plückthun, Andreas, "Mono- and Bivalent Antibody Fragments Produced in *Escherichia coli*: Engineering, Folding and Antigen Binding", Immunol Rev. (1992) 130: 151-188.
Presta et al., "Humanization of an Antibody Directed Against IgE", J Immunol. (1993) 151(5):2623-2632.
Presta, Leonard G., "Antibody engineering", Curr Opin Struct Biol. (1992) 2:593-596.

(56) References Cited

OTHER PUBLICATIONS

Rahman et al., "The role of toll-like receptors in systemic lupus erythematosus", Springer Semin Immun. (2006) 28:131-143.
Ranjith-Kumar et al. "Biochemical and functional analyses of the human Toll-like receptor 3 ectodomain", J Biol Chem. (2007) 282(10):7668-7678.
Riechmann et al., "Reshaping human antibodies for therapy", Nature (1988) 332:323-327.
Sacre et al., Inhibitors of TLR82008. J. Immunol., 181:8002-8009.
Saito et al., "Nuclear Magnetic Resonance Spectroscopy for the Study of B-Cell Epitopes", Methods (1996) 9(3):516-524.
Sandborn et al., "A review of activity indices and efficacy endpoints for clinical trials of medical therapy for adults with Crohn's disease" Gastroenterology (2002) 122(2):512-530.
Sanderson et al., "In vivo Drug-Linker Stability of an Anti-CD30 Dipeptide-linked Auristatin Immunoconjugate", Clin Canc Res. (2005) 11:843-852.
Saunal et al., "Mapping of viral conformational epitopes using biosensor measurements", J Immunol Meth. (1995) 183:33-41.
Scott et al., "The links between joint damage and disability in rheumatoid arthritis", Rheumatology (2000) 39:122-132.
Sims et al., "A Humanized CD18 Antibody can block Function without Cell Destruction", J Immunol. (1993) 151:2296-2308.
Skerra, Arne, "Bacterial expression of immunoglobulin fragments", Curr Op. Immunol. (1993) 5: 256-262.
Smith, Douglas W. (Ed.), Biocomputing—Informatics and Genome Projects, Academic Press, Inc. (1993) Table of Contents, 7 pages.
Song et al., Characterization of a novel anti-human TNF-alpha murine monoclonal antibody with high binding affinity and neutralizing activity. Exp Mol Med. (2008) 40(1):35-42.
Sun et al., "Structural and functional analyses of the human toll-like receptor 3: Role of glycosylation", J Biol Chem. (2006) 281(16):11144-11151.
Takada et al., "C-terminal LRRs of human Toll-like receptor 3 control receptor dimerization and signal transmission", Mol Immunol. (2007) 44(15):3633-3640.
Takii et al., "Enhanced expression of type I interferon and toll-like receptor-3 in primary biliary cirrhosis", Lab Invest. (2005) 85(7):908-920.
Taylor et al., "Human immunoglobulin transgenes undergo rearrangement, somatic mutation and class switching in mice that lack endogenous IgM". Int Immunol. (1994) 6(4):579-591.
Verhoeyen et al., Reshaping Human Antibodies: Grafting an Antilysozyme Activity. Science (1988) 239:1534-1536.
Von Heinje, Gunnar [Ed.] "Sequence Analysis in Molecular Biology—Treasure Trove or Trivial Pursuit", 1987, Academic Press [TOC Only].
Wales, et al., "Hydrogen exchange mass spectrometry for the analysis of protein dynamics", Mass Spectrom Rev. (2006) 25:158-165.
Walters, Kenneth A. [Ed.], Dermatological and transdermal formulations (drugs and the pharmaceutical sciences), vol. 119, Dekker, New York, (2002) TOC; 4 pages.
Wang et al., "Identification of a Fab interaction footprint site on an icosahedral virus by cryoelectron microscopy and X-ray crystallography", Nature (1992) 355:275-278.
Ward et al., Binding Activities of a Repertoire of Single Immunoglobulin Variable Domains Secreted From *Escherichia coli*. Nature (1989) 341:544-546.
Weis et al., "Semi-Automated Data Processing of Hydrogen Exchange Mass Spectra Using HX-Express", J Am Soc Mass Spectrom. (2006) 17:1700-1703.
Wells, James A., "Binding in the growth hormone receptor complex", Proc Natl Acad Sci. USA (1996) 93:1-6.
Wen et al., "The Effect of Innate Immunity on Autoimmune Diabetes and the Expression of Toll-Like Receptors on Pancreatic Islets", J Immunol. (2004) 172: 3172-3180.
Wietek et al., "Interferon regulatory factor-3-mediated activation of the interferon-sensitive response element by toll-like receptor (TLR) 4 but not TLR3 requires the p65 subunit of NF-kB", J Biol Chem. (2003) 278(51):50923-50931.
Yin et al., "Toll-Like Receptor 3 in Liver Diseases" Gastroent Res Pract. (2010) Article ID 750904, 6 pages.
Zorde-Khvalevsky et al., "Toll-like receptor 3 signaling attenuates liver regeneration", Hepatology (2009) 50(1):198-206.
U.S. Appl. No. 61/109,974, filed Oct. 31, 2008.
U.S. Appl. No. 61/161,860, filed Mar. 20, 2009.
U.S. Appl. No. 61/165,100, filed Mar. 31, 2009.
U.S. Appl. No. 61/173,686, filed Apr. 29, 2009.
U.S. Appl. No. 61/670,289, filed Jul. 11, 2012.
U.S. Appl. No. 61/653,652, filed May 31, 2012.
U.S. Appl. No. 61/679,923, filed Aug. 6, 2012.
U.S. Appl. No. 61/224,548, filed Jul. 10, 2009.
U.S. Office Action dated Apr. 1, 2014 in U.S. Appl. No. 13/102,019, filed May 5, 2011.
U.S. Response dated May 6, 2014 in U.S. Appl. No. 13/102,019, filed May 5, 2011.
U.S. Office Action dated Aug. 6, 2014 in U.S. Appl. No. 13/102,019, filed May 5, 2011.
U.S. Response dated Nov. 5, 2014 in U.S. Appl. No. 13/102,019, filed May 5, 2011.
International Search Report for PCT/EP2010/059946 dated Mar. 30, 2011.
International Preliminary Report on Patentability and Written Opinion for PCT/EP2010/059946 dated Jan. 10, 2012.
International Search Report for PCT/EP2012/050321 dated Jul. 25, 2012.
International Preliminary Report on Patentability and Written Opinion for PCT/EP2012/050321 dated Jul. 16, 2013.
International Search Report for PCT/EP2013/061173 dated Sep. 4, 2013.
International Preliminary Report on Patentability and Written Opinion for PCT/EP2013/061173 dated Dec. 2, 2014.
International Search Report for PCT/US2013/060886 dated Dec. 13, 2013.
U.S. Office Action dated Dec. 1, 2011 in U.S. Appl. No. 12/609,675, filed Oct. 30, 2009.
U.S. Response dated Feb. 1, 2012 in U.S. Appl. No. 12/609,675, filed Oct. 30, 2009.
U.S. Office Action dated Apr. 11, 2012 in U.S. Appl. No. 12/609,675, filed Oct. 30, 2009.
U.S. Response dated Aug. 8, 2012 in U.S. Appl. No. 12/609,675, filed Oct. 30, 2009.
U.S. Notice of Allowance dated Oct. 29, 2012 in U.S. Appl. No. 12/609,675, filed Oct. 30, 2009.
U.S. Office Action dated Mar. 19, 2012 in U.S. Appl. No. 12/770,147, filed Apr. 29, 2010.
U.S. Response dated Apr. 19, 2012 in U.S. Appl. No. 12/770,147, filed Apr. 29, 2010.
U.S. Office Action dated May 31, 2012 in U.S. Appl. No. 12/770,147, filed Apr. 29, 2010.
U.S. Response dated Oct. 26, 2012 in U.S. Appl. No. 12/770,147, filed Apr. 29, 2010.
U.S. Office Action dated Nov. 2, 2012 in U.S. Appl. No. 12/770,147, filed Apr. 29, 2010.
U.S. Response dated Nov. 30, 2012 in U.S. Appl. No. 12/770,147, filed Apr. 29, 2010.
U.S. Notice of Allowance dated Feb. 1, 2013 in U.S. Appl. No. 12/770,147, filed Apr. 29, 2010.
U.S. Response/RCE dated Apr. 30, 2013 in U.S. Appl. No. 12/770,147, filed Apr. 29, 2010.
U.S. Notice of Allowance dated May 21, 2013 in U.S. Appl. No. 12/770,147, filed Apr. 29, 2010.
U.S. Office Action dated Sep. 26, 2012 in U.S. Appl. No. 13/230,060, filed Sep. 12, 2011.
U.S. Response dated Dec. 20, 2012 in U.S. Appl. No. 13/230,060, filed Sep. 12, 2011.
U.S. Notice of Allowance dated Feb. 6, 2013 in U.S. Appl. No. 13/230,060, filed Sep. 12, 2011.
U.S. Response (312) dated May 2, 2013 in U.S. Appl. No. 13/230,060, filed Sep. 12, 2011.

(56) References Cited

OTHER PUBLICATIONS

U.S. Office Action dated Jan. 3, 2014 in U.S. Appl. No. 13/628,434, filed Sep. 27, 2012.
U.S. Notice of Abandonment dated Jul. 31, 2014 in U.S. Appl. No. 13/628,434, filed Sep. 27, 2012.
U.S. Office Action dated Mar. 31, 2014 in U.S. Appl. No. 13/751,718, filed Jan. 28, 2013.
U.S. Response dated May 29, 2014 in U.S. Appl. No. 13/751,718, filed Jan. 28, 2013.
U.S. Office Action dated Aug. 6, 2014 in U.S. Appl. No. 13/751,718, filed Jan. 28, 2013.
U.S. Response dated Dec. 5, 2014 in U.S. Appl. No. 13/751,718, filed Jan. 28, 2013.
U.S. Office Action dated Dec. 5, 2013 in U.S. Appl. No. 13/887,797, filed May 6, 2013.
U.S. Notice of Abandonment dated Jul. 3, 2014 in U.S. Appl. No. 13/887,797, filed May 6, 2013.
U.S. Office Action dated Apr. 24, 2014 in U.S. Appl. No. 13/777,513, filed Feb. 26, 2013.
U.S. Response dated Jun. 23, 2014 in U.S. Appl. No. 13/777,513, filed Feb. 26, 2013.
U.S. Office Action dated Aug. 28, 2014 in U.S. Appl. No. 13/777,513, filed Feb. 26, 2013.
U.S. Response dated Nov. 26, 2014 in U.S. Appl. No. 13/777,513, filed Feb. 26, 2013.
U.S. Notice of Allowance dated Jan. 13, 2015 in U.S. Appl. No. 13/777,513, filed Feb. 26, 2013.
U.S. Office Action dated May 22, 2014 in U.S. Appl. No. 13/798,494, filed Mar. 13, 2013.
U.S. Response dated Jul. 22, 2014 in U.S. Appl. No. 13/798,494, filed Mar. 13, 2013.
U.S. Office Action dated Sep. 29, 2014 in U.S. Appl. No. 13/798,494, filed Mar. 13, 2013.
U.S. Response dated Dec. 29, 2014 in U.S. Appl. No. 13/798,494, filed Mar. 13, 2013.
U.S. Office Action dated Apr. 7, 2017 in U.S. Appl. No. 15/345,860, filed Nov. 8, 2016.

\* cited by examiner

IP-10 in BALF

SEQUENCE LISTING

```
<160> NUMBER OF SEQ ID NOS: 122

<210> SEQ ID NO 1
<211> LENGTH: 900
<212> TYPE: PRT
<213> ORGANISM: Homo sapiens

<400> SEQUENCE: 1

Met Arg Gln Thr Leu Pro Cys Ile Tyr Phe Trp Gly Gly Leu Leu Pro
1               5                   10                  15

Phe Gly Met Leu Cys Ala Ser Ser Thr Thr Lys Cys Thr Val Ser His
            20                  25                  30

Glu Val Ala Asp Cys Ser His Leu Lys Leu Thr Gln Val Pro Asp Asp
        35                  40                  45

Leu Pro Thr Asn Ile Thr Val Leu Asn Leu Thr His Asn Gln Leu Arg
    50                  55                  60

Arg Leu Pro Ala Ala Asn Phe Thr Arg Tyr Ser Gln Leu Thr Ser Leu
65                  70                  75                  80

Asp Val Gly Phe Asn Thr Ile Ser Lys Leu Glu Pro Glu Leu Cys Gln
                85                  90                  95

Lys Leu Pro Met Leu Lys Val Leu Asn Leu Gln His Asn Glu Leu Ser
            100                 105                 110

Gln Leu Ser Asp Lys Thr Phe Ala Phe Cys Thr Asn Leu Thr Glu Leu
        115                 120                 125

His Leu Met Ser Asn Ser Ile Gln Lys Ile Lys Asn Asn Pro Phe Val
    130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
            180                 185                 190

Ile Phe Ala Asn Ser Ser Leu Lys Lys Leu Glu Leu Ser Ser Asn Gln
        195                 200                 205
```

```
Ile Lys Glu Phe Ser Pro Gly Cys Phe His Ala Ile Gly Arg Leu Phe
    210                 215                 220

Gly Leu Phe Leu Asn Asn Val Gln Leu Gly Pro Ser Leu Thr Glu Lys
225                 230                 235                 240

Leu Cys Leu Glu Leu Ala Asn Thr Ser Ile Arg Asn Leu Ser Leu Ser
                245                 250                 255

Asn Ser Gln Leu Ser Thr Thr Ser Asn Thr Thr Phe Leu Gly Leu Lys
            260                 265                 270

Trp Thr Asn Leu Thr Met Leu Asp Leu Ser Tyr Asn Asn Leu Asn Val
        275                 280                 285

Val Gly Asn Asp Ser Phe Ala Trp Leu Pro Gln Leu Glu Tyr Phe Phe
290                 295                 300

Leu Glu Tyr Asn Asn Ile Gln His Leu Phe Ser His Ser Leu His Gly
305                 310                 315                 320

Leu Phe Asn Val Arg Tyr Leu Asn Leu Lys Arg Ser Phe Thr Lys Gln
                325                 330                 335

Ser Ile Ser Leu Ala Ser Leu Pro Lys Ile Asp Asp Phe Ser Phe Gln
            340                 345                 350

Trp Leu Lys Cys Leu Glu His Leu Asn Met Glu Asp Asn Asp Ile Pro
        355                 360                 365

Gly Ile Lys Ser Asn Met Phe Thr Gly Leu Ile Asn Leu Lys Tyr Leu
370                 375                 380

Ser Leu Ser Asn Ser Phe Thr Ser Leu Arg Thr Leu Thr Asn Glu Thr
385                 390                 395                 400

Phe Val Ser Leu Ala His Ser Pro Leu His Ile Leu Asn Leu Thr Lys
                405                 410                 415

Asn Lys Ile Ser Lys Ile Glu Ser Asp Ala Phe Ser Trp Leu Gly His
            420                 425                 430

Leu Glu Val Leu Asp Leu Gly Leu Asn Glu Ile Gly Gln Glu Leu Thr
        435                 440                 445

Gly Gln Glu Trp Arg Gly Leu Glu Asn Ile Phe Glu Ile Tyr Leu Ser
450                 455                 460

Tyr Asn Lys Tyr Leu Gln Leu Thr Arg Asn Ser Phe Ala Leu Val Pro
465                 470                 475                 480

Ser Leu Gln Arg Leu Met Leu Arg Arg Val Ala Leu Lys Asn Val Asp
                485                 490                 495

Ser Ser Pro Ser Pro Phe Gln Pro Leu Arg Asn Leu Thr Ile Leu Asp
            500                 505                 510

Leu Ser Asn Asn Asn Ile Ala Asn Ile Asn Asp Asp Met Leu Glu Gly
        515                 520                 525

Leu Glu Lys Leu Glu Ile Leu Asp Leu Gln His Asn Asn Leu Ala Arg
530                 535                 540

Leu Trp Lys His Ala Asn Pro Gly Gly Pro Ile Tyr Phe Leu Lys Gly
545                 550                 555                 560

Leu Ser His Leu His Ile Leu Asn Leu Glu Ser Asn Gly Phe Asp Glu
                565                 570                 575

Ile Pro Val Glu Val Phe Lys Asp Leu Phe Glu Leu Lys Ile Ile Asp
            580                 585                 590

Leu Gly Leu Asn Asn Leu Asn Thr Leu Pro Ala Ser Val Phe Asn Asn
        595                 600                 605

Gln Val Ser Leu Lys Ser Leu Asn Leu Gln Lys Asn Leu Ile Thr Ser
610                 615                 620

Val Glu Lys Lys Val Phe Gly Pro Ala Phe Arg Asn Leu Thr Glu Leu
```

```
                625                 630                 635                 640
Asp Met Arg Phe Asn Pro Phe Asp Cys Thr Cys Glu Ser Ile Ala Trp
                    645                 650                 655
Phe Val Asn Trp Ile Asn Glu Thr His Thr Asn Ile Pro Glu Leu Ser
                660                 665                 670
Ser His Tyr Leu Cys Asn Thr Pro His Tyr His Gly Phe Pro Val
                675                 680                 685
Arg Leu Phe Asp Thr Ser Ser Cys Lys Asp Ser Ala Pro Phe Glu Leu
                690                 695                 700
Phe Phe Met Ile Asn Thr Ser Ile Leu Leu Ile Phe Ile Phe Ile Val
705                 710                 715                 720
Leu Leu Ile His Phe Glu Gly Trp Arg Ile Ser Phe Tyr Trp Asn Val
                725                 730                 735
Ser Val His Arg Val Leu Gly Phe Lys Glu Ile Asp Arg Gln Thr Glu
                740                 745                 750
Gln Phe Glu Tyr Ala Ala Tyr Ile Ile His Ala Tyr Lys Asp Lys Asp
                755                 760                 765
Trp Val Trp Glu His Phe Ser Ser Met Glu Lys Glu Asp Gln Ser Leu
770                 775                 780
Lys Phe Cys Leu Glu Glu Arg Asp Phe Glu Ala Gly Val Phe Glu Leu
785                 790                 795                 800
Glu Ala Ile Val Asn Ser Ile Lys Arg Ser Arg Lys Ile Ile Phe Val
                805                 810                 815
Ile Thr His His Leu Leu Lys Asp Pro Leu Cys Lys Arg Phe Lys Val
                820                 825                 830
His His Ala Val Gln Gln Ala Ile Glu Gln Asn Leu Asp Ser Ile Ile
                835                 840                 845
Leu Val Phe Leu Glu Glu Ile Pro Asp Tyr Lys Leu Asn His Ala Leu
                850                 855                 860
Cys Leu Arg Arg Gly Met Phe Lys Ser His Cys Ile Leu Asn Trp Pro
865                 870                 875                 880
Val Gln Lys Glu Arg Ile Gly Ala Phe Arg His Lys Leu Gln Val Ala
                    885                 890                 895
Leu Gly Ser Lys
            900

<210> SEQ ID NO 2
<211> LENGTH: 904
<212> TYPE: PRT
<213> ORGANISM: Macaca fascicularis

<400> SEQUENCE: 2

Met Arg Gln Thr Leu Pro Tyr Thr Tyr Phe Trp Trp Gly Leu Leu Pro
1               5                   10                  15
Phe Gly Met Leu Cys Ala Ser Ser Thr Asn Lys Cys Thr Val Ser Gln
                20                  25                  30
Glu Val Ala Asp Cys Ser His Leu Lys Leu Thr Gln Val Pro Asp Asp
            35                  40                  45
Leu Pro Thr Asn Ile Thr Val Leu Asn Leu Thr His Asn Gln Leu Arg
        50                  55                  60
Arg Leu Pro Ala Ala Asn Phe Thr Arg Tyr Ser Gln Leu Thr Ile Leu
65                  70                  75                  80
Asp Val Gly Phe Asn Ser Ile Ser Lys Leu Glu Pro Glu Leu Cys Gln
                85                  90                  95
```

```
Lys Leu Pro Met Leu Lys Val Leu Asn Leu Gln His Asn Glu Leu Ser
            100                 105                 110

Gln Leu Ser Asp Lys Thr Phe Ala Phe Cys Thr Asn Leu Thr Glu Leu
        115                 120                 125

His Leu Met Ser Asn Ser Ile Gln Lys Ile Lys Asn Asn Pro Phe Val
    130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Gly
            180                 185                 190

Ile Leu Ala Asn Ser Ser Leu Lys Lys Leu Glu Leu Ser Ser Asn Gln
        195                 200                 205

Ile Lys Glu Phe Ser Pro Gly Cys Phe His Ala Ile Gly Arg Leu Leu
    210                 215                 220

Gly Leu Phe Leu Asn Asn Val Gln Leu Gly Pro Arg Leu Thr Glu Lys
225                 230                 235                 240

Leu Cys Leu Glu Leu Ala Asn Thr Ser Val Arg Asn Leu Ser Leu Ser
                245                 250                 255

Asn Ser Gln Leu Ser Thr Thr Ser Asn Thr Thr Phe Leu Gly Leu Lys
            260                 265                 270

Trp Thr Asn Leu Thr Met Leu Asp Leu Ser His Asn Asn Leu Asn Val
        275                 280                 285

Ile Gly Asn Asp Ser Phe Val Trp Leu Pro His Leu Glu Tyr Phe Phe
    290                 295                 300

Leu Glu Tyr Asn Asn Ile Gln His Leu Leu Ser His Ser Leu His Gly
305                 310                 315                 320

Leu Phe Asn Val Arg Tyr Leu Asn Leu Lys Arg Ser Phe Thr Lys Gln
                325                 330                 335

Ser Ile Ser Leu Ala Ser Leu Pro Lys Ile Asp Asp Phe Ser Phe Arg
            340                 345                 350

Trp Leu Thr Cys Leu Glu His Leu Asn Met Glu Asp Asn Asp Ile Ser
        355                 360                 365

Gly Ile Lys Ser Asn Met Phe Thr Gly Leu Ile Asn Leu Lys Tyr Leu
    370                 375                 380

Ser Leu Ser Asn Ser Phe Thr Ser Leu Gln Thr Leu Thr Asn Glu Thr
385                 390                 395                 400

Phe Val Ser Leu Ala His Ser Pro Leu His Ile Leu Asn Leu Thr Lys
                405                 410                 415

Asn Lys Ile Ser Lys Ile Glu Ser Gly Ala Phe Ser Trp Leu Gly His
            420                 425                 430

Leu Glu Val Leu Asp Leu Gly Leu Asn Glu Ile Gly Gln Glu Leu Thr
        435                 440                 445

Gly Gln Glu Trp Ser Gly Leu Glu Asn Ile Phe Glu Ile Tyr Leu Ser
    450                 455                 460

Tyr Asn Lys Tyr Leu Gln Leu Thr Lys Asn Ser Phe Ala Leu Val Arg
465                 470                 475                 480

Ser Leu Gln Arg Leu Met Leu Arg Arg Val Ala Leu Lys Asn Val Asp
                485                 490                 495

Cys Ser Pro Ser Pro Phe Gln Pro Leu Gly Asn Leu Thr Ile Leu Asp
            500                 505                 510

Leu Ser Asn Asn Asn Ile Ala Asn Ile Asn Asp Asp Met Leu Glu Gly
```

```
                515                 520                 525
Leu Glu Lys Leu Glu Ile Leu Asp Leu Gln His Asn Asn Leu Ala Arg
            530                 535                 540

Leu Trp Lys His Ala Asn Pro Gly Gly Pro Val Tyr Phe Leu Lys Gly
545                 550                 555                 560

Leu Ser His Leu His Ile Leu Asn Leu Glu Ser Asn Gly Phe Asp Glu
                565                 570                 575

Ile Pro Val Glu Val Phe Lys Asp Leu Ser Glu Leu Lys Ile Ile Asp
            580                 585                 590

Leu Gly Leu Asn Asn Leu Asn Thr Leu Pro Ala Ser Val Phe Asp Asn
        595                 600                 605

Gln Val Ser Leu Lys Ser Leu Asn Leu Gln Lys Asn Leu Ile Thr Ser
    610                 615                 620

Val Glu Lys Lys Val Phe Gly Pro Ala Phe Arg Asn Leu Ser Asn Leu
625                 630                 635                 640

Asp Met Arg Phe Asn Pro Phe Asp Cys Thr Cys Glu Ser Ile Ala Trp
                645                 650                 655

Phe Val Asn Trp Ile Asn Lys Thr His Ala Asn Ile Pro Glu Leu Ser
            660                 665                 670

Ser His Tyr Leu Cys Asn Thr Pro Pro His Tyr His Gly Phe Pro Val
        675                 680                 685

Arg Leu Phe Asp Thr Ser Ser Cys Lys Asp Ser Ala Pro Phe Glu Leu
    690                 695                 700

Phe Phe Ile Ile Asn Thr Ser Ile Leu Leu Ile Phe Ile Phe Val Val
705                 710                 715                 720

Leu Leu Ile His Phe Glu Gly Trp Arg Ile Ser Phe Tyr Trp Asn Val
                725                 730                 735

Ser Val His Arg Val Leu Gly Phe Lys Glu Ile Asp Arg Gln Thr Glu
            740                 745                 750

Gln Phe Glu Tyr Ala Ala Tyr Ile Ile His Ala His Lys Asp Lys Asp
        755                 760                 765

Trp Val Trp Glu His Phe Ser Ser Met Glu Lys Glu Asp Gln Ser Leu
    770                 775                 780

Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Ile
                805                 810                 815

Ile Thr His His Leu Leu Lys Asp Pro Leu Cys Lys Arg Phe Lys Val
            820                 825                 830

His His Ala Val Gln Gln Ala Ile Glu Gln Asn Leu Asp Ser Ile Ile
        835                 840                 845

Leu Ile Phe Leu Glu Glu Ile Pro Asp Tyr Lys Leu Asn His Ala Leu
    850                 855                 860

Cys Leu Arg Arg Gly Met Phe Lys Ser His Cys Ile Leu Asn Trp Pro
865                 870                 875                 880

Val Gln Lys Glu Arg Ile Gly Ala Phe His His Lys Leu Gln Val Ala
                885                 890                 895

Leu Gly Ser Lys Asn Ser Val His
            900

<210> SEQ ID NO 3
<211> LENGTH: 125
<212> TYPE: PRT
<213> ORGANISM: Mus musculus
```

-continued

<400> SEQUENCE: 3

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Asn Tyr
            20                  25                  30

Trp Met Asn Trp Val Lys Gln Arg Pro Gly Gln Gly Leu Glu Trp Ile
        35                  40                  45

Gly Met Ile Asp Pro Ser Asp Ser Glu Thr His Tyr Asn Gln Met Phe
    50                  55                  60

Lys Asp Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Ala Ser Ser Asp Tyr Tyr Phe Asp Tyr Trp Gly
            100                 105                 110

Gln Gly Thr Thr Leu Thr Val Ser Ser Ala Ser Thr Lys
        115                 120                 125

<210> SEQ ID NO 4
<211> LENGTH: 109
<212> TYPE: PRT
<213> ORGANISM: Mus musculus

<400> SEQUENCE: 4

Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile His Asp Asp
            20                  25                  30

Ile Asn Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Arg
                85                  90                  95

Thr Phe Gly Gly Gly Thr Lys Leu Glu Ile Lys Arg Thr
            100                 105

<210> SEQ ID NO 5
<211> LENGTH: 5
<212> TYPE: PRT
<213> ORGANISM: Mus musculus

<400> SEQUENCE: 5

Asn Tyr Trp Met Asn
1               5

<210> SEQ ID NO 6
<211> LENGTH: 6
<212> TYPE: PRT
<213> ORGANISM: Mus musculus

<400> SEQUENCE: 6

Gly Tyr Thr Phe Thr Asn
1               5

```
<210> SEQ ID NO 7
<211> LENGTH: 10
<212> TYPE: PRT
<213> ORGANISM: Mus musculus

<400> SEQUENCE: 7

Gly Tyr Thr Phe Thr Asn Tyr Trp Met Asn
1               5                   10

<210> SEQ ID NO 8
<211> LENGTH: 17
<212> TYPE: PRT
<213> ORGANISM: Mus musculus

<400> SEQUENCE: 8

Met Ile Asp Pro Ser Asp Ser Glu Thr His Tyr Asn Gln Met Phe Lys
1               5                   10                  15

Asp

<210> SEQ ID NO 9
<211> LENGTH: 10
<212> TYPE: PRT
<213> ORGANISM: Mus musculus

<400> SEQUENCE: 9

Met Ile Asp Pro Ser Asp Ser Glu Thr His
1               5                   10

<210> SEQ ID NO 10
<211> LENGTH: 11
<212> TYPE: PRT
<213> ORGANISM: Mus musculus

<400> SEQUENCE: 10

Gly Ala Ser Ser Asp Tyr Tyr Tyr Phe Asp Tyr
1               5                   10

<210> SEQ ID NO 11
<211> LENGTH: 11
<212> TYPE: PRT
<213> ORGANISM: Mus musculus

<400> SEQUENCE: 11

Ile Thr Ser Thr Asp Ile His Asp Asp Ile Asn
1               5                   10

<210> SEQ ID NO 12
<211> LENGTH: 7
<212> TYPE: PRT
<213> ORGANISM: Rattus norvegicus

<400> SEQUENCE: 12

Glu Gly Asn Thr Leu Arg Pro
1               5

<210> SEQ ID NO 13
<211> LENGTH: 9
<212> TYPE: PRT
<213> ORGANISM: Mus musculus

<400> SEQUENCE: 13

Leu Gln Ser Asp Asn Leu Pro Arg Thr
1               5
```

<210> SEQ ID NO 14
<211> LENGTH: 121
<212> TYPE: PRT
<213> ORGANISM: Rattus norvegicus

<400> SEQUENCE: 14

Glu Val Gln Leu Gln Gln Ser Gly Ala Glu Leu Gly Lys Pro Gly Thr
1               5                   10                  15

Ser Val Lys Leu Ser Cys Lys Val Ser Gly Tyr Asn Ile Arg Tyr Thr
            20                  25                  30

Tyr Met His Trp Val Asn Gln Arg Pro Gly Lys Gly Leu Glu Trp Ile
        35                  40                  45

Gly Arg Ile Asp Pro Ala Asn Gly Asp Ser Ile Tyr Gly Glu Asp Phe
    50                  55                  60

Lys Thr Lys Ala Thr Leu Thr Ala Asp Thr Ser Ser Asn Thr Ala Tyr
65                  70                  75                  80

Met Gln Leu Ser Gln Leu Lys Ser Asp Asp Thr Ala Ile Tyr Phe Cys
            85                  90                  95

Ala Met Gly Glu Phe Asp Tyr Phe Asp Tyr Trp Gly Gln Gly Val Met
        100                 105                 110

Val Thr Val Ser Ser Ala Ser Thr Lys
        115                 120

<210> SEQ ID NO 15
<211> LENGTH: 107
<212> TYPE: PRT
<213> ORGANISM: Rattus norvegicus

<400> SEQUENCE: 15

Asp Ile Gln Met Thr Gln Ser Pro Pro Ser Leu Ser Ala Ser Leu Gly
1               5                   10                  15

Glu Thr Val Ser Ile Glu Cys Leu Ala Ser Glu Gly Ile Ser Asn Asp
            20                  25                  30

Leu Ala Trp Tyr Gln Gln Arg Ser Gly Lys Ser Pro Gln Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Arg Tyr Ser Leu Lys Ile Ser Gly Met Gln Pro
65                  70                  75                  80

Glu Asp Glu Ala Asp Tyr Phe Cys Gln Gln Asn Tyr Lys Tyr Pro Leu
            85                  90                  95

Thr Phe Gly Ser Gly Thr Lys Leu Glu Ile Lys
        100                 105

<210> SEQ ID NO 16
<211> LENGTH: 5
<212> TYPE: PRT
<213> ORGANISM: Rattus norvegicus

<400> SEQUENCE: 16

Tyr Thr Tyr Met His
1               5

<210> SEQ ID NO 17
<211> LENGTH: 6
<212> TYPE: PRT
<213> ORGANISM: Rattus norvegicus

<400> SEQUENCE: 17

Gly Tyr Asn Ile Arg Tyr
1               5

<210> SEQ ID NO 18
<211> LENGTH: 10
<212> TYPE: PRT
<213> ORGANISM: Rattus norvegicus

<400> SEQUENCE: 18

Gly Tyr Asn Ile Arg Tyr Thr Tyr Met His
1               5                   10

<210> SEQ ID NO 19
<211> LENGTH: 17
<212> TYPE: PRT
<213> ORGANISM: Rattus norvegicus

<400> SEQUENCE: 19

Arg Ile Asp Pro Ala Asn Gly Asp Ser Ile Tyr Gly Glu Asp Phe Lys
1               5                   10                  15

Thr

<210> SEQ ID NO 20
<211> LENGTH: 10
<212> TYPE: PRT
<213> ORGANISM: Rattus norvegicus

<400> SEQUENCE: 20

Arg Ile Asp Pro Ala Asn Gly Asp Ser Ile
1               5                   10

<210> SEQ ID NO 21
<211> LENGTH: 8
<212> TYPE: PRT
<213> ORGANISM: Rattus norvegicus

<400> SEQUENCE: 21

Gly Glu Phe Asp Tyr Phe Asp Tyr
1               5

<210> SEQ ID NO 22
<211> LENGTH: 11
<212> TYPE: PRT
<213> ORGANISM: Rattus norvegicus

<400> SEQUENCE: 22

Leu Ala Ser Glu Gly Ile Ser Asn Asp Leu Ala
1               5                   10

<210> SEQ ID NO 23
<211> LENGTH: 7
<212> TYPE: PRT
<213> ORGANISM: Rattus norvegicus

<400> SEQUENCE: 23

Ala Ala Ser Arg Leu Gln Asp
1               5

<210> SEQ ID NO 24
<211> LENGTH: 9
<212> TYPE: PRT
<213> ORGANISM: Rattus norvegicus

<400> SEQUENCE: 24

Gln Gln Asn Tyr Lys Tyr Pro Leu Thr
1               5

<210> SEQ ID NO 25
<211> LENGTH: 119
<212> TYPE: PRT
<213> ORGANISM: Rattus norvegicus

<400> SEQUENCE: 25

Glu Val Gln Leu Gln Gln Tyr Gly Ala Glu Leu Gly Lys Pro Gly Thr
1               5                   10                  15

Ser Val Lys Leu Ser Cys Lys Val Ser Gly Tyr Asn Ile Trp Ser Thr
            20                  25                  30

Tyr Ile Tyr Trp Val Asn Gln Arg Pro Gly Lys Gly Leu Glu Trp Ile
        35                  40                  45

Gly Arg Ile Asp Pro Ala Asn Gly Asn Thr Ile Tyr Ala Glu Lys Phe
    50                  55                  60

Lys Thr Lys Ala Thr Leu Thr Ala Asp Thr Ser Asn Thr Ala Tyr
65                  70                  75                  80

Met Gln Leu Ser Gln Leu Lys Ser Asp Thr Ala Ile Tyr Phe Cys
                85                  90                  95

Ala Met Gly Asp His Gly Gly Tyr Val Met Asp Ala Trp Gly Gln Gly
            100                 105                 110

Ala Ser Val Thr Val Ser Ser
        115

<210> SEQ ID NO 26
<211> LENGTH: 107
<212> TYPE: PRT
<213> ORGANISM: Rattus norvegicus

<400> SEQUENCE: 26

Asp Ile Gln Met Thr Gln Ser Pro Gly Ser Leu Ser Ala Ser Leu Gly
1               5                   10                  15

Glu Thr Val Ser Ile Glu Cys Leu Ala Ser Glu Asp Ile Tyr Ser Tyr
            20                  25                  30

Leu Ala Trp Tyr Gln Gln Lys Pro Gly Lys Ser Pro Gln Leu Leu Ile
        35                  40                  45

Tyr Ala Ala Asn Arg Leu Glu Asp Gly Val Pro Ser Arg Phe Ser Gly
    50                  55                  60

Ser Gly Ser Gly Thr Gln Tyr Ser Leu Lys Ile Ser Gly Met Gln Pro
65                  70                  75                  80

Glu Asp Glu Gly Asp Tyr Phe Cys Leu Gln Ser Glu Phe Pro Tyr
                85                  90                  95

Thr Phe Gly Thr Gly Thr Lys Leu Glu Leu Lys
            100                 105

<210> SEQ ID NO 27
<211> LENGTH: 5
<212> TYPE: PRT
<213> ORGANISM: Rattus norvegicus

<400> SEQUENCE: 27

Ser Thr Tyr Ile Tyr
1               5

<210> SEQ ID NO 28
<211> LENGTH: 6
<212> TYPE: PRT

```
<213> ORGANISM: Rattus norvegicus

<400> SEQUENCE: 28

Gly Tyr Asn Ile Trp Ser
1               5

<210> SEQ ID NO 29
<211> LENGTH: 10
<212> TYPE: PRT
<213> ORGANISM: Rattus norvegicus

<400> SEQUENCE: 29

Gly Tyr Asn Ile Trp Ser Thr Tyr Ile Tyr
1               5                   10

<210> SEQ ID NO 30
<211> LENGTH: 17
<212> TYPE: PRT
<213> ORGANISM: Rattus norvegicus

<400> SEQUENCE: 30

Arg Ile Asp Pro Ala Asn Gly Asn Thr Ile Tyr Ala Glu Lys Phe Lys
1               5                   10                  15

Thr

<210> SEQ ID NO 31
<211> LENGTH: 10
<212> TYPE: PRT
<213> ORGANISM: Rattus norvegicus

<400> SEQUENCE: 31

Arg Ile Asp Pro Ala Asn Gly Asn Thr Ile
1               5                   10

<210> SEQ ID NO 32
<211> LENGTH: 10
<212> TYPE: PRT
<213> ORGANISM: Rattus norvegicus

<400> SEQUENCE: 32

Gly Asp His Gly Gly Tyr Val Met Asp Ala
1               5                   10

<210> SEQ ID NO 33
<211> LENGTH: 11
<212> TYPE: PRT
<213> ORGANISM: Rattus norvegicus

<400> SEQUENCE: 33

Leu Ala Ser Glu Asp Ile Tyr Ser Tyr Leu Ala
1               5                   10

<210> SEQ ID NO 34
<211> LENGTH: 7
<212> TYPE: PRT
<213> ORGANISM: Rattus norvegicus

<400> SEQUENCE: 34

Ala Ala Asn Arg Leu Glu Asp
1               5

<210> SEQ ID NO 35
<211> LENGTH: 9
<212> TYPE: PRT
```

<213> ORGANISM: Rattus norvegicus

<400> SEQUENCE: 35

Leu Gln Gly Ser Glu Phe Pro Tyr Thr
1               5

<210> SEQ ID NO 36
<211> LENGTH: 118
<212> TYPE: PRT
<213> ORGANISM: Rattus norvegicus

<400> SEQUENCE: 36

Gln Val Gln Leu Gln Gln Ser Gly Thr Glu Leu Val Lys Pro Gly Ser
1               5                   10                  15

Ser Val Lys Ile Ser Cys Lys Ala Ser Gly Tyr Thr Phe Thr Ser Asn
            20                  25                  30

Tyr Met His Trp Ile Arg Gln Leu Pro Gly Asn Gly Leu Glu Trp Ile
        35                  40                  45

Gly Trp Ile Phe Pro Gly Asp Gly Asp Thr Asn Tyr Asn Gln Lys Phe
    50                  55                  60

Asn Gly Lys Ala Thr Leu Thr Ala Asp Lys Ser Ser Ser Thr Ala Tyr
65                  70                  75                  80

Met Gln Leu Ser Ser Leu Thr Ser Glu Asp Tyr Ala Val Tyr Phe Cys
                85                  90                  95

Ala Arg Ser Asp Gly Asp Trp Tyr Phe Asp Phe Trp Gly Pro Gly Thr
            100                 105                 110

Met Val Thr Val Ser Ser
        115

<210> SEQ ID NO 37
<211> LENGTH: 107
<212> TYPE: PRT
<213> ORGANISM: Rattus norvegicus

<400> SEQUENCE: 37

Asp Ile Gln Met Thr Gln Ser Pro Gly Ser Leu Ser Ala Ser Leu Gly
1               5                   10                  15

Glu Thr Val Thr Ile Gln Cys Gln Ala Ser Glu Asp Ile Tyr Ser Gly
            20                  25                  30

Leu Ala Trp Tyr Gln Gln Lys Pro Arg Lys Ser Pro Gln Leu Leu Ile
        35                  40                  45

Ser Ala Ala Ser Arg Leu Gln Asp Gly Val Pro Ser Arg Phe Ser Gly
    50                  55                  60

Ser Gly Ser Gly Thr Gln Tyr Ser Leu Lys Ile Ser Ser Met Gln Thr
65                  70                  75                  80

Glu Asp Glu Gly Val Tyr Phe Cys Gln Gln Gly Val Lys Tyr Pro Asn
                85                  90                  95

Thr Phe Gly Pro Gly Thr Lys Leu Glu Leu Lys
            100                 105

<210> SEQ ID NO 38
<211> LENGTH: 5
<212> TYPE: PRT
<213> ORGANISM: Rattus norvegicus

<400> SEQUENCE: 38

Ser Asn Tyr Met His
1               5

<210> SEQ ID NO 39
<211> LENGTH: 6
<212> TYPE: PRT
<213> ORGANISM: Rattus norvegicus

<400> SEQUENCE: 39

Gly Tyr Thr Phe Thr Ser
1               5

<210> SEQ ID NO 40
<211> LENGTH: 10
<212> TYPE: PRT
<213> ORGANISM: Rattus norvegicus

<400> SEQUENCE: 40

Gly Tyr Thr Phe Thr Ser Asn Tyr Met His
1               5                   10

<210> SEQ ID NO 41
<211> LENGTH: 17
<212> TYPE: PRT
<213> ORGANISM: Rattus norvegicus

<400> SEQUENCE: 41

Trp Ile Phe Pro Gly Asp Gly Asp Thr Asn Tyr Asn Gln Lys Phe Asn
1               5                   10                  15
Gly

<210> SEQ ID NO 42
<211> LENGTH: 10
<212> TYPE: PRT
<213> ORGANISM: Rattus norvegicus

<400> SEQUENCE: 42

Trp Ile Phe Pro Gly Asp Gly Asp Thr Asn
1               5                   10

<210> SEQ ID NO 43
<211> LENGTH: 9
<212> TYPE: PRT
<213> ORGANISM: Rattus norvegicus

<400> SEQUENCE: 43

Ser Asp Gly Asp Trp Tyr Phe Asp Phe
1               5

<210> SEQ ID NO 44
<211> LENGTH: 11
<212> TYPE: PRT
<213> ORGANISM: Rattus norvegicus

<400> SEQUENCE: 44

Gln Ala Ser Glu Asp Ile Tyr Ser Gly Leu Ala
1               5                   10

<210> SEQ ID NO 45
<211> LENGTH: 7
<212> TYPE: PRT
<213> ORGANISM: Rattus norvegicus

<400> SEQUENCE: 45

Ala Ala Ser Arg Leu Gln Asp
1               5

<210> SEQ ID NO 46
<211> LENGTH: 9
<212> TYPE: PRT
<213> ORGANISM: Rattus norvegicus

<400> SEQUENCE: 46

Gln Gln Gly Val Lys Tyr Pro Asn Thr
1               5

<210> SEQ ID NO 47
<211> LENGTH: 117
<212> TYPE: PRT
<213> ORGANISM: Rattus norvegicus

<400> SEQUENCE: 47

Glu Val Gln Leu Gln Gln Tyr Gly Ala Glu Leu Gly Lys Pro Gly Thr
1               5                   10                  15

Ser Val Lys Leu Ser Cys Lys Val Ser Gly Tyr Asn Ile Thr Tyr Thr
            20                  25                  30

Tyr Met His Trp Val Asn Gln Arg Pro Gly Lys Gly Leu Glu Trp Ile
        35                  40                  45

Gly Arg Ile Asp Pro Ala Asn Gly Asn Thr Ile Tyr Gly Glu Lys Phe
    50                  55                  60

Lys Asn Lys Ala Thr Leu Thr Ala Asp Thr Ser Ser Asn Thr Ala Tyr
65                  70                  75                  80

Met Gln Leu Ser Gln Leu Lys Ser Asp Thr Ala Ile Tyr Phe Cys
                85                  90                  95

Ala Met Gly Glu Phe Asp Tyr Phe Asp His Trp Gly Gln Gly Val Met
            100                 105                 110

Val Thr Val Ser Ser
        115

<210> SEQ ID NO 48
<211> LENGTH: 107
<212> TYPE: PRT
<213> ORGANISM: Rattus norvegicus

<400> SEQUENCE: 48

Asp Ile Gln Met Thr Gln Ser Pro Ala Ser Leu Ser Ala Ser Leu Gly
1               5                   10                  15

Glu Thr Val Ser Ile Glu Cys Leu Ala Ser Glu Asp Ile Ser Asn Asp
            20                  25                  30

Leu Ala Trp Tyr Gln Gln Lys Ser Gly Lys Ser Pro Gln Val Leu Ile
        35                  40                  45

Tyr Ala Ala Ser Arg Leu Glu Asp Gly Val Pro Ser Arg Phe Ser Gly
    50                  55                  60

Ser Gly Ser Gly Thr Arg Tyr Ser Leu Lys Ile Ser Gly Met Gln Pro
65                  70                  75                  80

Glu Asp Glu Ala Asp Tyr Phe Cys Gln Gln Ser Tyr Lys Tyr Pro Val
                85                  90                  95

Thr Phe Gly Ser Gly Thr Lys Leu Glu Ile Lys
            100                 105

<210> SEQ ID NO 49
<211> LENGTH: 5
<212> TYPE: PRT
<213> ORGANISM: Rattus norvegicus

<400> SEQUENCE: 49

Tyr Thr Tyr Met His
1               5

<210> SEQ ID NO 50
<211> LENGTH: 6
<212> TYPE: PRT
<213> ORGANISM: Rattus norvegicus

<400> SEQUENCE: 50

Gly Tyr Asn Ile Thr Tyr
1               5

<210> SEQ ID NO 51
<211> LENGTH: 10
<212> TYPE: PRT
<213> ORGANISM: Rattus norvegicus

<400> SEQUENCE: 51

Gly Tyr Asn Ile Thr Tyr Thr Tyr Met His
1               5                   10

<210> SEQ ID NO 52
<211> LENGTH: 17
<212> TYPE: PRT
<213> ORGANISM: Rattus norvegicus

<400> SEQUENCE: 52

Arg Ile Asp Pro Ala Asn Gly Asn Thr Ile Tyr Gly Glu Lys Phe Lys
1               5                   10                  15
Asn

<210> SEQ ID NO 53
<211> LENGTH: 10
<212> TYPE: PRT
<213> ORGANISM: Rattus norvegicus

<400> SEQUENCE: 53

Arg Ile Asp Pro Ala Asn Gly Asn Thr Ile
1               5                   10

<210> SEQ ID NO 54
<211> LENGTH: 8
<212> TYPE: PRT
<213> ORGANISM: Rattus norvegicus

<400> SEQUENCE: 54

Gly Glu Phe Asp Tyr Phe Asp His
1               5

<210> SEQ ID NO 55
<211> LENGTH: 11
<212> TYPE: PRT
<213> ORGANISM: Rattus norvegicus

<400> SEQUENCE: 55

Leu Ala Ser Glu Asp Ile Ser Asn Asp Leu Ala
1               5                   10

<210> SEQ ID NO 56
<211> LENGTH: 7
<212> TYPE: PRT
<213> ORGANISM: Rattus norvegicus

<400> SEQUENCE: 56

```
Ala Ala Ser Arg Leu Glu Asp
1               5

<210> SEQ ID NO 57
<211> LENGTH: 9
<212> TYPE: PRT
<213> ORGANISM: Rattus norvegicus

<400> SEQUENCE: 57

Gln Gln Ser Tyr Lys Tyr Pro Val Thr
1               5

<210> SEQ ID NO 58
<211> LENGTH: 11
<212> TYPE: PRT
<213> ORGANISM: Rattus norvegicus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid

<400> SEQUENCE: 58

Xaa Ala Ser Glu Xaa Ile Xaa Xaa Xaa Leu Ala
1               5                   10

<210> SEQ ID NO 59
<211> LENGTH: 7
<212> TYPE: PRT
<213> ORGANISM: Rattus norvegicus
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 59

Ala Ala Xaa Arg Leu Xaa Asp
1               5

<210> SEQ ID NO 60
<211> LENGTH: 9
<212> TYPE: PRT
<213> ORGANISM: Rattus norvegicus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 60

Xaa Gln Xaa Xaa Xaa Xaa Pro Xaa Thr
1               5
```

```
<210> SEQ ID NO 61
<211> LENGTH: 5
<212> TYPE: PRT
<213> ORGANISM: rattus norvegicus
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 61

Xaa Xaa Tyr Xaa Xaa
1               5

<210> SEQ ID NO 62
<211> LENGTH: 6
<212> TYPE: PRT
<213> ORGANISM: rattus norvegicus
<220> FEATURE:
<221> NAME/KEY: misc_feature
<222> LOCATION: (3)..(6)
<223> OTHER INFORMATION: Xaa can be any naturally occurring amino acid

<400> SEQUENCE: 62

Gly Tyr Xaa Xaa Xaa Xaa
1               5

<210> SEQ ID NO 63
<211> LENGTH: 7
<212> TYPE: PRT
<213> ORGANISM: rattus norvegicus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 63

Xaa Ile Xaa Pro Xaa Xaa Gly
1               5

<210> SEQ ID NO 64
<211> LENGTH: 7
<212> TYPE: PRT
<213> ORGANISM: rattus norvegicus
<220> FEATURE:
<221> NAME/KEY: misc_feature
<222> LOCATION: (2)..(4)
<223> OTHER INFORMATION: Xaa can be any naturally occurring amino acid

<400> SEQUENCE: 64

Gly Xaa Xaa Xaa Tyr Phe Asp
1               5

<210> SEQ ID NO 65
<211> LENGTH: 50
<212> TYPE: DNA
<213> ORGANISM: Artificial
<220> FEATURE:
```

<223> OTHER INFORMATION: Primer for mutant hTLR3

<400> SEQUENCE: 65
gaaaattaaa aataatccct tgtcgagca gaagaattta atcacattag          50

<210> SEQ ID NO 66
<211> LENGTH: 50
<212> TYPE: DNA
<213> ORGANISM: Artificial
<220> FEATURE:
<223> OTHER INFORMATION: Primer for mutant hTLR3

<400> SEQUENCE: 66
ctaatgtgat taaattcttc tgctcgacaa agggattatt tttaattttc          50

<210> SEQ ID NO 67
<211> LENGTH: 45
<212> TYPE: DNA
<213> ORGANISM: Artificial
<220> FEATURE:
<223> OTHER INFORMATION: Primer for mutant hTLR3

<400> SEQUENCE: 67
caatgagcta tctcaacttt ctcgtaaaac ctttgccttc tgcac                45

<210> SEQ ID NO 68
<211> LENGTH: 45
<212> TYPE: DNA
<213> ORGANISM: Artificial
<220> FEATURE:
<223> OTHER INFORMATION: Primer for mutant hTLR3

<400> SEQUENCE: 68
gtgcagaagg caaaggtttt acgagaaagt tgagatagct cattg                45

<210> SEQ ID NO 69
<211> LENGTH: 49
<212> TYPE: DNA
<213> ORGANISM: Artificial
<220> FEATURE:
<223> OTHER INFORMATION: Primer for mutant hTLR3

<400> SEQUENCE: 69
caagagcttc tattatcaaa caatgagatt caagcgctaa aaagtgaag            49

<210> SEQ ID NO 70
<211> LENGTH: 49
<212> TYPE: DNA
<213> ORGANISM: Artificial
<220> FEATURE:
<223> OTHER INFORMATION: Primer for mutant hTLR3

<400> SEQUENCE: 70
cttcactttt tagcgcttga atctcattgt ttgataatag aagctcttg            49

<210> SEQ ID NO 71
<211> LENGTH: 48
<212> TYPE: DNA
<213> ORGANISM: Artificial
<220> FEATURE:
<223> OTHER INFORMATION: Primer for mutant hTLR3

<400> SEQUENCE: 71
gaagaactgg atatctttgc cgcttcatct ttaaaaaat tagagttg              48

```
<210> SEQ ID NO 72
<211> LENGTH: 48
<212> TYPE: DNA
<213> ORGANISM: Artificial
<220> FEATURE:
<223> OTHER INFORMATION: Primer for mutant hTLR3

<400> SEQUENCE: 72
caactctaat tttttaaag atgaagcggc aaagatatcc agttcttc                    48

<210> SEQ ID NO 73
<211> LENGTH: 45
<212> TYPE: DNA
<213> ORGANISM: Artificial
<220> FEATURE:
<223> OTHER INFORMATION: Primer for mutant hTLR3

<400> SEQUENCE: 73
ggaactcagg ttcagctggc caatctccaa gagcttctat tatca                     45

<210> SEQ ID NO 74
<211> LENGTH: 45
<212> TYPE: DNA
<213> ORGANISM: Artificial
<220> FEATURE:
<223> OTHER INFORMATION: Primer for mutant hTLR3

<400> SEQUENCE: 74
tgataataga agctcttgga gattggccag ctgaacctga gttcc                     45

<210> SEQ ID NO 75
<211> LENGTH: 28
<212> TYPE: DNA
<213> ORGANISM: Artificial
<220> FEATURE:
<223> OTHER INFORMATION: Primer for mutant hTLR3

<400> SEQUENCE: 75
gggtatatga gtcaacttca ggtggctg                                         28

<210> SEQ ID NO 76
<211> LENGTH: 27
<212> TYPE: DNA
<213> ORGANISM: Artificial
<220> FEATURE:
<223> OTHER INFORMATION: Primer for mutant hTLR3

<400> SEQUENCE: 76
ttgactcata tacccgatga tctaccc                                          27

<210> SEQ ID NO 77
<211> LENGTH: 28
<212> TYPE: DNA
<213> ORGANISM: Artificial
<220> FEATURE:
<223> OTHER INFORMATION: Primer for mutant hTLR3

<400> SEQUENCE: 77
taattgttgg agttgattat gggtaagg                                         28

<210> SEQ ID NO 78
<211> LENGTH: 30
<212> TYPE: DNA
<213> ORGANISM: Artificial
<220> FEATURE:
<223> OTHER INFORMATION: Primer for mutant hTLR3
```

```
<400> SEQUENCE: 78
caactccaac aattaccagc cgccaacttc                                    30

<210> SEQ ID NO 79
<211> LENGTH: 38
<212> TYPE: DNA
<213> ORGANISM: Artificial
<220> FEATURE:
<223> OTHER INFORMATION: Primer for mutant hTLR3

<400> SEQUENCE: 79
ctccagttgt gagatggagt taaatcctac atccaagc                           38

<210> SEQ ID NO 80
<211> LENGTH: 37
<212> TYPE: DNA
<213> ORGANISM: Artificial
<220> FEATURE:
<223> OTHER INFORMATION: Primer for mutant hTLR3

<400> SEQUENCE: 80
atctcacaac tggagccaga attgtgccag aaacttc                            37

<210> SEQ ID NO 81
<211> LENGTH: 34
<212> TYPE: DNA
<213> ORGANISM: Artificial
<220> FEATURE:
<223> OTHER INFORMATION: Primer for mutant hTLR3

<400> SEQUENCE: 81
taacaaggga agtatctggc acaattctgg ctcc                               34

<210> SEQ ID NO 82
<211> LENGTH: 31
<212> TYPE: DNA
<213> ORGANISM: Artificial
<220> FEATURE:
<223> OTHER INFORMATION: Primer for mutant hTLR3

<400> SEQUENCE: 82
atacttccct tgttaaaagt tttgaacctc c                                  31

<210> SEQ ID NO 83
<211> LENGTH: 36
<212> TYPE: DNA
<213> ORGANISM: Artificial
<220> FEATURE:
<223> OTHER INFORMATION: Primer for mutant hTLR3

<400> SEQUENCE: 83
gaagacaaag gtttgatcag aaagttgaga tagctc                             36

<210> SEQ ID NO 84
<211> LENGTH: 30
<212> TYPE: DNA
<213> ORGANISM: Artificial
<220> FEATURE:
<223> OTHER INFORMATION: Primer for mutant hTLR3

<400> SEQUENCE: 84
caaacctttg tcttctgcac gaatttgact                                    30

<210> SEQ ID NO 85
<211> LENGTH: 25
```

<210> SEQ ID NO 85
<211> LENGTH: 25
<212> TYPE: DNA
<213> ORGANISM: Artificial
<220> FEATURE:
<223> OTHER INFORMATION: Primer for mutant hTLR3

<400> SEQUENCE: 85
gtggattgag ttggacatga gatgg                                         25

<210> SEQ ID NO 86
<211> LENGTH: 33
<212> TYPE: DNA
<213> ORGANISM: Artificial
<220> FEATURE:
<223> OTHER INFORMATION: Primer for mutant hTLR3

<400> SEQUENCE: 86
tccaactcaa tccacaaaat taaaaataat ccc                                33

<210> SEQ ID NO 87
<211> LENGTH: 29
<212> TYPE: DNA
<213> ORGANISM: Artificial
<220> FEATURE:
<223> OTHER INFORMATION: Primer for mutant hTLR3

<400> SEQUENCE: 87
attagattta attttctgga ttgagttgg                                     29

<210> SEQ ID NO 88
<211> LENGTH: 30
<212> TYPE: DNA
<213> ORGANISM: Artificial
<220> FEATURE:
<223> OTHER INFORMATION: Primer for mutant hTLR3

<400> SEQUENCE: 88
aaaattaaat ctaatccctt tgtcaagcag                                    30

<210> SEQ ID NO 89
<211> LENGTH: 31
<212> TYPE: DNA
<213> ORGANISM: Artificial
<220> FEATURE:
<223> OTHER INFORMATION: Primer for mutant hTLR3

<400> SEQUENCE: 89
ctgattctta aagggattat ttttaatttt c                                  31

<210> SEQ ID NO 90
<211> LENGTH: 34
<212> TYPE: DNA
<213> ORGANISM: Artificial
<220> FEATURE:
<223> OTHER INFORMATION: Primer for mutant hTLR3

<400> SEQUENCE: 90
ccctttaaga atcagaagaa tttaatcaca ttag                               34

<210> SEQ ID NO 91
<211> LENGTH: 33
<212> TYPE: DNA
<213> ORGANISM: Artificial
<220> FEATURE:
<223> OTHER INFORMATION: Primer for mutant hTLR3

<400> SEQUENCE: 91
tgtgattaaa ttcgcctgct tgacaaaggg att                          33

<210> SEQ ID NO 92
<211> LENGTH: 24
<212> TYPE: DNA
<213> ORGANISM: Artificial
<220> FEATURE:
<223> OTHER INFORMATION: Primer for mutant hTLR3

<400> SEQUENCE: 92
gcgaatttaa tcacattaga tctg                                    24

<210> SEQ ID NO 93
<211> LENGTH: 27
<212> TYPE: DNA
<213> ORGANISM: Artificial
<220> FEATURE:
<223> OTHER INFORMATION: Primer for mutant hTLR3

<400> SEQUENCE: 93
agttcctaat gctgtagatg acaagcc                                 27

<210> SEQ ID NO 94
<211> LENGTH: 24
<212> TYPE: DNA
<213> ORGANISM: Artificial
<220> FEATURE:
<223> OTHER INFORMATION: Primer for mutant hTLR3

<400> SEQUENCE: 94
acagcattag gaactcaggt tcag                                    24

<210> SEQ ID NO 95
<211> LENGTH: 32
<212> TYPE: DNA
<213> ORGANISM: Artificial
<220> FEATURE:
<223> OTHER INFORMATION: Primer for mutant hTLR3

<400> SEQUENCE: 95
ttccagctga accccagttc taattttgt ag                            32

<210> SEQ ID NO 96
<211> LENGTH: 22
<212> TYPE: DNA
<213> ORGANISM: Artificial
<220> FEATURE:
<223> OTHER INFORMATION: Primer for mutant hTLR3

<400> SEQUENCE: 96
ggggttcagc tggaaaatct cc                                      22

<210> SEQ ID NO 97
<211> LENGTH: 36
<212> TYPE: DNA
<213> ORGANISM: Artificial
<220> FEATURE:
<223> OTHER INFORMATION: Primer for mutant hTLR3

<400> SEQUENCE: 97
acttcgtagc gctagaattt tattgtttga taatag                       36

<210> SEQ ID NO 98
<211> LENGTH: 30
<212> TYPE: DNA
<213> ORGANISM: Artificial

<220> FEATURE:
<223> OTHER INFORMATION: Primer for mutant hTLR3

<400> SEQUENCE: 98
ctagcgctac gaagtgaaga actggatatc      30

<210> SEQ ID NO 99
<211> LENGTH: 36
<212> TYPE: DNA
<213> ORGANISM: Artificial
<220> FEATURE:
<223> OTHER INFORMATION: Primer for mutant hTLR3

<400> SEQUENCE: 99
actttgtagc gctagaattt tattgtttga taatag      36

<210> SEQ ID NO 100
<211> LENGTH: 30
<212> TYPE: DNA
<213> ORGANISM: Artificial
<220> FEATURE:
<223> OTHER INFORMATION: Primer for mutant hTLR3

<400> SEQUENCE: 100
ctagcgctac aaagtgaaga actggatatc      30

<210> SEQ ID NO 101
<211> LENGTH: 35
<212> TYPE: DNA
<213> ORGANISM: Artificial
<220> FEATURE:
<223> OTHER INFORMATION: Primer for mutant hTLR3

<400> SEQUENCE: 101
attgccaaag atctccagtt cttcactttt tagcg      35

<210> SEQ ID NO 102
<211> LENGTH: 30
<212> TYPE: DNA
<213> ORGANISM: Artificial
<220> FEATURE:
<223> OTHER INFORMATION: Primer for mutant hTLR3

<400> SEQUENCE: 102
gagatctttg gcaattcatc tttaaaaaaa      30

<210> SEQ ID NO 103
<211> LENGTH: 28
<212> TYPE: DNA
<213> ORGANISM: Artificial
<220> FEATURE:
<223> OTHER INFORMATION: Primer for mutant hTLR3

<400> SEQUENCE: 103
ctctttaagt ggattcgatg acaactct      28

<210> SEQ ID NO 104
<211> LENGTH: 25
<212> TYPE: DNA
<213> ORGANISM: Artificial
<220> FEATURE:
<223> OTHER INFORMATION: Primer for mutant hTLR3

<400> SEQUENCE: 104
aatccactta aagagttttc tccag      25

<210> SEQ ID NO 105
<211> LENGTH: 36
<212> TYPE: DNA
<213> ORGANISM: Artificial
<220> FEATURE:
<223> OTHER INFORMATION: Primer for mutant hTLR3

<400> SEQUENCE: 105
tcttccaatt gcctgaaaac accctggaga aaactc         36

<210> SEQ ID NO 106
<211> LENGTH: 23
<212> TYPE: DNA
<213> ORGANISM: Artificial
<220> FEATURE:
<223> OTHER INFORMATION: Primer for mutant hTLR3

<400> SEQUENCE: 106
caggcaattg gaagattatt tgg         23

<210> SEQ ID NO 107
<211> LENGTH: 36
<212> TYPE: DNA
<213> ORGANISM: Artificial
<220> FEATURE:
<223> OTHER INFORMATION: Primer for mutant hTLR3

<400> SEQUENCE: 107
tcttccaatt gtgtgaaaac accctggaga aaactc         36

<210> SEQ ID NO 108
<211> LENGTH: 23
<212> TYPE: DNA
<213> ORGANISM: Artificial
<220> FEATURE:
<223> OTHER INFORMATION: Primer for mutant hTLR3

<400> SEQUENCE: 108
cacacaattg gaagattatt tgg         23

<210> SEQ ID NO 109
<211> LENGTH: 30
<212> TYPE: DNA
<213> ORGANISM: Artificial
<220> FEATURE:
<223> OTHER INFORMATION: Primer for mutant hTLR3

<400> SEQUENCE: 109
aaggtgggga ttcagctgga cattgttcag         30

<210> SEQ ID NO 110
<211> LENGTH: 33
<212> TYPE: DNA
<213> ORGANISM: Artificial
<220> FEATURE:
<223> OTHER INFORMATION: Primer for mutant hTLR3

<400> SEQUENCE: 110
ctgaatcccc accttacaga gaagctatgt ttg         33

<210> SEQ ID NO 111
<211> LENGTH: 34
<212> TYPE: DNA
<213> ORGANISM: Artificial
<220> FEATURE:
<223> OTHER INFORMATION: Primer for mutant hTLR3

<400> SEQUENCE: 111
gtttgataat tcccaacata gcttctctgt aagg                                      34

<210> SEQ ID NO 112
<211> LENGTH: 33
<212> TYPE: DNA
<213> ORGANISM: Artificial
<220> FEATURE:
<223> OTHER INFORMATION: Primer for mutant hTLR3

<400> SEQUENCE: 112
tgggaattat caaacacaag cattcggaat ctg                                       33

<210> SEQ ID NO 113
<211> LENGTH: 36
<212> TYPE: DNA
<213> ORGANISM: artificial
<220> FEATURE:
<223> OTHER INFORMATION: Primer

<400> SEQUENCE: 113
tgcaattgac tggattgagt tggacatgag atggag                                    36

<210> SEQ ID NO 114
<211> LENGTH: 36
<212> TYPE: DNA
<213> ORGANISM: artificial
<220> FEATURE:
<223> OTHER INFORMATION: Primer

<400> SEQUENCE: 114
atccagtcaa ttgcaaataa tccctttgtc aagcag                                    36

<210> SEQ ID NO 115
<211> LENGTH: 66
<212> TYPE: DNA
<213> ORGANISM: Artificial
<220> FEATURE:
<223> OTHER INFORMATION: Primer for mutant hTLR3

<400> SEQUENCE: 115
aaggtaagcc tatccctaac cctctcctcg gtctcgattc tacgaagtgc actgttagcc          60
atgaag                                                                     66

<210> SEQ ID NO 116
<211> LENGTH: 35
<212> TYPE: DNA
<213> ORGANISM: Artificial
<220> FEATURE:
<223> OTHER INFORMATION: Primer for mutant hTLR3

<400> SEQUENCE: 116
aagcggccgc ttagttatta ctgttgacat ggtcg                                     35

<210> SEQ ID NO 117
<211> LENGTH: 106
<212> TYPE: DNA
<213> ORGANISM: Artificial
<220> FEATURE:
<223> OTHER INFORMATION: Primer for hTLR3

<400> SEQUENCE: 117
aagctagcat gagacagact ttgccttgta tctacttttg ggggggcctt ttgccctttg          60

```
ggatgctgtg tgcatcctcc accaccggta agcctatccc taaccc                    106

<210> SEQ ID NO 118
<211> LENGTH: 35
<212> TYPE: DNA
<213> ORGANISM: Artificial
<220> FEATURE:
<223> OTHER INFORMATION: Primer for hTLR3

<400> SEQUENCE: 118
aagcggccgc ttagttatta ctgttgacat ggtcg                                35

<210> SEQ ID NO 119
<211> LENGTH: 22
<212> TYPE: DNA
<213> ORGANISM: Artificial
<220> FEATURE:
<223> OTHER INFORMATION: Primer for mutant hTLR3

<400> SEQUENCE: 119
tagctcattg tgctggaggt tc                                              22

<210> SEQ ID NO 120
<211> LENGTH: 20
<212> TYPE: DNA
<213> ORGANISM: Artificial
<220> FEATURE:
<223> OTHER INFORMATION: Primer for mutant hTLR3

<400> SEQUENCE: 120
aaaacctttg ccttctgcac                                                 20

<210> SEQ ID NO 121
<211> LENGTH: 36
<212> TYPE: DNA
<213> ORGANISM: Artificial
<220> FEATURE:
<223> OTHER INFORMATION: Primer for mutant hTLR3

<400> SEQUENCE: 121
acccaagctg gctagcatga gacagacttt gccttg                               36

<210> SEQ ID NO 122
<211> LENGTH: 39
<212> TYPE: DNA
<213> ORGANISM: Artificial
<220> FEATURE:
<223> OTHER INFORMATION: Primer for mutant hTLR3

<400> SEQUENCE: 122
agcacagtgg cggccgctta gttattactg ttgacatgg                            39
```

TLR3 BINDING AGENTS

CROSS-REFERENCE TO RELATED APPLICATIONS

This application is the U.S. National Phase of Application No. PCT/EP2013/061173 entitled "TRL3 BINDING AGENTS" filed May 30, 2013, which designated the United States, and which claims the benefit of U.S. Provisional Application Nos. 61/653,652 filed 31 May 2012, 61/670,289 filed 11 Jul. 2012 and 61/679,923 filed 6 Aug. 2012; all of which are incorporated herein by referenced in their entirety; including any drawings.

REFERENCE TO SEQUENCE LISTING

The present application is being filed along with a Sequence Listing in electronic format. The Sequence Listing is provided as a file entitled "PCT Seq list TLR3-4_ST25", created May 29, 2013, which is 46 KB in size. The information in the electronic format of the Sequence Listing is incorporated herein by reference in its entirety.

FIELD OF THE INVENTION

The present invention relates to antibodies (e.g. monoclonal antibodies), antibody fragments, and derivatives thereof that bind and inhibit TLR3 signaling. The invention also relates to cells producing such antibodies; methods of making such antibodies; fragments, variants, and derivatives of the antibodies; pharmaceutical compositions comprising the same; methods of using the antibodies to diagnose, treat or prevent diseases, e.g. autoimmune diseases, inflammatory diseases and the like.

BACKGROUND

*Drosophila* toll proteins control dorsal-ventral patterning and are thought to represent an ancient host defense mechanism. In humans, TLRs are believed to be an important component of innate immunity. Human and *Drosophila* Toll protein sequences show homology over the entire length of the protein chains. The family of human Toll-like receptors is comprised of ten highly conserved receptor proteins, TLR1-TLR10. Like *Drosophila* toll, human TLRs are type I transmembrane proteins with an extracellular domain consisting of a leucine-rich repeat (LRR) domain that recognizes pathogen-associated molecular patterns (PAMPs), and a cytoplasmic domain that is homologous to the cytoplasmic domain of the human interleukin-1 (IL-1) receptor. Similar to the signaling pathways for both *Drosophila* toll and the IL-1 receptor, human Toll-like receptors signal through the NF-κB pathway.

Although the different mammalian TLRs share many characteristics and signal transduction mechanisms, their biological functions are very different. This is due in part to the fact that four different adaptor molecules (MyD88, TIRAP, TRIF and TRAF) are associated in various combinations with the TLRs and mediate different signaling pathways. In addition, different ligands for one TLR may preferentially activate different signal transduction pathways. Furthermore, the TLRs are differentially expressed in various hematopoietic and non-hematopoietic cells. Accordingly, the response to a TLR ligand depends not only on the signal pathway activated by the TLR, but also on the nature of the cells in which the individual TLR is expressed.

Toll-like receptor 3 (TLR3) has received considerable attention as a therapeutic target as TLR3 signaling has been implicated in inflammatory and autoimmune conditions. Patent application WO98/50547 provides the nucleic acid and amino acid sequence of the hTLR3 protein. De Bouteiller et al. (2005) J. Biol. Chem. 280(46): 38133-38145) disclose use of an anti-TLR3 antibody to bind cell surface TLR3. Antibody C1130 is stated to be activatory toward TLR3 and has been described in WO 2007/051164. Polyclonal antibodies that inhibited TLR3 were described in Cavassani et al. (2008) J. Exp. Med. 205: 2609-2621. WO 03/106499 and Matsumoto et al. (2003) J. Immunol. 171: 3154-3162 describes an antibody corresponding to antibody clone TLR3.7 (eBioScience Inc., San Diego) reported to bind and inhibit cell surface TLR3 but not cell compartment TLR3 or in myeloid-lineage DC. WO 06/060513 describes an antibody C1068 which is reported to inhibit cytokine production in epithelial cells, which are reported to express TLR3 on the cell surface. PCT patent application WO2010/051470 provides further anti-TLR3 antibodies. Other anti-TLR3 antibodies for research use include polyclonal anti-TLR3 antibodies from R&D Systems Corp., antibody 40C1285 from Abcam and antibodies 619F7, 713E4, 716G10, IMG-5631 and -IMG-5348, all from Imgenex Corp.

However, among currently available anti-TLR3 antibodies, they are not optimally suited for use as therapeutic agents, e.g. to modulate TLR3 in vivo. For example, many suffer from lack of efficacy or affinity to their epitopes. There is therefore a need to provide improved antibodies directed to TLR3.

SUMMARY OF THE INVENTION

The present invention arises from the discovery of novel compositions comprising, and methods of using monoclonal antibodies, including but not limited to antibody fragments, and derivatives that specifically bind to and inhibit the function of human TLR3.

The present invention provides antibodies with new properties useful for targeting TLR3 in vivo. Since TLR3 binds its natural ligand (dsRNA) and signals exclusively in the endosome in macrophages and dendritic cells (DCs) (at acidic pH), antibodies have previously been selected based on high affinity at endosomal pH where signalling occurs. However, little remains known about the mechanism by which anti-TLR3 antibodies enter cells. The present invention provides antibodies that have strong binding to TLR3 exposed at the cell surface and in a pH neutral environment and which display improved potency in TLR3 inhibition. Optimizing binding of cell-surface expressed TLR3 may therefore be an important criteria for cellular (endosomal) uptake by a cell which may condition downstream (or overall) biological activity. The present antibodies show strong binding to human cell surface TLR3, as observed in an assay where TLR3 is expressed exclusively at the cell surface in neutral pH conditions. In this way, antibodies having improved cell surface binding were selected. The inhibitory activity of anti-TLR3 antibodies may therefore be governed by the cycling back to the cell surface of the endosomal TLR3 polypeptides involved in endocytosis once the receptors separated from their ligands.

In one aspect the invention provides an antibody that inhibits TLR3-mediated signalling in a TLR3-expressing cell, wherein the antibody specifically binds a human TLR3 polypeptide expressed solely at the surface of a cell, optionally at neutral pH. Optionally, the antibody has an $EC_{50}$ of no more than 0.3 µg/ml, optionally no more than 0.2 µg/ml, optionally no more than 0.1 µg/ml, for binding to cells expressing TLR3 solely at the cell surface.

In one aspect the invention provides antibodies that bind the N-terminal portion of the TLR3 protein at least partly (or primarily or exclusively) on the glycan-free lateral surface of the TLR3 polypeptide (the face bound by dsRNA), and optionally furthermore at least partly within the N-terminal dsRNA binding site of a human TLR3 polypeptide. Optionally, the antibody further binds TLR3 at least partly within the backbone of the N-terminal portion of the TLR3 polypeptide.

While some previous epitopes on TLR3 have been shown to be useful for efficacious inhibition of TLR3, epitopes have not necessarily remained present in non-human primates. In one aspect the invention provides antibodies that inhibit TLR3 polypeptide activity by binding to the N-terminal portion of a human TLR3 protein, and that also bind non-human primate TLR3. In one aspect the invention provides antibodies that bind the N-terminal portion of the TLR3 protein and that do not compete with dsRNA for binding to human TLR3, wherein the antibodies also bind to a of non-human primate TLR3 polypeptide (in a non-human primate-TLR3-expressing cell). In one aspect the invention provides antibodies that bind the N-terminal portion of the TLR3 protein and that competes with dsRNA for binding to the N-terminal dsRNA binding site of a human TLR3 polypeptide, wherein the antibodies also bind to a non-human primate TLR3 polypeptide (in a non-human primate-TLR3-expressing cell). In one embodiment, the antibodies at least partly (or primarily or exclusively) on the glycan-free lateral surface of the TLR3 polypeptide (the face bound by dsRNA). In one embodiment, the antibodies bind to TLR3 at least partly within the N-terminal dsRNA binding site of a human TLR3 polypeptide. In one embodiment, the non-human primate is *macaca fascicularis*. In one embodiment, the non-human primate TLR3 polypeptide comprises an amino acid sequence shown in NCBI accession number BAG55033 (SEQ ID NO: 2).

In one aspect the invention provides antibodies that bind to the N-terminal portion of a human TLR3 protein, notably within residues 41 to 251, optionally at least partly within residues 41 to 139, 41 to 120 or residues 41 to 89, of human TLR3 of SEQ ID NO: 1.

In one aspect the invention provides antibodies that bind to the N-terminal portion of a human TLR3 protein, wherein the antibody has reduced binding to a TLR3 polypeptide having a mutation in its N-terminal portion in the segment corresponding to residues 41-139 of SEQ ID NO: 1, relative to binding between the antibody and a wild-type TLR3 polypeptide of SEQ ID NO: 1.

Optionally, the antibodies of the invention interfere with binding of dsRNA to the N-terminal dsRNA binding site of a human TLR3 polypeptide. Optionally, the antibodies bind one or more amino acid residues within the glycan-free lateral surface of the TLR3 polypeptide that is involved in binding of the TLR3 polypeptide to dsRNA, and/or residues adjacent thereto.

Optionally, the antibodies bind an epitope comprising residues 64 and/or residue 65 of SEQ ID NO: 1, and/or have reduced binding to a TLR3 polypeptide having a mutation at residues 64 and/or residue 65 of SEQ ID NO: 1. Optionally, the antibodies bind an epitope comprising residues 86 and/or residue 89 of SEQ ID NO: 1, and/or have reduced binding to a TLR3 polypeptide having a mutation at residues 86 and/or residue 89 of SEQ ID NO: 1. Optionally, the antibodies bind an epitope comprising residues 117 and/or residue 120 of SEQ ID NO: 1, and/or have reduced binding to a TLR3 polypeptide having a mutation at residues 117 and/or residue 120 of SEQ ID NO: 1. Optionally, the antibodies bind an epitope comprising residues 137 and/or residue 139 of SEQ ID NO: 1, and/or have reduced binding to a TLR3 polypeptide having a mutation at residues 137 and/or residue 139 of SEQ ID NO: 1. Optionally, the antibodies bind an epitope comprising residues 112, 113 and/or 115 of SEQ ID NO: 1, and/or have reduced binding to a TLR3 polypeptide having a mutation at residues 112, 113 and/or 115 of SEQ ID NO: 1.

In one embodiment, the antibodies have reduced binding to a TLR3 polypeptide having a mutation at residues 117 and/or residue 120 of SEQ ID NO: 1, and reduced binding to a TLR3 polypeptide having a mutation at residues 137 and/or residue 139 of SEQ ID NO: 1. Optionally, the antibodies have reduced binding to a TLR3 polypeptide having a mutation at residues 117 and/or residue 120 of SEQ ID NO: 1, and do not have reduced binding to a TLR3 polypeptide having a mutation at residues 137 and/or residue 139 of SEQ ID NO: 1.

In one embodiment, the antibodies have reduced binding to a TLR3 polypeptide having a mutation at residues 64 and/or residue 65 of SEQ ID NO: 1, and reduced binding to a TLR3 polypeptide having a mutation at residues 137 and/or residue 139 of SEQ ID NO: 1. Optionally, the antibodies have reduced binding to a TLR3 polypeptide having a mutation at residues 86 and/or residue 89 of SEQ ID NO: 1. and reduced binding to a TLR3 polypeptide having a mutation at residues 137 and/or residue 139 of SEQ ID NO: 1. Optionally, the antibodies do not have reduced binding to a TLR3 polypeptide having a mutation at residues 117 and/or residue 120 of SEQ ID NO: 1. Optionally, the antibodies do not have reduced binding to a TLR3 polypeptide having a mutation at residues 112, 113 and/or 115 of SEQ ID NO: 1.

Optionally, the antibodies have reduced binding to a TLR3 polypeptide having a mutation at residues 64 and/or residue 65 of SEQ ID NO: 1, a TLR3 polypeptide having a mutation at residues 86 and/or residue 89 of SEQ ID NO: 1 and a TLR3 polypeptide having a mutation at residues 137 and residue 139 of SEQ ID NO: 1. As evidenced by binding to TLR3 mutants, the antibodies differ in their epitope from previously described antibodies.

In one embodiment, the antibodies have reduced binding to a TLR3 polypeptide having a mutation at residues 112, 113 and/or 115 of SEQ ID NO: 1, and reduced binding to a TLR3 polypeptide having a mutation at residues 137 and/or residue 139 of SEQ ID NO: 1. In one embodiment, the antibodies have reduced binding to a TLR3 polypeptide having a mutation at residues 112, 113 and/or 115 of SEQ ID NO: 1, and reduced binding to a TLR3 polypeptide having a mutation at residues 117 and/or residue 120 of SEQ ID NO: 1. In one embodiment, the antibodies have reduced binding to a TLR3 polypeptide having a mutation at residues 112, 113 and/or 115 of SEQ ID NO: 1, reduced binding to a TLR3 polypeptide having a mutation at residues 117 and/or residue 120 of SEQ ID NO: 1, and reduced binding to a TLR3 polypeptide having a mutation at residues 137 and/or residue 139 of SEQ ID NO: 1. In one embodiment, the antibodies have reduced binding to a TLR3 polypeptide having a mutation at residues 112 and/or 113 of SEQ ID NO: 1, and reduced binding to a TLR3 polypeptide having a mutation at residue 137 of SEQ ID NO: 1. Optionally, the antibodies do not have reduced binding to a TLR3 polypeptide having a mutation at residues 86 and/or residue 89 of SEQ ID NO: 1. Optionally, the antibodies do not have reduced binding to a TLR3 polypeptide having a mutation at residues 64 and/or residue 65 of SEQ ID NO: 1.

Optionally, in any of the embodiments herein, the antibodies maintain binding (do not have reduced binding) to a TLR3 polypeptide having a mutation at residues 116, 145, 182, 196 and/or residue 171 of SEQ ID NO: 1.

In one aspect, the invention provides antibodies that interfere with binding of dsRNA to a human TLR3 polypeptide. In one aspect, the invention provides antibodies that interfere with binding of dsRNA to the N-terminal dsRNA binding site of a human TLR3 polypeptide. Optionally, the antibodies compete with dsRNA for binding to human TLR3 polypeptide, e.g, to the N-terminal dsRNA binding site of a human TLR3 polypeptide. Competition can be assessed using standard methods, e.g. Biacore assays to assess whether antibodies bind to immobilized TLR3 in the presence of dsRNA, and/or whether dsRNA binds to immobilized TLR3 in the presence of antibodies, under acidic conditions.

Optionally, the antibodies compete with dsRNA for binding to human TLR3 polypeptide in an in vitro assay comprising the steps of: (i) contacting an anti-TLR3 antibody with a TLR3 polypeptide so as to obtain antibodies bound to TLR3 polypeptide, and (ii) contacting the antibody bound TLR3 polypeptide of step (i) with dsRNA and assessing whether dsRNA decreases binding of TLR3 polypeptide (to the antibody, wherein a decrease of binding indicates competition with dsRNA for human TLR3 polypeptide. Optionally, the antibodies compete with dsRNA for binding to human TLR3 polypeptide in an in vitro assay comprising the steps of: (i) contacting a TLR3 polypeptide with dsRNA so as to obtain dsRNA bound to TLR3 polypeptide, and (ii) contacting the dsRNA bound TLR3 polypeptide of step (i) with an anti-TLR3 antibody and assessing whether the TLR3 polypeptide binds the dsRNA-TLR3 polypeptide complex, wherein lack of substantial binding indicates competition with dsRNA for human TLR3 polypeptide. Optionally, the antibodies compete with dsRNA for binding to human TLR3 polypeptide in an in vitro assay comprising the steps of: (i) attaching an anti-TLR3 antibody to a solid support (e.g., via a constant domain), (ii) contacting said antibody with a TLR3 polypeptide so as to obtain antibodies bound to TLR3 polypeptide, and (iii) contacting the antibody bound TLR3 polypeptide of step (ii) with dsRNA and assessing whether dsRNA decreases binding of TLR3 polypeptide to the antibody, wherein a decrease of binding indicates competition with dsRNA for human TLR3 polypeptide.

In one aspect of any of the embodiments of the invention, the antibody binds to a human TLR3 polypeptide expressed at the surface of a cell, optionally as assessed in a cell expressing TLR3 exclusively at the cell surface under neutral pH, internalizes into a cell that expresses TLR3, and inhibits TLR3 signaling in a cell (e.g. a TLR3-expressing human dendritic cell).

In one aspect, the antibodies bind human TLR3 polypeptides under neutral conditions, and in particular under conditions representative of that encountered in the cell cytosol. Such neutral conditions are generally characterized by a pH between 6.6 and 7.4, for example a slightly alkaline pH of 7.2 found in the cell cytosol. Optionally, the antibody has a $K_D$ of no more than $10^{-9}$ M, optionally less than $10^{-10}$ M, optionally less than $10^{-11}$ M for binding to a TLR3 polypeptide at neutral pH. Optionally, the binding at neutral conditions is of better affinity than under acid conditions, e.g. where the $K_D$ for binding to TLR3 at neutral compared to acidic conditions is lower by at least 0.5-, 1.0-, 1.5- or 2.0-$\log_{10}$.

The present invention further provides specific antibodies have increased activity over previously reported antibodies. In one aspect of any of the embodiments of the invention, the antibody competes for binding to a TLR3 polypeptide (e.g. a human TLR3 polypeptide comprising an amino acid sequence of SEQ ID NO: 1) with any one or any combination of monoclonal antibody 11E1, 7G11, 31F6, 32C4 and 37B7, optionally under acid and/or neutral conditions. In one embodiment, an antibody of the invention competes for binding to a TLR3 polypeptide, optionally under acid and/or neutral conditions, with an antibody having respectively a VH and VL region of SEQ ID NOS: 3 and 4 (11E1), a VH and VL region of SEQ ID NOS: 14 and 15 (31F6), a VH and VL region of SEQ ID NOS: 25 and 26 (32C4), a VH and VL region of SEQ ID NOS: 36 and 37 (37B7) or a VH and VL region of SEQ ID NOS: 47 and 48 (7G11). In one aspect of any of the embodiments of the invention, the antibody may have a heavy and/or light chain having one, two or three CDRs of antibody 11E1, 7G11, 31F6, 32C4 or 37B7.

In one aspect, the antibody that specifically binds TLR3 has one or more (including any combination thereof, or all of) of the following properties:
 a. binds to a TLR3 polypeptide comprising an amino acid sequence of SEQ ID NO: 1 and/or 2;
 b. specifically binds a human TLR3 polypeptide expressed solely at the surface of a cell, wherein the antibody has an $EC_{50}$ of no more than 0.3 µg/ml, optionally no more than 0.2 µg/ml, optionally no more than 0.1 µg/ml, for binding to cells expressing TLR3 solely at the cell surface;
 c. internalizes into a cell that expresses TLR3 on its surface;
 d. has a subnanomolar affinity for a TLR3 polypeptide at an neutral pH, e.g. a pH of about pH 7.2;
 e. has a subnanomolar affinity for a TLR3 polypeptide at an acidic pH, e.g. a pH less than about 6.5, or between about 4.5 to 6.5 or about pH 5.6;
 f. inhibits TLR3 signaling in the presence of a TLR3 ligand;
 g. inhibits TLR3 signaling in an inflammatory background, e.g. in the presence of inflammatory cytokines such as IFNα;
 h. competes for binding to a TLR3 polypeptide with antibody 11E1, 7G11, 31F6, 32C4 or 37B7;
 i. competes with dsRNA for binding to the N-terminal portion the TLR3 polypeptide;
 j. has reduced binding to a TLR3 polypeptide having a mutation at residues 64 and/or residue 65 of SEQ ID NO: 1, and/or reduced binding to a TLR3 polypeptide having a mutation at residues 86 and/or residue 89 of SEQ ID NO: 1;
 k. has reduced binding to a TLR3 polypeptide having a mutation at residues 117 and/or residue 120 of SEQ ID NO: 1, and/or has reduced binding to a TLR3 polypeptide having a mutation at residues 137 and/or residue 139 of SEQ ID NO: 1, and/or has reduced binding to a TLR3 polypeptide having a mutation at residues 112, 113 and/or 115 of SEQ ID NO: 1; and/or
 l. binds to at least one, two, three, four, five, six, seven or more residues in the segment corresponding to residues 41-251, 41-89, 41-120 or 41-139 of the TLR3 polypeptide of SEQ ID NO: 1.

In one aspect, the invention provides a monoclonal antibody that specifically binds to at least one, two, three, four, five, six, seven or more residues in the segment corresponding to residues 1-251, optionally 41-251, 41-89, 41-120 or 41-139 of the TLR3 polypeptide of SEQ ID NO: 1. Optionally, the antibody inhibits signaling by the TLR3 polypeptide. Optionally, the antibody does not bind residue 116, residue 145 and/or residue 182 of the TLR3 polypeptide of SEQ ID NO: 1. Optionally, the antibody does not bind residue 171, and/or residue 196 of the TLR3 polypeptide of SEQ ID NO: 1. Optionally, binding of the antibody to a TLR3 polypeptide having a mutation at residues 116, 145, 182 196 and/or residue 171 of the TLR3 polypeptide of SEQ ID NO: 1 is maintained (i.e., is not substantially reduced), in comparison to binding to a wild-type TLR3 polypeptide of SEQ ID NO: 1; preferably said mutation is a K145E, D116R, K182E, N196A and/or E171A mutation. Such antibodies can optionally further have any properties described herein, e.g. subnanomolar affinity for a TLR3 polypeptide at an acidic pH, inhibits TLR3 signaling in the presence of a TLR3 ligand or in an inflammatory background (e.g. in the presence of inflammatory cytokines such as IFNα), competes for binding to a TLR3 polypeptide with 11E1, 7G11, 31F6, 32C4 or 37B7; does not compete with dsRNA for binding to C-terminal portion the TLR3 polypeptide; or inhibits IP-10 secretion on DC (e.g. in human myeloid DC). Such antibodies can furthermore be used in any of the methods of the invention.

In one embodiment, the invention provides an antibody that binds a TLR3 polypeptide, wherein the antibody comprises (i) the heavy chain CDR 1, 2 and 3 (HCDR1, HCDR2, HCDR3) amino acid sequences as shown in SEQ ID NO: 5, 6 or 7 (HCDR1), 8 or 9 (HCDR2) and 10 (HCDR3), and (ii) the light chain CDR 1, 2 and 3 (LCDR1, LCDR2, LCDR3) amino acid sequences as shown in SEQ ID NO: 11, 12 and 13, respectively; wherein one, two, three, four, or five or more of the amino acids in any of said sequences may be substituted by a different amino acid. In one embodiment, the antibody comprises (i) the heavy chain CDR 1, 2 and 3 (HCDR1, HCDR2, HCDR3) amino acid sequences as shown in SEQ ID NO: 16, 17 or 18 (HCDR1), 19 or 20 (HCDR2) and 21 (HCDR3), and (ii) the light chain CDR 1, 2 and 3 (LCDR1, LCDR2, LCDR3) amino acid sequences as shown in SEQ ID NO: 22, 23 and 24, respectively; wherein one, two, three, four, or five or more of the amino acids in any of said sequences may be substituted by a different amino acid. In one embodiment, the antibody comprises (i) the heavy chain CDR 1, 2 and 3 (HCDR1, HCDR2, HCDR3) amino acid sequences as shown in SEQ ID NO: 27, 28 or 29 (HCDR1), 30 or 31(HCDR2) and 32 (HCDR3), and (ii) the light chain CDR 1, 2 and 3 (LCDR1, LCDR2, LCDR3) amino acid sequences as shown in SEQ ID NO: 33, 34 and 35, respectively; wherein one, two, three, four, or five or more of the amino acids in any of said sequences may be substituted by a different amino acid. In one embodiment, the antibody comprises (i) the heavy chain CDR 1, 2 and 3 (HCDR1, HCDR2, HCDR3) amino acid sequences as shown in SEQ ID NO: 38, 39 or 40 (HCDR1), 41 or 42 (HCDR2) and 43 (HCDR3), and (ii) the light chain CDR 1, 2 and 3 (LCDR1, LCDR2, LCDR3) amino acid sequences as shown in SEQ ID NO: 44, 45 and 46, respectively; wherein one, two, three, four, or five or more of the amino acids in any of said sequences may be substituted by a different amino acid. In one embodiment, the antibody comprises (i) the heavy chain CDR 1, 2 and 3 (HCDR1, HCDR2, HCDR3) amino acid sequences as shown in SEQ ID NO: 49, 50 or 51 (HCDR1), 52 or 53 (HCDR2) and 54 (HCDR3), and (ii) the light chain CDR 1, 2 and 3 (LCDR1, LCDR2, LCDR3) amino acid sequences as shown in SEQ ID NO: 55, 56 and 57, respectively; wherein one, two, three, four, or five or more of the amino acids in any of said sequences may be substituted by a different amino acid.

In another embodiment, the antibody of any of the embodiments herein is capable of being internalized by a cell that expresses TLR3 polypeptide on its surface.

In one embodiment, the antibody is chimeric, e.g. contains a non-murine, optionally a human, constant region. In one embodiment, the antibody is human or humanized. In another embodiment, the antibody is a mouse or rat antibody (e.g., comprises CDRs derived from a rat or rat gene or rat Ig locus gene segment). In another embodiment, the antibody does not substantially bind to other human TLRs (e.g. TLR4).

In one aspect of any of the embodiments of the invention, the isotype of the antibody is IgG, optionally IgG1 or IgG3. In one embodiment the antibody comprises an Fc domain or is of an isotype that is bound by FcγR.

In one aspect of any of the embodiments of the invention, the antibody is an antibody fragment selected from Fab, Fab', Fab'-SH, F(ab')2, Fv, diabodies, single-chain antibody fragment, or a multispecific antibody comprising multiple different antibody fragments. In one aspect of any of the embodiments of the invention, the antibody does not comprise an Fc domain or is of an isotype that is not substantially bound by FcγR (e.g. human CD16). In one embodiment, the antibody is of human IgG4 or IgG2 isotype. Human IgG4 isotypes or other IgG isotypes modified to reduce their FcγR binding can be used for their advantageous pharmacological properties such as serum half-life, while modulating TLR3 signaling, in e.g. a DC, without inducing the death of the cell. In one aspect of any of the embodiments of the invention, the anti-TLR3 antibody inhibits TLR3 signaling and comprises a constant region of human IgG4 or IgG2 isotype. In one aspect, of any of the embodiments of the invention, the anti-TLR3 antibody inhibits TLR3 signaling and comprises a constant region (heavy chain constant region) that does not substantially bind FcγRIIIa.

In one preferred embodiment, the anti-TLR3 antibody comprises a heavy chain of human IgG4 isotype. In one embodiment, the anti-TLR3 antibody comprises a human IgG4 heavy chain constant region and comprising a serine to proline mutation in residue 241, corresponding to position 228 according to the EU-index (Kabat et al., "Sequences of proteins of immunological interest", 5$^{th}$ ed., NIH, Bethesda, Md., 1991). Compositions comprising such antibodies can be characterized as having less than about 15%, such as less than about 10% (e.g., about 5% or less, about 4% or less, about 3% or less, or even about 1% or less) of IgG4 "half-antibodies" (comprising a single heavy chain/light chain pair). Such IgG4 "half-antibody" by-products form due to heterogeneity of inter-heavy chain disulfide bridges in the hinge region in a proportion of secreted human IgG4 (see Angal et al., Molecular Immunology, 30(1):105-108, 1993 for a description of IgG4 "half-antibodies", S241P mutation, and related principles). This effect is typically only detectable under denaturing, non-reducing conditions.

In another embodiment, the antibody is conjugated or covalently bound to a detectable or toxic moiety.

In one aspect, the antibodies optionally inhibit TLR3 signaling without blocking binding of a dsRNA TLR3 ligand to the principal (i.e. C-terminal) dsRNA binding site of the TLR3 polypeptide.

In one aspect, the antibodies also bind human TLR3 under acidic conditions, and in particular under conditions representative of that encountered in an acidified subcellular compartment of a cell (e.g. compartments of the endocytic pathway endosomic, lysosomal). Such acidic conditions are generally characterized by a pH lower than about pH 6.5, or between about pH 4.5 to 6.5, or about pH 5.6.

In one aspect of any of the embodiments herein, the antibodies modulate, optionally inhibit, TLR3 signaling in an acidified subcellular compartment of a cell (e.g. compartments of the endocytic pathway endosomic, lysosomal).

In one aspect of any of the embodiments herein, the antibodies modulate, optionally inhibit, TLR3 signaling in a dendritic cell (DC) (e.g. a myeloid DC, monocyte derived DC).

In other aspects of any of the embodiments herein, the antibodies' bivalent binding affinity for TLR3 under neutral and/or acidic conditions can optionally be characterized by a mean $K_D$ of no more than about (i.e. better affinity than) 100, 50, 10, 5, or 1 nanomolar, preferably sub-nanomolar or optionally no more than about 500, 200, 100 or 10 picomolar.

In other aspects of any of the embodiments herein, the antibodies inhibit TLR3 signaling by at least partly (or fully) blocking the binding of a TLR3 ligand to a TLR3 polypeptide. The TLR3 ligand will generally be a ligand other than an anti-TLR3 antibody and may be a naturally occurring or non-naturally occurring TLR3 ligand, optionally a dsRNA-based ligand such as polyAU (polyadenylic acid:polyuridylic acid) or polyIC (polyinosinic:polycytidylic acid).

In another aspect, the invention provides a method of identifying, screening and/or producing an antibody that specifically binds and inhibits a TLR3 polypeptide in a mammalian subject, said method comprising the steps of: a) providing a plurality of antibodies that bind human TLR3 polypeptide, optionally by a method comprising immunizing a non-human mammal with an immunogen comprising a TLR3 polypeptide, and (b) assessing the binding affinity of said antibodies for the TLR3 polypeptide in a cell which expresses human TLR3 solely at the cell surface. Optionally, the method further comprises selecting an antibody from said plurality that has an $EC_{50}$ of no more than 0.3 µg/ml, optionally no more than 0.2 µg/ml, optionally no more than 0.1 µg/ml, for binding to cells expressing human TLR3 solely at the cell surface.

Any of the methods of the invention can further be characterized as comprising any step described in the application, including notably in the "Detailed Description of the Invention"). The invention further relates to an antibody obtainable by any of present methods. The invention further relates to pharmaceutical or diagnostic formulations of the antibodies of the present invention. The invention further relates to methods of using antibodies in methods of treatment or diagnosis, optionally in combination with a second therapeutic agent (e.g. a corticoid, a DMARD, an anti-cytokine or anti-cytokine receptor agent, an anti-TNFalpha agent, etc.).

These and additional advantageous aspects and features of the invention may be further described elsewhere herein.

BRIEF DESCRIPTION OF THE DRAWINGS

FIG. 2F shows a view of the glycan-free lateral surface of the TLR3 polypeptide, with the N-terminal end of the TLR3 polypeptide at the right of the image); FIG. 2G shows a view of the glycan-containing lateral surface of the TLR3 polypeptide and the backbone, with the N-terminal end of the TLR3 polypeptide in the foreground (at the left of the image). FIG. 2H shows a view of the glycan-free lateral surface of the TLR3 polypeptide and the backbone, with the N-terminal end of the TLR3 polypeptide in the foreground (at the right of the image).

FIG. 3 shows results of a rheumatoid arthritis mouse models.

FIG. 4 shows results of the mouse colitis model.

FIG. 5 shows results of a COPD mouse model.

DETAILED DESCRIPTION OF THE INVENTION

Introduction

Figures 1A, 1B, 1C, 1D:
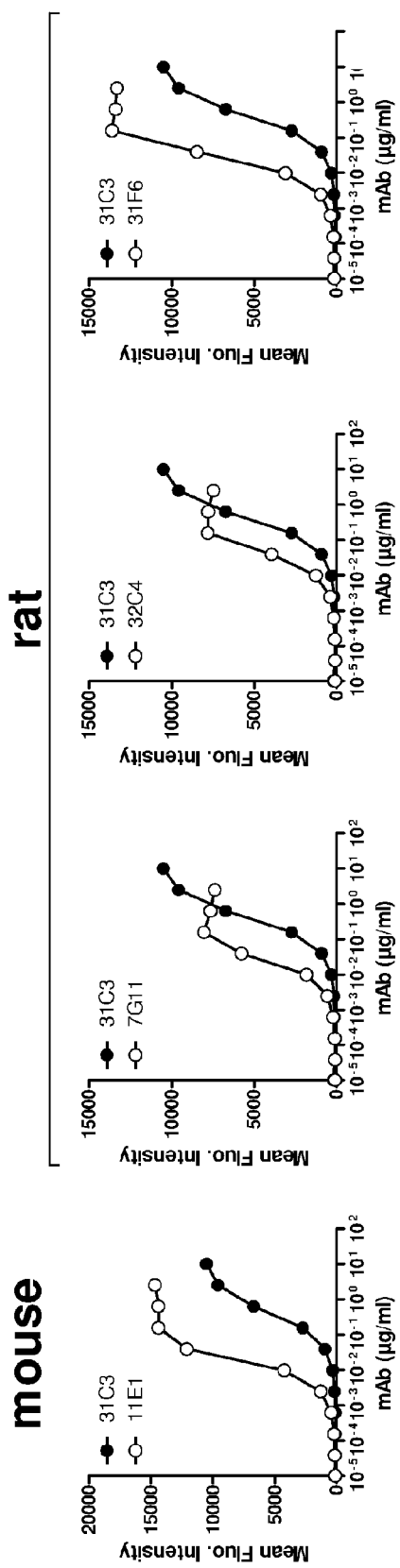
FIGS. 1A, 1B, 1C and 1D show in vitro dose effect for binding to HEK293T cells transiently transfected with a TLR3 ECD construct and expressing TLR3 solely at their surface for antibodies 11E1, 7G11, 32C4 and 31F6, respectively. Each antibody is compared with reference antibody 31C3; binding to cell surface TLR3 is improved for antibodies 11E1, 7G11, 32C4 and 31F6.

The present invention is based, at least in part, on the discovery of high affinity monoclonal antibodies that specifically and efficiently inhibit the TLR3 signaling pathway. The inventors also provide new epitopes present on human TLR3, including the epitope recognized by antibody 11E1, 7G11, 31F6, 32C4 and/or 37B7, which are particularly efficient in inhibiting TLR3 signaling, and inhibiting cytokine release in response to stimulation with a TLR3 ligand.

The antibodies can be used for treating an autoimmune or inflammatory disease in a subject in need thereof. The present invention also provides methods for treating relapses, attacks, or acute phases, occurring during the course of an inflammatory or autoimmune disease in a subject in need thereof using an anti-TLR3 antibody which inhibits TLR3 signaling. The present invention also provides novel methods for treating established inflammatory or autoimmune diseases in a subject in need thereof using an anti-TLR3 antibody which inhibits TLR3 signaling. The invention also provides treatment regimens and treatment combinations that can be used for the treatment of inflammatory or autoimmune disease in a subject in need thereof using an anti-TLR3 antibody which inhibits TLR3 signaling.

The antibodies of the present invention that bind TLR3 under acidic and neutral conditions will generally bind both cell surface TLR3 and endosomic TLR3 at high affinity, such that the antibodies will be useful in any situation (e.g. treatment or prevention of disease) where targeting (e.g. modulating) TLR3 is useful. TLR3 has been found in some cases of inflammation the surface of macrophages and blocking TLR3 upon chloroquine neutralization of endosomal acidification nevertheless exhibited some anti-inflammatory activity (Cavassani et al. 2008, supra). However, the antibodies of the invention will have the greatest advantage over other antibodies in the treatment or prevention of diseases where the modulating (e.g. inhibiting) the signaling by TLR3 in the cytosolic (e.g. endosomic) compartments is useful or required, and the relative importance of modulating signaling of such compartments TLR3 may depend on the disease. One example of such as disease is rheumatoid arthritis; endosomic compartment-expressed TLR3 is believed to play an important role in rheumatoid arthritis, since treatment with chloroquine, an inhibitor of endosomal acidification, inhibits TLR3 signaling and inhibits production of inflammatory cytokines from synovial cultures from patients having rheumatoid arthritis (Sacre et al. (2008) J. Immunol. 181:8002-8009). Endosomal compartment-expressed TLR3 is believed to play an important role in a number of other diseases where DC (e.g. myeloid DC) are involved in exacerbating disease, as mDC have a well-documented capacity to take up antigens from apoptotic or necrotic cells including during tissue necrosis during acute inflammation.

Since the present antibodies are specific for TLR3, they can also be used for other purposes, including purifying TLR3 or TLR3-expressing cells, modulating (e.g. activating or inhibiting) TLR3 receptors in vitro, ex vivo, or in vivo, targeting TLR3-expressing cells for destruction in vivo, or specifically labeling/binding TLR3 in vivo, ex vivo, or in vitro, including for methods such as immunoblotting, IHC analysis, i.e. on frozen biopsies, FACS analysis, and immunoprecipitation.

Definitions

As used herein, "TLR3 ligand" refers to any compound that can specifically bind to and alter the activity of TLR3 in vitro, ex vivo, or in vivo. The compound can be a naturally occurring ligand, e.g., generally dsRNA or viral dsRNA, or a synthetic ligand such as polyIC or polyAU. The compound can be any type of molecule, including inorganic or organic compounds or elements, including proteins (such as antibodies), nucleic acids, carbohydrates, lipids, or any other molecular entity. Further, such compounds can modulate TLR3 receptors in any way, including activating or inhibiting, and by any mechanism, including by binding to the receptor and triggering or shutting off activity in a manner similar to a naturally occurring ligand, or by binding to the receptor and blocking access to other ligands. Preferably, the ligand activates the receptor, and as such can be used to induce the production of cytokines by TLR3-expressing cells.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain (VL) and variable heavy chain (VH) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG and/or IgM are the preferred classes of antibodies employed in this invention, with IgG being particularly preferred, because they are the most common antibodies in the physiological situation and because they are most easily made in a laboratory setting. Preferably the antibody of this invention is a monoclonal antibody. Particularly preferred are humanized, chimeric, human, or otherwise-human-suitable antibodies. "Antibodies" also includes any fragment or derivative of any of the herein described antibodies.

The term "specifically binds to" means that an antibody can bind preferably in a competitive binding assay to the binding partner, e.g. TLR3, as assessed using either recombinant forms of the proteins, epitopes therein, or native proteins present on the surface of isolated target cells. Competitive binding assays and other methods for determining specific binding are further described below and are well known in the art.

When an antibody is said to "compete with" a particular monoclonal antibody (e.g. 11E1, 7G11, 31F6, 32C4 or 37B7) or other TLR3 ligand (e.g., dsRNA, it means that the antibody competes with the monoclonal antibody (or other TLR3 ligand) in a binding assay using either recombinant TLR3 molecules or surface expressed TLR3 molecules. For example, if a test antibody reduces the binding of 11E1, 7G11, 31F6, 32C4 or 37B7 to a TLR3 polypeptide or TLR3-expressing cell in a binding assay, the antibody is said to "compete" respectively with 11E1, 7G11, 31F6, 32C4 or 37B7.

The term "affinity", as used herein, means the strength of the binding of an antibody to an epitope. The affinity of an antibody is given by the dissociation constant $K_D$, defined as $[Ab] \times [Ag]/[Ab-Ag]$, where $[Ab-Ag]$ is the molar concentration of the antibody-antigen complex, $[Ab]$ is the molar concentration of the unbound antibody and $[Ag]$ is the molar concentration of the unbound antigen. The affinity constant Ka is defined by 1/Kd. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of Biacore instruments.

Within the context of this invention a "determinant" designates a site of interaction or binding on a polypeptide.

The term "epitope" is defined as an antigenic determinant, and is the area or region on an antigen to which an antibody binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

By "immunogenic fragment," it is herein meant any polypeptidic or peptidic fragment that is capable of eliciting an immune response such as (i) the generation of antibodies binding said fragment and/or binding any form of the molecule comprising said fragment, including the membrane-bound receptor and mutants derived therefrom, (ii) the stimulation of a T-cell response involving T-cells reacting to the bi-molecular complex comprising any MHC molecule and a peptide derived from said fragment, (iii) the binding of transfected vehicles such as bacteriophages or bacteria expressing genes encoding mammalian immunoglobulins. Alternatively, an immunogenic fragment also refers to any construction capable of eliciting an immune response as defined above, such as a peptidic fragment conjugated to a carrier protein by covalent coupling, a chimeric recombinant polypeptide construct comprising said peptidic fragment in its amino acid sequence, and specifically includes cells transfected with a cDNA of which sequence comprises a portion encoding said fragment.

A "human-suitable" antibody refers to any antibody, derivatized antibody, or antibody fragment that can be safely used in humans for, e.g. the therapeutic methods described herein. Human-suitable antibodies include all types of humanized, chimeric, or fully human antibodies, or any antibodies in which at least a portion of the antibodies is derived from humans or otherwise modified so as to avoid the immune response that is generally provoked when native non-human antibodies are used.

For the purposes of the present invention, a "humanized" or "human" antibody refers to an antibody in which the constant and variable framework region of one or more human immunoglobulins is fused with the binding region, e.g. the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, $5^{th}$ ed., United States Public Health Service, National Institute of Health, Bethesda, Md.).

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

Within the context of this invention, the term antibody that "binds" a common determinant designates an antibody that binds said determinant with specificity and/or affinity.

Producing Anti-TLR3 Antibodies

The antibodies suitable for the method of the invention specifically bind TLR3. Antibodies of the invention furthermore bind TLR3 with high affinity at conditions corresponding to that encountered in at the cell surface. Antibodies of the invention are furthermore capable of inhibiting the TLR3 signaling pathway. The ability of the inhibitory antibodies to specifically inhibit the TLR3 signaling pathway makes them useful for numerous applications, in particular for treating or preventing diseases wherein the inhibition of TLR3 signaling pathway is desirable, i.e. avoid further cytokine and chemokine secretion as well as cellular activation, as described herein.

In one embodiment, the invention provides methods using an antibody that binds human TLR3, and competes for binding to human TLR3 with monoclonal antibody 11E1, 7G11, 31F6, 32C4 or 37B7.

"TLR3", "TLR3 polypeptide" and "TLR3 receptor", used interchangeably, are used herein to refer to Toll-Like Receptor 3, a member of the Toll-like receptor (TLRs) family. The amino acid sequence of human TLR3 is shown in SEQ ID NO: 1 (NCBI accession number NP 003256, the disclosure of which is incorporated herein by reference). The human TLR3 mRNA sequence is described in NCBI accession number NM_003265. Human TLR3 sequences are also described in PCT patent publication no. WO 98/50547, the disclosure of which is incorporated herein by reference. A non-human primate (*macaca fascicularis*) TLR3 amino acid sequence is shown in NCBI accession number BAG55033 (SEQ ID NO: 2).

In one aspect, the invention provides an antibody that competes with monoclonal antibody 11E1, 7G11, 31F6, 32C4 or 37B7 and recognizes, binds to, or has immunospecificity for substantially or essentially the same, or the same, epitope or "epitopic site" on a TLR3 molecule as monoclonal antibody 11E1, 7G11, 31F6, 32C4 or 37B7. In other embodiments, the monoclonal antibody consists of, or is a derivative or fragment of, antibody 11E1, 7G11, 31F6, 32C4 or 37B7.

Any fragment of TLR3, preferably but not exclusively human TLR3, or any combination of TLR3 fragments, can be used as immunogens to raise antibodies, and the antibodies of the invention can recognize epitopes at any location within the TLR3 polypeptide, so long as they can do so on TLR3 expressing cells such as MdDC or MoDC as described herein. In an embodiment, the recognized epitopes are present on the cell surface, i.e. they are accessible to antibodies present outside of the cell. Most preferably, the epitope is the epitope specifically recognized by antibody 11E1, 7G11, 31F6, 32C4 or 37B7. Further, antibodies recognizing distinct epitopes within TLR3 can be used in combination, e.g. to bind to TLR3 polypeptides with maximum efficacy and breadth among different individuals.

The antibodies of this invention may be produced by a variety of techniques known in the art. Typically, they are produced by immunization of a non-human animal, preferably a mouse, with an immunogen comprising a TLR3 polypeptide, preferably a human TLR3 polypeptide. The TLR3 polypeptide may comprise the full length sequence of a human TLR3 polypeptide, or a fragment or derivative thereof, typically an immunogenic fragment, i.e., a portion of the polypeptide comprising an epitope exposed on the surface of cells expressing a TLR3 polypeptide, preferably the epitope recognized by the 11E1, 7G11, 31F6, 32C4 or 37B7 antibody. Such fragments typically contain at least about 7 consecutive amino acids of the mature polypeptide sequence, even more preferably at least about 10 consecutive amino acids thereof. Fragments typically are essentially derived from the extra-cellular domain of the receptor. In a preferred embodiment, the immunogen comprises a wild-type human TLR3 polypeptide in a lipid membrane, typically at the surface of a cell. In a specific embodiment, the immunogen comprises intact cells, particularly intact human cells, optionally treated or lysed. In another preferred embodiment, the polypeptide is a recombinant TLR3 polypeptide.

The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, N.Y. (1988), the entire disclosure of which is herein incorporated by reference). The immunogen is suspended or dissolved in a buffer, optionally with an adjuvant, such as complete or incomplete Freund's adjuvant. Methods for determining the amount of immunogen, types of buffers and amounts of adjuvant are well known to those of skill in the art and are not limiting in any way on the present invention. These parameters may be different for different immunogens, but are easily elucidated.

Similarly, the location and frequency of immunization sufficient to stimulate the production of antibodies is also well known in the art. In a typical immunization protocol, the non-human animals are injected intraperitoneally with antigen on day 1 and again about a week later. This is followed by recall injections of the antigen around day 20, optionally with an adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be used as long as they result in the production of B cells expressing an antibody directed to the antigen used in immunization.

For polyclonal antibody preparation, serum is obtained from an immunized non-human animal and the antibodies present therein isolated by well-known techniques. The serum may be affinity purified using any of the immunogens set forth above linked to a solid support so as to obtain antibodies that react with TLR3 polypeptides.

In an alternate embodiment, lymphocytes from a non-immunized non-human mammal are isolated, grown in vitro, and then exposed to the immunogen in cell culture. The lymphocytes are then harvested and the fusion step described below is carried out.

For preferred monoclonal antibodies, the next step is the isolation of splenocytes from the immunized non-human mammal and the subsequent fusion of those splenocytes with an immortalized cell in order to form an antibody-producing hybridoma. The isolation of splenocytes from a non-human mammal is well-known in the art and typically involves removing the spleen from an anesthetized non-human mammal, cutting it into small pieces and squeezing the splenocytes from the splenic capsule through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the lymphocytes can be fused to an immortal cell line. This is typically a mouse myeloma cell line, although many other immortal cell lines useful for creating hybridomas are known in the art. Preferred murine myeloma lines include, but are not limited to, those derived from MOPC-21 and MPC-11 mouse tumors available from the Salk Institute Cell Distribution Center, San Diego, U.S.A., X63 Ag8653 and SP-2 cells available from the American Type Culture Collection, Rockville, Md. U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Hybridomas are typically grown on a feeder layer of macrophages. The macrophages are preferably from littermates of the non-human mammal used to isolate splenocytes and are typically primed with incomplete Freund's adjuvant or the like several days before plating the hybridomas. Fusion methods are described in Goding, "Monoclonal Antibodies: Principles and Practice," pp. 59-103 (Academic Press, 1986), the disclosure of which is herein incorporated by reference.

The cells are allowed to grow in the selection media for sufficient time for colony formation and antibody production. This is usually between about 7 and about 14 days.

The hybridoma colonies are then assayed for the production of antibodies that specifically bind to TLR3 polypeptide gene products, optionally the epitope specifically recognized by antibody 11E1, 7G11, 31F6, 32C4 or 37B7. The assay is typically a colorimetric ELISA-type assay, although any assay may be employed that can be adapted to the wells that the hybridomas are grown in. Other assays include radioimmunoassays or fluorescence activated cell sorting. The wells positive for the desired antibody production are examined to determine if one or more distinct colonies are present. If more than one colony is present, the cells may be re-cloned and grown to ensure that only a single cell has given rise to the colony producing the desired antibody. Typically, the antibodies will also be tested for the ability to bind to TLR3 polypeptides, e.g., TLR3-expressing cells, in paraffin-embedded tissue sections, as described below.

Hybridomas that are confirmed to produce a monoclonal antibody of this invention can be grown up in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

Positive wells with a single apparent colony are typically re-cloned and re-assayed to insure only one monoclonal antibody is being detected and produced.

Antibodies may also be produced by selection of combinatorial libraries of immunoglobulins, as disclosed for instance in (Ward et al. Nature, 341 (1989) p. 544, the entire disclosure of which is herein incorporated by reference).

The identification of one or more antibodies that bind(s) to TLR3, particularly substantially or essentially the same epitope as monoclonal antibody 11E1, 7G11, 31F6, 32C4 or 37B7 can be readily determined using any one of a variety of immunological screening assays in which antibody competition can be assessed. Many such assays are routinely practiced and are well known in the art (see, e. g., U.S. Pat. No. 5,660,827, issued Aug. 26, 1997, which is specifically incorporated herein by reference). It will be understood that actually determining the epitope to which an antibody described herein binds is not in any way required to identify an antibody that binds to the same or substantially the same epitope as the monoclonal antibody described herein.

For example, where the test antibodies to be examined are obtained from different source animals, or are even of a different Ig isotype, a simple competition assay may be employed in which the control (11E1, 7G11, 31F6, 32C4 or 37B7, for example) and test antibodies are admixed (or pre-adsorbed) and applied to a sample containing TLR3 polypeptides. Protocols based upon western blotting and the use of BIACORE analysis are suitable for use in such competition studies.

In certain embodiments, one pre-mixes the control antibodies (11E1, 7G11, 31F6, 32C4 or 37B7, for example) with varying amounts of the test antibodies (e.g., about 1:10 or about 1:100) for a period of time prior to applying to the TLR3 antigen sample. In other embodiments, the control and varying amounts of test antibodies can simply be admixed during exposure to the TLR3 antigen sample. As long as one can distinguish bound from free antibodies (e. g., by using separation or washing techniques to eliminate unbound antibodies) and 11E1, 7G11, 31F6, 32C4 or 37B7 from the test antibodies (e. g., by using species-specific or isotype-specific secondary antibodies or by specifically labeling 11E1, 7G11, 31F6, 32C4 or 37B7 with a detectable label) one can determine if the test antibodies reduce the binding of 11E1, 7G11, 31F6, 32C4 or 37B7 to the antigens, indicating that the test antibody recognizes substantially the same epitope as 11E1, 7G11, 31F6, 32C4 or 37B7. The binding of the (labeled) control antibodies in the absence of a completely irrelevant antibody can serve as the control high value. The control low value can be obtained by incubating the labeled (11E1, 7G11, 31F6, 32C4 or 37B7) antibodies with unlabelled antibodies of exactly the same type (11E1, 7G11, 31F6, 32C4 or 37B7), where competition would occur and reduce binding of the labeled antibodies. In a test assay, a significant reduction in labeled antibody reactivity in the presence of a test antibody is indicative of a test antibody that recognizes substantially the same epitope, i.e., one that "cross-reacts" or competes with the labeled (11E1, 7G11, 31F6, 32C4 or 37B7) antibody. Any test antibody that reduces the binding of 11E1, 7G11, 31F6, 32C4 or 37B7 to TLR3 antigens by at least about 50%, such as at least about 60%, or more preferably at least about 80% or 90% (e. g., about 65-100%), at any ratio of 11E1, 7G11, 31F6, 32C4 or 37B7:test antibody between about 1:10 and about 1:100 is considered to be an antibody that binds to substantially the same epitope or determinant as 11E1, 7G11, 31F6, 32C4 or 37B7. Preferably, such test antibody will reduce the binding of 11E1, 7G11, 31F6, 32C4 or 37B7 to the TLR3 antigen by at least about 90% (e.g., about 95%).

Competition can also be assessed by, for example, a flow cytometry test. In such a test, cells bearing a given TLR3 polypeptide can be incubated first with 11E1, for example, and then with the test antibody labeled with a fluorochrome or biotin. The antibody is said to compete with 11E1 if the binding obtained upon preincubation with a saturating amount of 11E1 is about 80%, preferably about 50%, about 40% or less (e.g., about 30%, 20% or 10%) of the binding (as measured by mean of fluorescence) obtained by the antibody without preincubation with 11E1. Alternatively, an antibody is said to compete with 11E1 if the binding obtained with a labeled 11E1 antibody (by a fluorochrome or biotin) on cells preincubated with a saturating amount of test antibody is about 80%, preferably about 50%, about 40%, or less (e. g., about 30%, 20% or 10%) of the binding obtained without preincubation with the test antibody.

A simple competition assay in which a test antibody is pre-adsorbed and applied at saturating concentration to a surface onto which a TLR3 antigen is immobilized may also be employed. The surface in the simple competition assay is preferably a BIACORE chip (or other media suitable for surface plasmon resonance analysis). The control antibody (e.g., 11E1) is then brought into contact with the surface at a TLR3-saturating concentration and the TLR3 and surface binding of the control antibody is measured. This binding of the control antibody is compared with the binding of the control antibody to the TLR3-containing surface in the absence of test antibody. In a test assay, a significant reduction in binding of the TLR3-containing surface by the control antibody in the presence of a test antibody indicates that the test antibody recognizes substantially the same epitope as the control antibody such that the test antibody "cross-reacts" with the control antibody. Any test antibody that reduces the binding of control (such as 11E1) antibody to a TLR3 antigen by at least about 30% or more, preferably about 40%, can be considered to be an antibody that binds to substantially the same epitope or determinant as a control (e.g., 11E1). Preferably, such a test antibody will reduce the binding of the control antibody (e.g., 11E1) to the TLR3 antigen by at least about 50% (e. g., at least about 60%, at least about 70%, or more). It will be appreciated that the order of control and test antibodies can be reversed: that is, the control antibody can be first bound to the surface and the test antibody is brought into contact with the surface thereafter in a competition assay. Preferably, the antibody having higher affinity for the TLR3 antigen is bound to the surface first, as it will be expected that the decrease in binding seen for the second antibody (assuming the antibodies are cross-reacting) will be of greater magnitude. Further examples of such assays are provided in, e.g., Saunal (1995) J. Immunol. Methods 183: 33-41, the disclosure of which is incorporated herein by reference.

Determination of whether an antibody binds within an epitope region can be carried out in ways known to the person skilled in the art. As one example of such mapping/characterization methods, an epitope region for an anti-TLR3 antibody may be determined by epitope "foot-printing" using chemical modification of the exposed amines/carboxyls in the TLR3 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e. g., Ehring H, Analytical Biochemistry, Vol. 267 (2) pp. 252-259 (1999) Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectra of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectrum of the complex compared to the spectrum of the free antigen, and the amino acids involved in the binding can be identified that way. See, e. g., Ernst Schering Res Found Workshop. 2004; (44): 149-67; Huang et al., Journal of Molecular Biology, Vol. 281 (1) pp. 61-67 (1998); and Saito and Patterson, Methods. 1996 June; 9 (3): 516-24.

Epitope mapping/characterization also can be performed using mass spectrometry methods. See, e.g., Downard, J Mass Spectrom. (2000) 35 (4): 493-503 and Kiselar and Downard, Anal Chem. (1999) 71 (9): 1792-801. Protease digestion techniques also can be useful in the context of epitope mapping and identification. Antigenic determinant-relevant regions/sequences can be determined by protease digestion, e.g. by using trypsin in a ratio of about 1:50 to TLR3 or o/n digestion at and pH 7-8, followed by mass spectrometry (MS) analysis for peptide identification. The peptides protected from trypsin cleavage by the anti-TLR3 binder can subsequently be identified by comparison of samples subjected to trypsin digestion and samples incubated with antibody and then subjected to digestion by e.g. trypsin (thereby revealing a footprint for the binder). Other enzymes like chymotrypsin, pepsin, etc., also or alternatively can be used in similar epitope characterization methods. Moreover, enzymatic digestion can provide a quick method for analyzing whether a potential antigenic determinant sequence is within a region of the TLR3 polypeptide that is not surface exposed and, accordingly, most likely not relevant in terms of immunogenicity/antigenicity. See, e. g., Manca, Ann 1st Super Sanita. 1991; 27: 15-9 for a discussion of similar techniques.

Site-directed mutagenesis is another technique useful for elucidation of a binding epitope. For example, in "alanine-scanning", each residue within a protein segment is replaced with an alanine residue, and the consequences for binding affinity measured. If the mutation leads to a significant resuction in binding affinity, it is most likely involved in binding. Monoclonal antibodies specific for structural epitopes (i.e., antibodies which do not bind the unfolded protein) can be used to verify that the alanine-replacement does not influence over-all fold of the protein. See, e.g., Clackson and Wells, Science 1995; 267:383-386; and Wells, Proc Natl Acad Sci USA 1996; 93:1-6.

Electron microscopy can also be used for epitope "foot-printing". For example, Wang et al., Nature 1992; 355:275-278 used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include surface plasmon resonance (SPR, BIACORE) and reflectometric interference spectroscopy (RifS). See, e.g., Fägerstam et al., Journal Of Molecular Recognition 1990; 3:208-14; Nice et al., J. Chroma-togr. 1993; 646:159-168; Leipert et al., Angew. Chem. Int. Ed. 1998; 37:3308-3311; Kroger et al., Biosensors and Bioelectronics 2002; 17:937-944.

It should also be noted that an antibody binding the same or substantially the same epitope as an antibody of the invention can be identified in one or more of the exemplary competition assays described herein.

Once antibodies are identified that are capable of binding TLR3 and/or having other desired properties, they will also typically be assessed, using standard methods including those described herein, for their ability to bind to other polypeptides, including unrelated polypeptides and other TLR family members (e.g., human TLR1, 2, or 4-10). Ideally, the antibodies only bind with substantial affinity to TLR3, e.g., human TLR3, and do not bind at a significant level to unrelated polypeptides or to other TLR family members (e.g., TLR2 or TLR4; the amino acid sequence of human precursor TLR4 including a signal peptide at amino acid residues 1-23 is found in NCBI accession number NP_612564, the disclosure of which is incorporated herein by reference). However, it will be appreciated that, as long as the affinity for TLR3 is substantially greater (e.g., 5×, 10×, 50×, 100×, 500×, 1000×, 10,000×, or more) than it is for other TLR family members (or other, unrelated polypeptides), then the antibodies are suitable for use in the present methods.

The binding of the antibodies to TLR3-expressing cells can also be assessed in non-human primates, e.g. rhesus or cynomolgus monkeys, or other mammals such as mice. The invention therefore provides an antibody, as well as fragments and derivatives thereof, wherein said antibody, fragment or derivative specifically binds TLR3, and which furthermore bind TLR3 from non-human primates, e.g., rhesus or cynomolgus monkeys, a TLR3 polypeptide of SEQ ID NO: 2. Optionally, cellular uptake or localization, optionally localization in a subcellular compartment such as the endocytic pathway, is assessed in order to select an antibody that is readily taken up into the cell and/or into the cellular compartment where it TLR3 is expressed. Cellular uptake or localization will generally be measured in the cells in which the antibody is sought or believed to exert its activity, such as in DC. Cellular uptake or localization can be assessed by standard methods, such as by confocal staining using an antibody marked with a detectable moiety (e.g. a fluorescent moiety).

Upon immunization and production of antibodies in a vertebrate or cell, particular selection steps may be performed to isolate antibodies as claimed. In this regard, in a specific embodiment, the invention also relates to methods of producing antibodies that inhibit TLR3 signaling, comprising: (a) providing a plurality of antibodies; and (b) selecting antibodies from step (a) that are capable of binding with high affinity a TLR3 polypeptide expressed solely at the cell surface. The antibodies can be tested for binding to TLR3 under neutral conditions. In one embodiment, step (a) comprises (i) immunizing a non-human mammal with an immunogen comprising a TLR3 polypeptide; and (ii) preparing antibodies from said immunized animal. In one embodiment, step (a) comprises generating library of antibody sequences (e.g. using phage-display).

The antibodies' bivalent binding affinity for human TLR3 under acidic conditions can determined. Antibodies can be characterized for example by a mean KD of no more than about (i.e. better affinity than) 100, 60, 10, 5, or 1 nanomolar, preferably sub-nanomolar or optionally no more than about 300, 200, 100 or 10 picomolar. $K_D$ can be determined for example for example by immobilizing recombinantly produced human TLR3 proteins on a chip surface, followed by application of the antibody to be tested in solution, e.g. as shown in the present Examples. To select antibodies that retain binding similar binding under acidic and neutral conditions, one can seek to minimize the difference observed between binding at neutral pH (e.g. 7.2) and acidic pH (e.g. a pH in the range of 4.5-6-5), for example where binding affinity at acidic pH is not substantially lower, e.g. where the $K_D$ for binding to TLR3 decreases by no more than 0.2-, 0.3-, 0.5-, 1.0-, or 1.5-log 10, than that observed at non-acid pH. In one embodiment, the method further comprises a step (d), selecting antibodies from (b) that are capable of competing for binding to TLR3 with antibody 11E1, 7G11, 31F6, 32C4 or 37B7, or that are capable of (or not capable of) competing for binding to TLR3 with dsRNA (e.g. polyAU).

In one aspect of any of the embodiments, the antibodies prepared according to the present methods are monoclonal antibodies. In another aspect, the non-human animal used to produce antibodies according to the methods of the invention is a mammal, such as a rodent (e.g. rat), bovine, porcine, fowl, horse, rabbit, goat, or sheep. The antibodies of the present invention encompass 11E1, 7G11, 31F6, 32C4 and 37B7. However, it will be appreciated that other antibodies can be obtained using the methods described herein, and thus antibodies of the invention can be antibodies other than 11E1, 7G11, 31F6, 32C4 and 37B7. Additionally, antibodies of the invention can optionally be specified to be antibodies other than any of antibodies 31C3, 29H3, 23C8, 28F11 or 34A3 disclosed in WO2011/004028 or as deposited Collection Nationale de Culture de Microorganismes (CNCM), Institut Pasteur, 25 rue de Docteur Roux, F-75724 Paris on 3 Jul. 2009, under the number CNCM 1-4187 (29H3.7) and CNCM 1-4186 (31C3.1), antibody TLR3.7 (eBioScience Inc., San Diego), antibody C1068 of WO 06/060513, antibody C1130 of WO 2007/051164, any of the antibodies disclosed WO2010/051470, e.g., antibodies 1-19 and F17-F19, and their variants such as 15EVQ and 12QVQ/QSV, antibody 40C1285 (Abcam), or antibodies 619F7, 713E4, 716G10, IMG-5631, IMG-315 or IMG-5348 (all from Imgenex. Corp.) or derivatives of the foregoing, e.g. that comprise the antigen binding region in whole or in part. Each of the above disclosures are incorporated herein by reference.

According to an alternate embodiment, the DNA encoding an antibody that binds an epitope present on TLR3 polypeptides is isolated from the hybridoma of this invention and placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

DNA encoding the monoclonal antibodies of the invention can be readily isolated and sequenced using conventional procedures (e. g., by using oligonucleotide probes that are capable of binding specifically to genes encoding the heavy and light chains of murine antibodies). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. As described elsewhere in the present specification, such DNA sequences can be modified for any of a large number of purposes, e.g., for humanizing antibodies, producing fragments or derivatives, or for modifying the sequence of the antibody, e.g., in the antigen binding site in order to optimize the binding specificity of the antibody.

Recombinant expression in bacteria of DNA encoding the antibody is well known in the art (see, for example, Skerra et al., Curr. Opinion in Immunol., 5, pp. 256 (1993); and Pluckthun, Immunol. 130, p. 151 (1992).

Assessing the Ability of Antibodies to Modulate TLR3 Signaling

In certain embodiments, the antibodies of this invention are able to modulate, e.g., inhibit signaling by, TLR3 polypeptides, and consequently to modulate the activity or behavior of TLR3-expressing cells. For example, antibodies may inhibit the activation of TLR3-expressing cells, e.g. they can inhibit the TLR3 signaling pathway, optionally by blocking the binding to TLR3 of natural or endogenous ligands such as dsRNA; optionally they may block the ability of TLR3 protein to form homodimers in the presence of a TLR3 ligand, thus blocking the initiation a signaling cascade. These antibodies are thus referred to as "neutralizing" or "inhibitory" or "blocking" antibodies. Such antibodies are useful, inter alia, for decreasing the activity of TLR3-expressing immune cells, e.g. for the treatment or prevention of conditions involving excess TLR3-expressing cell activity or number, or where decreased TLR3-expressing cell activity can ameliorate, prevent, eliminate, or in any way improve the condition or any symptom thereof.

A range of cellular assays can be used to assess the ability of the antibodies to modulate TLR3 signaling. Any of a large number of assays, including molecular, cell-based, and animal-based models can be used to assess the ability of anti-TLR3 antibodies to modulate TLR3-expressing cell activity. For example, cell-based assays can be used in which cells expressing TLR3 are exposed to dsRNA, viral dsRNA, polyIC, or poly AU, or another TLR3 ligand and the ability of the antibody to disrupt the binding of the ligand or the stimulation of the receptor (as determined, e.g., by examining any of the TLR3 cell activities addressed herein, such as interferon expression, NFkB activity, NK cell activation, etc.) is assessed. The TLR3 ligand used in the assays may be in any suitable form, including but not limited to as a purified ligand composition, in a mixture with non-TLR3 ligands, in a naturally occurring composition, in a cell or on the surface of a cell, or secreted by a cell (e.g. a cell that produces ligand is used in the assay), in solution or on a solid support.

The activity of TLR3-expressing cells can also be assessed in the absence of a ligand, by exposing the cells to the antibody itself and assessing its effect on any aspect of the cells' activity or behavior. In such assays, a baseline level of activity (e.g., cytokine production, proliferation, see below) of the TLR3-expressing cells is obtained in the absence of a ligand, and the ability of the antibody or compound to alter the baseline activity level is detected. In one such embodiment, a high-throughput screening approach is used to identify compounds capable of affecting the activation of the receptor.

Any suitable physiological change that reflects TLR3 activity can be used to evaluate test antibodies or antibody derivatives. For example, one can measure a variety of effects, such as changes in gene expression (e.g., NFkB-responding genes), protein secretion (e.g., interferon), cell growth, cell proliferation, pH, intracellular second messengers, e.g., $Ca^{2+}$, IP3, cGMP, or cAMP, or activity such as ability to activate NK cells. In one embodiment, the activity of the receptor is assessed by detecting production of cytokines, e.g. TLR3-responsive cytokines, proinflammatory cytokines.

TLR3 modulation can be assessed using any of a number of possible readout systems, most based upon a TLR/IL-1R signal transduction pathway, involving, e.g., the MyD88-independent/TRIF dependent signal transduction pathway, involving, e.g., IRF3, IRF7, IKKε and/or TBK1 (Akira and Takeda (2004) Nature Review Immunol. 4:499-511). These pathways activate kinases including KB kinase complex. TLR3 activation can be assessed by examining any aspect of TLR signaling. For example, activation of TLR signaling triggers alterations in protein-protein associations (e.g., TRIF with TBK and/or IKKε), in intracellular localization of proteins (such as movement of NK-kB into the nucleus), and in gene expression (e.g., in expression of NK-kB sensitive genes), and cytokine production (e.g., production and secretion of IFN-gamma, IL-6, IP10, MCP-1). Any such alteration can be detected and used to detect TLR3 activation. In one embodiment, TLR3 stimulation is detected by collecting supernatants after 18-20 hr of culture and measuring levels of IFN-gamma, IL-6, IP-10 and/or MCP-1 by sandwich ELISA. In another embodiment, TLR3 stimulation is detected by collecting supernatants after 18-20 hr of culture and measuring levels of IFN-gamma, IL-6, IP-10 and/or MCP-1 by sandwich ELISA.

In one embodiment, cells that naturally express TLR3 are used, such as DC (e.g. myeloid DC or monocyte derived DC. In another embodiment, cells are used that contain a reporter construct that causes the expression of a detectable gene product upon TLR3 stimulation and consequent activation of the signal transduction pathway. Reporter genes and reporter gene constructs particularly useful for the assays include, e.g., a reporter gene operatively linked to a promoter sensitive to NF-kB or to signaling mediated by, particularly TRIF, IRF3, IRF7, IKKε, TBK1. Examples of such promoters include, without limitation, those for IL-1alpha, IL-6, IL-8, IL-12 p40, IP-10, CD80, CD86, and TNF-alpha. The reporter gene operatively linked to the TLR-sensitive promoter can include, without limitation, an enzyme (e.g., luciferase, alkaline phosphatase, beta-galactosidase, chloramphenicol acetyltransferase (CAT), etc.), a bioluminescence marker (e.g., green-fluorescent protein (GFP, e.g., U.S. Pat. No. 5,491,084), blue fluorescent protein (BFP, e.g., U.S. Pat. No. 6,486,382), etc.), a surface-expressed molecule (e.g., CD25, CD80, CD86), and a secreted molecule (e.g., IL-1, IL-6, IL-8, IL-12 p40, TNF-alpha). See, e.g., Hcker H et al. (1999) EMBO J. 18:6973-82; Murphy T L et al. (1995) Mol Cell Biol 15:5258-67, the disclosures of which are herein incorporated by reference. Reporter plasmids suitable for use are commercially available (InvivoGen, San Diego, Calif.). In one embodiment, the assay includes determining, in a host cell made to express a human TLR3 polypeptide, whether a test composition induces luciferase expression (or other reporter) under the control of a promoter responsive to TLR3 signaling (e.g. ISRE, IFN-stimulated response element).

In assays relying on enzyme activity readout, substrate can be supplied as part of the assay, and detection can involve measurement of chemoluminescence, fluorescence, color development, incorporation of radioactive label, drug resistance, optical density, or other marker of enzyme activity. For assays relying on surface expression of a molecule, detection can be accomplished using flow cytometry (FACS) analysis or functional assays. Secreted molecules can be assayed using enzyme-linked immunosorbent assay (ELISA) or bioassays. Many of these and other suitable readout systems are well known in the art and are commercially available. Preferably, the reporter system, whichever used, is quantifiable.

In another embodiment, the effect of the antibodies on TLR3-expressing cells is assessed in non-human primates in vivo. For example, a pharmaceutical composition comprising an anti-TLR3 antibody of the present invention is administered to a non-human primate that is either healthy or affected by a condition, e.g. an autoimmune disease or inflammation and the effect of the administration on, e.g., the number or activity of TLR3-expressing cells in the primate, the presence and/or levels of cytokines, or on the progression of the condition is assessed. Any antibody or antibody derivative or fragment that effects a detectable change in any of these TLR3-related parameters is a candidate for use in the herein-described methods.

In any of the herein-described assays, an increase or decrease of 5%, 10%, 20%, preferably 30%, 40%, 50%, most preferably 60%, 70%, 80%, 90%, 95%, or greater in any detectable measure of TLR3-stimulated activity in the cells indicates that the test antibody is suitable for use in the present methods.

When assessing inhibitory anti-TLR3 antibodies, the antibodies can be advantageously selected to modify any parameter associated with inflammation or autoimmunity. For example, antibodies can be selected to reduce activation, particularly production of pro-inflammatory cytokines, in cells. The cells may be, for example, cells obtained from an individual suffering from an inflammatory or autoimmune disorder.

Antibodies

The antibodies of the present invention bind human TLR3 polypeptides. In an embodiment, the antibodies are antagonistic TLR3 antibodies. In another embodiment, the antibodies block the signaling induced through human TLR3.

The antibodies optionally have affinity ($K_D$) at an acidic pH, i.e. a pH of about 5.6, of less than $10^{-9}$ M, preferably less than $10^{-10}$M. In another embodiment, the antibodies have an affinity ($K_D$) at a neutral pH, i.e. a pH of about 7.2, of less than $10^{-9}$ M, preferably less than $10^{-10}$M. In another embodiment, the antibodies have an affinity ($K_D$) at an acidic pH, i.e. a pH of about 5.6, and at a neutral pH, i.e. a pH of about 7.2, of less than $10^{-9}$ M, preferably less than $10^{-10}$M. Affinity may be, for example monovalent or bivalent binding to TLR3.

In another embodiment, the antibodies are able to inhibit TLR3 signaling in the presence of a TLR3 ligand, i.e. dsRNA (polyAU, polyIC). In another embodiment, the antibodies are able to inhibit TLR3 signaling when administered after a TLR3 ligand. In another embodiment, the antibodies are able to inhibit TLR3 signaling when administered before a TLR3 ligand. In another embodiment, the antibodies are able to inhibit TLR3 signaling when administered simultaneously with a TLR3 ligand.

In another embodiment, the antibodies compete for binding with dsRNA to the N-terminal dsRNA binding site of the TLR3 polypeptide. In another embodiment, the antibodies do not compete for binding with dsRNA to the C-terminal dsRNA binding site of the TLR3 polypeptide.

Antibody Epitopes

In another embodiment, the antibodies bind substantially the same epitope as antibody 11E1, 7G11, 31F6, 32C4 or 37B7. In one embodiment, all key residues of the epitope is in a segment corresponding to residues 1 to 251 of the TLR3 polypeptide of SEQ ID NO: 1. In one embodiment, the antibodies bind an epitope comprising 1, 2, 3, 4, 5, 6, 7 or more residues in the segment corresponding to residues 1 to 251 (or 41-139, 41-115, 41-120 or 41-251) of the TLR3 polypeptide of SEQ ID NO: 1. In another embodiment, the antibodies bind one or more amino acids present on the surface of the TLR3 polypeptide within the epitopes bound by the anti-TLR3 antibodies of the invention, optionally, the antibodies bind 1, 2, 3, 4, 5, 6, 7 or more residues selected from the group consisting of: 41, 43, 60, 61, 62, 64, 65, 66, 67, 68, 86, 88, 89, 91, 92, 93, 96, 97, 108, 110, 112, 113, 114, 115, 117, 120, 121, 132, 134, 137 and residue 139 of SEQ ID NO: 1.

Optionally, the antibodies bind at least partly (or primarily) on the glycan-free lateral surface of the N-terminal portion of the human TLR3 polypeptide. Optionally, the antibodies bind at least partly (or primarily) on the backbone of the N-terminal portion of the human TLR3 polypeptide. Optionally, the antibodies bind at least partly (or primarily) on the glycan-free lateral surface of the N-terminal portion of the human TLR3 polypeptide and partly on the backbone of the N-terminal portion of the human TLR3 polypeptide. Optionally, the antibodies bind one or more amino acid residues within the glycan-free lateral surface of the TLR3 polypeptide that is involved in binding of the TLR3 polypeptide to dsRNA, and/or residues adjacent thereto. Optionally, the antibodies bind an epitope comprising residues 41 and/or residue 43 of SEQ ID NO: 1. Optionally, the antibodies bind an epitope comprising 1, 2, 3, 4, 5, 6 or 7 of residues 60, 61, 62, 64, 65, 67 and/or residue 68 of SEQ ID NO: 1. Optionally, the antibodies bind an epitope comprising 1, 2 or 3 of residues 86, 88 and/or residue 89 of SEQ ID NO: 1. Optionally, the antibodies bind an epitope comprising 1, 2, 3, 4, 5 or 6 of residues 91, 92, 93, 96, 97 and/or residue 121 of SEQ ID NO: 1. Optionally, the antibodies bind an epitope comprising 1, 2, 3, 4, 5, 6, 7 or more of residues 108, 110, 112, 113, 114, 115, 116, 117, 120. Optionally, the antibodies bind an epitope comprising 1, 2, 3 or 4, of residues 132, 134, 137 and/or residue 139 of SEQ ID NO: 1. Optionally, the antibodies bind an epitope comprising 1, 2, 3 or, 4 of the residues 112, 113, 115, 117, 120, 137 and 139. Optionally, the antibodies bind an epitope comprising residue 117 and residues 137 and/or 139. Optionally, the antibodies bind an epitope comprising residue 120 and residues 137 and/or 139. Optionally, the antibodies bind an epitope comprising residue 117 and/or 120 but not residues 137 and/or 139. Optionally, the antibodies bind an epitope comprising 1, 2, 3, 4, 5 or 6 of the residues R64, R65, T86 and K89, K137 and K139. Optionally, the antibodies bind an epitope comprising residue 64 and residues 137 and/or 139. Optionally, the antibodies bind an epitope comprising residue 65 and residues 137 and/or 139. Optionally, the antibodies bind an epitope comprising residue 86 and residues 137 and/or 139. Optionally, the antibodies bind an epitope comprising residue 89 and residues 137 and/or 139. In one embodiment, amino acid residues within the glycan-free lateral surface of the TLR3 polypeptide that is involved in binding of the TLR3 polypeptide to dsRNA, and/or residues adjacent thereto, are selected from the group consisting of residues 41, 43, 60, 61, 62, 64, 65, 67, 68, 86, 88, 89, 108, 110, 112, 113, 114, 132, 134, 137 and residue 139 of SEQ ID NO: 1. Optionally, the antibodies bind an epitope comprising 1, 2, 3 or, 4 of the residues 112, 113 and 137 of SEQ ID NO: 1. In one embodiment, amino acid residues within the backbone of the N-terminal portion of the human TLR3 polypeptide are selected from the group consisting of residues 91, 92, 93, 96, 97, 117, 120 and 121 of SEQ ID NO: 1. Optionally, the antibodies do not bind, or do not bind principally, on the glycan-containing lateral surface of the N-terminal portion of the human TLR3 polypeptide Optionally, in any embodiment, the antibodies can optionally further be characterized by not substantially binding to one, two, three, or more residues in the segment corresponding to residues 174 to 191 residues 465-619, or to residues 116, 145 and/or 182, of the mature TLR3 polypeptide of SEQ ID NO: 1. In another embodiment, the antibodies bind to, or optionally do not bind to, an epitope comprising one or more residues in the segment corresponding to residues 177 to 191, 224 to 243, 280 to 286, 295 to 374, 379 to 391, 428 to 459, 461 to 487, 524 to 529, 533 to 542, 546 to 569, 575 to 581, 583 to 605, 607 to 623, 641 to 657 and/or 670 to 705 of the TLR3 polypeptide of SEQ ID NO: 1.

The Examples section herein describes the construction of a series of mutant human TLR3 polypeptides. Binding of anti-TLR3 antibody to cells transfected with the TLR3 mutants was measured and compared to the ability of anti-TLR3 antibody to bind wild-type TLR3 polypeptide (SEQ ID NO:1). A reduction in binding between an anti-TLR3 antibody and a mutant TLR3 polypeptide as used herein means that there is a reduction in binding affinity (e.g., as measured by known methods such FACS testing of cells expressing a particular mutant, or by Biacore testing of binding to mutant polypeptides) and/or a reduction in the total binding capacity of the anti-TLR3 antibody (e.g., as evidenced by a decrease in Bmax in a plot of anti-TLR3 antibody concentration versus polypeptide concentration). A significant reduction in binding indicates that the mutated residue is directly involved in binding to the anti-TLR3 antibody or is in close proximity to the binding protein when the anti-TLR3 antibody is bound to TLR3. An antibody epitope will thus preferably include such residue and may include additional residues adjacent to such residue.

In some embodiments, a significant reduction in binding means that the binding affinity and/or capacity between an anti-TLR3 antibody and a mutant TLR3 polypeptide is reduced by greater than 40%, greater than 50%, greater than 55%, greater than 60%, greater than 65%, greater than 70%, greater than 75%, greater than 80%, greater than 85%, greater than 90% or greater than 95% relative to binding between the antibody and a wild type TLR3 polypeptide (e.g., the polypeptide shown in SEQ ID NO:1). In certain embodiments, binding is reduced below detectable limits. In some embodiments, a significant reduction in binding is evidenced when binding of an anti-TLR3 antibody to a mutant TLR3 polypeptide is less than 50% (e.g., less than 45%, 40%, 35%, 30%, 25%, 20%, 15% or 10%) of the binding observed between the anti-TLR3 antibody and a wild-type TLR3 polypeptide (e.g., the extracellular domain shown in SEQ ID NO:1). Such binding measurements can be made using a variety of binding assays known in the art. A specific example of one such assay is described in the Example section.

In some embodiments, anti-TLR3 antibodies are provided that exhibit significantly lower binding for a mutant TLR3 polypeptide in which a residue in a wild-type TLR3 polypeptide (e.g., SEQ ID NO:1) is substituted. In the shorthand notation used here, the format is: Wild type residue: Position in polypeptide: Mutant residue, with the numbering of the residues as indicated in SEQ ID NO: 1.

Optionally, the antibodies have reduced binding to a TLR3 polypeptide having a substitution at residues 41, 43, 60, 61, 62, 64, 65, 67, 68, 86, 88, 89, 91, 92, 93, 96, 97, 108, 110, 112, 113, 114, 115, 117, 120, 121, 132, 134, 137 and/or residue 139 of SEQ ID NO: 1.

In some embodiments, an anti-TLR3 antibody binds a wild-type TLR3 polypeptide having a sequence of SEQ ID NO: 1 but has decreased binding to a mutant TLR3 polypeptide having any one or more (e.g., 1, 2, 3 or 4) of the following mutations: R64Q, R65Q, T86S, K89Q, K117Q, A120V, K137S and/or K139A (with reference to SEQ ID NO:1). Preferably binding to the mutant TLR3 is significantly reduced compared to binding to the wild-type TLR3.

In another embodiment, the antibodies are able of inhibiting cytokine (e.g. IP-10) secretion in myeloid dendritic cells (MdDC). In another embodiment, the antibodies are capable of internalizing into a TLR3-expressing cell rapidly and efficiently. In another embodiment, the antibodies are capable of internalizing without inducing or requiring hTLR3 down-modulation.

Antibody CDR Sequences

In one aspect of any of the embodiments of the invention, an antibody may comprise a heavy and/or light chain having CDR1, 2 and/or 3 sequences according to the respective formula selected from Formulas (I) to (VII). In any embodiment herein, a particular LCDR1 or -2 or HCDR-1 or 2 may be specified as having a sequence of Formulas (I) to (VII). In any embodiment herein, a particular HCDR1-3 or LCDR-1-3 may be specified as having a sequence of Formulas (I) to (VII). In one preferred embodiment, the antibody comprises a light chain comprising the three LCDRs and a heavy chain comprising the three HCDRs. Optionally, provided is an antibody where any of the light and/or heavy chain variable regions are fused to an immunoglobulin constant region of the IgG type, optionally a human constant region, optionally an IgG1 or IgG4 isotype.

In one embodiment, LCDR1 comprises a sequence of Formula (I):

(I)

(SEQ ID NO: 58)

$Xaa_1$-A-S-E-$Xaa_2$-I-$Xaa_3$-$Xaa_4$-$Xaa_5$-L-A, wherein $Xaa_1$ to $Xaa_9$ may be a conservative or non-conservative substitution or a deletion or insertion, preferably, wherein $Xaa_1$ may be Leu or Gln, and/or $Xaa_2$ may be Asp or Gly, and/or $Xaa_3$ may be Ser or Tyr, and/or $Xaa_4$ may be Asn or Ser, and/or $Xaa_9$ may be Asp, Tyr or Gly.

In one embodiment, LCDR2 comprises a sequence of Formula (II):

(II)

(SEQ ID NO: 59)

A-A-$Xaa_6$-R-L-$Xaa_7$-D, wherein $Xaa_6$ to $Xaa_7$ may be a conservative or non-conservative substitution or a deletion or insertion, preferably, wherein $Xaa_6$ may be Ser or Asn and/or $Xaa_7$ may be Glu or Gln.

In one embodiment, LCDR3 comprises a sequence of Formula (III):

(III)
(SEQ ID NO: 60)
Xaa$_8$-Q-Xaa$_9$-Xaa$_{10}$-Xaa$_{11}$-Xaa$_{12}$-P-Xaa$_{13}$-T, wherein Xaa$_8$ to Xaa$_{13}$ may be a conservative or non-conservative substitution or a deletion or insertion, preferably, wherein Xaa$_8$ may be Leu or Gln, and/or Xaa$_9$ may be Ser, Asn or Gly, and/or Xaa$_{10}$ may be Tyr, Ser or Val, and/or Xaa$_{11}$ may be Lys or Glu, and/or Xaa$_{12}$ may be Phe or Tyr, and/or Xaa$_{13}$ may be Asn, Tyr, Leu or Val.

In one embodiment, HCDR1 comprises a sequence of Formula (IV):

(IV)
(SEQ ID NO: 61)
Xaa$_{14}$-Xaa$_{15}$-Y-Xaa$_{16}$-Xaa$_{17}$, wherein Xaa$_{14}$ to Xaa$_{17}$ may be a conservative or non-conservative substitution or a deletion or insertion, preferably, wherein Xaa$_{14}$ may be Tyr or Ser, and/or Xaa$_{15}$ may be Thr or Asn, and/or Xaa$_{16}$ may be Met or Ile, and/or Xaa$_{17}$ may be Tyr or His.

In one embodiment, HCDR1 comprises a sequence of Formula (V):

(V)
(SEQ ID NO: 62)
G-Y-Xaa$_{18}$-Xaa$_{19}$-Xaa$_{20}$-Xaa$_{21}$, wherein Xaa$_{18}$ to Xaa$_{21}$ may be a conservative or non-conservative substitution or a deletion or insertion, preferably, wherein Xaa$_{18}$ may be Thr or Asn, and/or Xaa$_{19}$ may be Phe or Ile, and/or Xaa$_{20}$ may be Arg, Trp or Thr; and/or Xaa$_{21}$ may be Tyr or Ser.

In one embodiment, HCDR2 comprises a sequence of Formula (VI):

(VI)
(SEQ ID NO: 63)
Xaa$_{22}$-I-Xaa$_{23}$-P-Xaa$_{24}$-Xaa$_{25}$-G, wherein Xaa$_{22}$ to Xaa$_{25}$ may be a conservative or non-conservative substitution or a deletion or insertion, preferably, wherein Xaa$_{22}$ may be Arg or Trp, and/or Xaa$_{23}$ may be Asp or Phe, and/or Xaa$_{24}$ may be Ala or Gly, and/or Xaa$_{25}$ may be Asn or Asp. Optionally HCDR of Formula VI further comprises a sequence -Xaa$_{26}$-Xaa$_{27}$-Xaa$_{28}$, wherein Xaa$_{26}$ to Xaa$_{28}$ may be a conservative or non-conservative substitution or a deletion or insertion, preferably, wherein Xaa$_{26}$ may be Asp or Asn, and/or Xaa$_{27}$ may be Thr or Ser, and/or Xaa$_{28}$ may be Asn or Ile.

In one embodiment, HCDR3 comprises a sequence of SEQ ID NO: 21, 32, 43 or 54, or of Formula (VII):

(VII)
(SEQ ID NO: 64)
G-Xaa$_{29}$-Xaa$_{30}$-Xaa$_{31}$-Y-F-D, wherein Xaa$_{29}$ to Xaa$_{31}$ may be a conservative or non-conservative substitution or a deletion or insertion, preferably, wherein Xaa$_{29}$ may be a deletion or Glu, and/or Xaa$_{30}$ may be Phe or Asp, and/or Xaa$_{31}$ may be Asp or Trp.

In one embodiment, an antibody of the invention may comprise a light chain comprising:

a. a light chain CDR1 (LCDR1) amino acid sequence selected from SEQ ID NOS: 22, 33, 44, 55 and 58; and/or
b. a light chain CDR2 (LCDR2) amino acid sequence selected from SEQ ID NOS: 23, 34, 45, 56 and 59; and/or
c. a light chain CDR3 (LCDR3) amino acid sequence selected from SEQ ID NOS: 24, 35, 46, 57 and 60.

In one embodiment, an antibody of the invention may comprise a heavy chain comprising:

a. a heavy chain CDR1 (HCDR1) amino acid sequence selected from SEQ ID NOS: 16-18, 27-29, 38-40, 49-51 and 61-62; and/or
b. a heavy chain CDR2 (HCDR2) amino acid sequence selected from SEQ ID NOS: 19, 20, 31, 31, 41, 42, 52, 53 and 63; and/or
c. a heavy chain CDR3 (HCDR3) amino acid sequence selected from SEQ ID NOS: 21, 32, 43, 54, and 64.

Antibody 11E1

The amino acid sequence of the heavy chain variable region of 11E1 is listed as SEQ ID NO:3, the amino acid sequence of the light chain variable region is listed as SEQ ID NO: 4. In a specific embodiment, the invention provides an antibody that binds essentially the same epitope or determinant as monoclonal antibodies 11E1; optionally the antibody comprises an antigen binding region of antibody 11E1. In any of the embodiments herein, antibody 11E1 can be characterized by its amino acid sequence and/or nucleic acid sequence encoding it. In one preferred embodiment, the monoclonal antibody comprises the Fab or F(ab')2 portion of 11E1. Also provided is a monoclonal antibody that comprises the heavy chain variable region of 11E1. According to one embodiment, the monoclonal antibody comprises the three CDRs of the heavy chain variable region of 11E1. Also provided is a monoclonal antibody that further comprises the variable light chain variable region of 11E1 or one, two or three of the CDRs of the light chain variable region of 11E1. Optionally any one or more of said light or heavy chain CDRs may contain one, two, three, four or five amino acid modifications (e.g. substitutions, insertions or deletions). Optionally, provided is an antibody where any of the light and/or heavy chain variable regions comprising part or all of an antigen binding region of antibody 11E1 are fused to an immunoglobulin constant region of the IgG type, optionally a human constant region, optionally a human IgG1 or IgG4 isotype. In another preferred embodiment the antibody is 11E1.

In another aspect, the invention provides an antibody or a purified polynucleotide which encodes an antibody, wherein the antibody comprises: a VHCDR1 region comprising an amino acid sequence as set forth in SEQ ID NO: 5, 6 or 7, wherein one or more amino acids may be substituted by a different amino acid; a VHCDR2 region comprising an amino acid sequence as set forth in SEQ ID NO: 8 or 9, wherein one or more amino acids may be substituted by a different amino acid; a VHCDR3 region comprising an amino acid sequence as set forth in SEQ ID NO: 10, wherein one or more amino acids may be substituted by a different amino acid; a VLCDR1 region comprising an amino acid sequence as set forth in SEQ ID NO: 11, wherein one or more amino acids may be substituted by a different amino acid; a VLCDR2 region comprising an amino acid sequence as set forth in SEQ ID NO:12, wherein one or more amino acids may be substituted by a different amino acid; a VLCDR3 region comprising an amino acid sequence as set forth in SEQ ID NO: 13, wherein one or more amino acids may be substituted by a different amino acid.

In another aspect, the invention provides an antibody that binds human TLR3, comprising:
a. the heavy chain variable region of SEQ ID NO: 3, wherein one, two, three or more amino acids may be substituted by a different amino acid; or
b. the light chain variable region of SEQ ID NO: 4, wherein one, two, three or more amino acids may be substituted by a different amino acid; or
c. the heavy chain variable region of SEQ ID NO: 3, wherein one, two, three or more of amino acids may be substituted by a different amino acid; and the light chain variable region of SEQ ID NO: 4, wherein one, two, three or more amino acids may be substituted by a different amino acid; or
d. the heavy chain CDRs 1, 2 and 3 (HCDR1, HCDR2, HCDR3) amino acid sequences as shown in SEQ ID NOS: 5-10, wherein one, two, three, four, five or more amino acids may be substituted by a different amino acid; or
e. the light chain CDRs 1, 2 and 3 (LCDR1, LCDR2, LCDR3) amino acid sequences as shown in SEQ ID NOS: 11-13, wherein one, two, three, four, five or more amino acids may be substituted by a different amino acid; or
f. the heavy chain CDRs 1, 2 and 3 (HCDR1, HCDR2, HCDR3) amino acid sequences as shown in SEQ ID NOS: 5-10, wherein one, two, three, four, five or more amino acids may be substituted by a different amino acid; and the light chain CDRs 1, 2 and 3 (LCDR1, LCDR2, LCDR3) amino acid sequences as shown in SEQ ID NOS: 11-13, wherein one, two, three, four, five or more amino acids may be substituted by a different amino acid; or
g. the heavy chain variable region having CDRs 1, 2 and 3 (HCDR1, HCDR2, HCDR3) amino acid sequences which are each at least 60%, 70%, 80%, 85%, 90% or 95% identical to the CDRs 1, 2 and 3 of the variable region having an amino acid sequence of SEQ ID NO: 3, wherein one, two, three, four, five or more amino acids may be substituted by a different amino acid; or
h. the light chain variable region having CDRs 1, 2 and 3 (LCDR1, LCDR2, LCDR3) amino acid sequences which are each at least 60%, 70%, 80%, 85%, 90% or 95% identical to the CDRs 1, 2 and 3 of the variable region having an amino acid sequence of SEQ ID NO: 4, wherein one, two, three, four, five or more amino acids may be substituted by a different amino acid.

In another aspect of any of the embodiments herein, any of the CDRs 1, 2 and 3 of the heavy and light chains may be characterized as having an amino acid sequence that shares at least 50%, 60%, 70%, 80%, 85%, 90% or 95% sequence identity with the particular CDR or set of CDRs listed in the corresponding SEQ ID NO.

In another aspect, the invention provides an antibody that competes for TLR3 binding with a monoclonal antibody of (a) to (h), above.

Antibody 31F6

The amino acid sequence of the heavy chain variable region of 31F6 is listed as SEQ ID NO: 14, the amino acid sequence of the light chain variable region is listed as SEQ ID NO: 15. In a specific embodiment, the invention provides an antibody that binds essentially the same epitope or determinant as monoclonal antibodies 31F6; optionally the antibody comprises an antigen binding region of antibody 31F6. In any of the embodiments herein, antibody 31F6 can be characterized by its amino acid sequence and/or nucleic acid sequence encoding it. In one preferred embodiment, the monoclonal antibody comprises the Fab or F(ab')2 portion of 31F6. Also provided is a monoclonal antibody that comprises the heavy chain variable region of 31F6. According to one embodiment, the monoclonal antibody comprises three CDRs of the heavy chain variable region of 31F6. Also provided is a monoclonal antibody that further comprises the variable light chain variable region of 31F6 or one, two or three of the CDRs of the light chain variable region of 31F6. Optionally any one or more of said light or heavy chain CDRs may contain one, two, three, four or five amino acid modifications (e.g. substitutions, insertions or deletions). Optionally, provided is an antibody where any of the light and/or heavy chain variable regions comprising part or all of an antigen binding region of antibody 31F6 are fused to an immunoglobulin constant region of the IgG type, optionally a human constant region, optionally a human IgG1 or IgG4 isotype. In another preferred embodiment the antibody is 31F6.

In another aspect, the invention provides an antibody or a purified polynucleotide which encodes an antibody, wherein the antibody comprises: a VHCDR1 region comprising an amino acid sequence as set forth in SEQ ID NO: 16, 17 or 18, wherein one or more amino acids may be substituted by a different amino acid; a VHCDR2 region comprising an amino acid sequence as set forth in SEQ ID NO: 19 or 20, wherein one or more amino acids may be substituted by a different amino acid; a VHCDR3 region comprising an amino acid sequence as set forth in SEQ ID NO: 21, wherein one or more amino acids may be substituted by a different amino acid; a VLCDR1 region comprising an amino acid sequence as set forth in SEQ ID NO: 22, wherein one or more amino acids may be substituted by a different amino acid; a VLCDR2 region comprising an amino acid sequence as set forth in SEQ ID NO: 23, wherein one or more amino acids may be substituted by a different amino acid; a VLCDR3 region comprising an amino acid sequence as set forth in SEQ ID NO: 24, wherein one or more amino acids may be substituted by a different amino acid.

In another aspect, the invention provides an antibody that binds human TLR3, comprising:
a. the heavy chain variable region of SEQ ID NO: 14, wherein one, two, three or more amino acids may be substituted by a different amino acid; or
b. the light chain variable region of SEQ ID NO: 15, wherein one, two, three or more amino acids may be substituted by a different amino acid; or
c. the heavy chain variable region of SEQ ID NO: 14, wherein one, two, three or more of amino acids may be substituted by a different amino acid; and the light chain variable region of SEQ ID NO: 15, wherein one, two, three or more amino acids may be substituted by a different amino acid; or
d. the heavy chain CDRs 1, 2 and 3 (HCDR1, HCDR2, HCDR3) amino acid sequences as shown in SEQ ID NOS: 16-21, wherein one, two, three, four, five or more amino acids may be substituted by a different amino acid; or
e. the light chain CDRs 1, 2 and 3 (LCDR1, LCDR2, LCDR3) amino acid sequences as shown in SEQ ID NOS: 22-24, wherein one, two, three, four, five or more amino acids may be substituted by a different amino acid; or
f. the heavy chain CDRs 1, 2 and 3 (HCDR1, HCDR2, HCDR3) amino acid sequences as shown in SEQ ID NOS: 16-21, wherein one, two, three, four, five or more amino acids may be substituted by a different amino acid; and the light chain CDRs 1, 2 and 3 (LCDR1, LCDR2, LCDR3) amino acid sequences as shown in SEQ ID NOS: 22-24, wherein one, two, three, four, five or more of amino acids may be substituted by a different amino acid; or g. the heavy chain variable region having CDRs 1, 2 and 3 (HCDR1, HCDR2, HCDR3) amino acid sequences which are each at least 60%, 70%, 80%, 85%, 90% or 95% identical to the CDRs 1, 2 and 3 of the variable region having an amino acid sequence of SEQ ID NO: 14, wherein one, two, three, four, five or more amino acids may be substituted by a different amino acid; or h. the light chain variable region having CDRs 1, 2 and 3 (LCDR1, LCDR2, LCDR3) amino acid sequences which are each at least 60%, 70%, 80%, 85%, 90% or 95% identical to the CDRs 1, 2 and 3 of the variable region having an amino acid sequence of SEQ ID NO: 15, wherein one, two, three, four, five or more of these amino acids may be substituted by a different amino acid.

In another aspect of any of the embodiments herein, any of the CDRs 1, 2 and 3 of the heavy and light chains may be characterized as having an amino acid sequence that shares at least 50%, 60%, 70%, 80%, 85%, 90% or 95% sequence identity with the particular CDR or set of CDRs listed in the corresponding SEQ ID NO.

In another aspect, the invention provides an antibody that competes for TLR3 binding with a monoclonal antibody of (a) to (h), above.

Antibody 32C4

The amino acid sequence of the heavy chain variable region of 32C4 is listed as SEQ ID NO: 25, the amino acid sequence of the light chain variable region is listed as SEQ ID NO: 26. In a specific embodiment, the invention provides an antibody that binds essentially the same epitope or determinant as monoclonal antibodies 32C4; optionally the antibody comprises an antigen binding region of antibody 32C4. In any of the embodiments herein, antibody 32C4 can be characterized by its amino acid sequence and/or nucleic acid sequence encoding it. In one preferred embodiment, the monoclonal antibody comprises the Fab or F(ab')2 portion of 32C4. Also provided is a monoclonal antibody that comprises the heavy chain variable region of 32C4. According to one embodiment, the monoclonal antibody comprises the three CDRs of the heavy chain variable region of 32C4. Also provided is a monoclonal antibody that further comprises the variable light chain variable region of 32C4 or one, two or three of the CDRs of the light chain variable region of 32C4. Optionally any one or more of said light or heavy chain CDRs may contain one, two, three, four or five amino acid modifications (e.g. substitutions, insertions or deletions). Optionally, provided is an antibody where any of the light and/or heavy chain variable regions comprising part or all of an antigen binding region of antibody 32C4 are fused to an immunoglobulin constant region of the IgG type, optionally a human constant region, optionally a human IgG1 or IgG4 isotype. In another preferred embodiment the antibody is 32C4.

In another aspect, the invention provides an antibody or a purified polynucleotide which encodes an antibody, wherein the antibody comprises: a VHCDR1 region comprising an amino acid sequence as set forth in SEQ ID NO: 27, 28 or 29, wherein one or more amino acids may be substituted by a different amino acid; a VHCDR2 region comprising an amino acid sequence as set forth in SEQ ID NO: 30 or 31, wherein one or more amino acids may be substituted by a different amino acid; a VHCDR3 region comprising an amino acid sequence as set forth in SEQ ID NO: 32, wherein one or more amino acids may be substituted by a different amino acid; a VLCDR1 region comprising an amino acid sequence as set forth in SEQ ID NO: 33, wherein one or more amino acids may be substituted by a different amino acid; a VLCDR2 region comprising an amino acid sequence as set forth in SEQ ID NO: 34, wherein one or more amino acids may be substituted by a different amino acid; a VLCDR3 region comprising an amino acid sequence as set forth in SEQ ID NO: 35, wherein one or more amino acids may be substituted by a different amino acid.

In another aspect, the invention provides an antibody that binds human TLR3, comprising:

a. the heavy chain variable region of SEQ ID NO: 25, wherein one, two, three or more amino acids may be substituted by a different amino acid; or b. the light chain variable region of SEQ ID NO: 26, wherein one, two, three or more amino acids may be substituted by a different amino acid; or c. the heavy chain variable region of SEQ ID NO: 25, wherein one, two, three or more amino acids may be substituted by a different amino acid; and the light chain variable region of SEQ ID NO: 26, wherein one, two, three or more amino acids may be substituted by a different amino acid; or d. the heavy chain CDRs 1, 2 and 3 (HCDR1, HCDR2, HCDR3) amino acid sequences as shown in SEQ ID NOS: 27-32, wherein one, two, three, four, five or more amino acids may be substituted by a different amino acid; or e. the light chain CDRs 1, 2 and 3 (LCDR1, LCDR2, LCDR3) amino acid sequences as shown in SEQ ID NOS: 33-35, wherein one, two, three, four, five or more amino acids may be substituted by a different amino acid; or f. the heavy chain CDRs 1, 2 and 3 (HCDR1, HCDR2, HCDR3) amino acid sequences as shown in SEQ ID NOS: 27-32, wherein one, two, three, four, five or more amino acids may be substituted by a different amino acid; and the light chain CDRs 1, 2 and 3 (LCDR1, LCDR2, LCDR3) amino acid sequences as shown in SEQ ID NOS: 33-35, wherein one, two, three, four, five or more amino acids may be substituted by a different amino acid; or g. the heavy chain variable region having CDRs 1, 2 and 3 (HCDR1, HCDR2, HCDR3) amino acid sequences which are each at least 60%, 70%, 80%, 85%, 90% or 95% identical to the CDRs 1, 2 and 3 of the variable region having an amino acid sequence of SEQ ID NO: 25, wherein one, two, three, four, five or more amino acids may be substituted by a different amino acid; or h. the light chain variable region having CDRs 1, 2 and 3 (LCDR1, LCDR2, LCDR3) amino acid sequences which are each at least 60%, 70%, 80%, 85%, 90% or 95% identical to the CDRs 1, 2 and 3 of the variable region having an amino acid sequence of SEQ ID NO: 26, wherein one, two, three, four, five or more amino acids may be substituted by a different amino acid.

In another aspect of any of the embodiments herein, any of the CDRs 1, 2 and 3 of the heavy and light chains may be characterized as having an amino acid sequence that shares at least 50%, 60%, 70%, 80%, 85%, 90% or 95% sequence identity with the particular CDR or set of CDRs listed in the corresponding SEQ ID NO.

In another aspect, the invention provides an antibody that competes for TLR3 binding with a monoclonal antibody of (a) to (h), above.

Antibody 37B7

The amino acid sequence of the heavy chain variable region of 37B7 is listed as SEQ ID NO:36, the amino acid sequence of the light chain variable region is listed as SEQ ID NO: 37. In a specific embodiment, the invention provides an antibody that binds essentially the same epitope or determinant as monoclonal antibodies 37B7; optionally the antibody comprises an antigen binding region of antibody 37B7. In any of the embodiments herein, antibody 37B7 can be characterized by its amino acid sequence and/or nucleic acid sequence encoding it. In one preferred embodiment, the monoclonal antibody comprises the Fab or F(ab')2 portion of 37B7. Also provided is a monoclonal antibody that comprises the heavy chain variable region of 37B7. According to one embodiment, the monoclonal antibody comprises the three CDRs of the heavy chain variable region of 37B7. Also provided is a monoclonal antibody that further comprises the variable light chain variable region of 37B7 or one, two or three of the CDRs of the light chain variable region of 37B7. Optionally any one or more of said light or heavy chain CDRs may contain one, two, three, four or five amino acid modifications (e.g. substitutions, insertions or deletions). Optionally, provided is an antibody where any of the light and/or heavy chain variable regions comprising part or all of an antigen binding region of antibody 37B7 are fused to an immunoglobulin constant region of the IgG type, optionally a human constant region, optionally a human IgG1 or IgG4 isotype. In another preferred embodiment the antibody is 37B7.

In another aspect, the invention provides an antibody or a purified polynucleotide which encodes an antibody, wherein the antibody comprises: a VHCDR1 region comprising an amino acid sequence as set forth in SEQ ID NO: 38, 39 or 40, wherein one or more amino acids may be substituted by a different amino acid; a VHCDR2 region comprising an amino acid sequence as set forth in SEQ ID NO: 41 or 42, wherein one or more amino acids may be substituted by a different amino acid; a VHCDR3 region comprising an amino acid sequence as set forth in SEQ ID NO: 43, wherein one or more amino acids may be substituted by a different amino acid; a VLCDR1 region comprising an amino acid sequence as set forth in SEQ ID NO: 44, wherein one or more amino acids may be substituted by a different amino acid; a VLCDR2 region comprising an amino acid sequence as set forth in SEQ ID NO: 45, wherein one or more amino acids may be substituted by a different amino acid; a VLCDR3 region comprising an amino acid sequence as set forth in SEQ ID NO: 46, wherein one or more amino acids may be substituted by a different amino acid.

In another aspect, the invention provides an antibody that binds human TLR3, comprising:
a. the heavy chain variable region of SEQ ID NO: 36, wherein one, two, three or more amino acids may be substituted by a different amino acid; or
b. the light chain variable region of SEQ ID NO: 37, wherein one, two, three or more amino acids may be substituted by a different amino acid; or
c. the heavy chain variable region of SEQ ID NO: 36, wherein one, two, three or more amino acids may be substituted by a different amino acid; and the light chain variable region of SEQ ID NO: 37, wherein one, two, three or more amino acids may be substituted by a different amino acid; or
d. the heavy chain CDRs 1, 2 and 3 (HCDR1, HCDR2, HCDR3) amino acid sequences as shown in SEQ ID NOS: 38-43, wherein one, two, three, four, five or more amino acids may be substituted by a different amino acid; or
e. the light chain CDRs 1, 2 and 3 (LCDR1, LCDR2, LCDR3) amino acid sequences as shown in SEQ ID NOS: 44-46, wherein one, two, three, four, five or more amino acids may be substituted by a different amino acid; or
f. the heavy chain CDRs 1, 2 and 3 (HCDR1, HCDR2, HCDR3) amino acid sequences as shown in SEQ ID NOS: 38-43, wherein one, two, three, four, five or more amino acids may be substituted by a different amino acid; and the light chain CDRs 1, 2 and 3 (LCDR1, LCDR2, LCDR3) amino acid sequences as shown in SEQ ID NOS: 44-46, wherein one, two, three, four, five or more amino acids may be substituted by a different amino acid; or
g. the heavy chain variable region having CDRs 1, 2 and 3 (HCDR1, HCDR2, HCDR3) amino acid sequences which are each at least 60%, 70%, 80%, 85%, 90% or 95% identical to the CDRs 1, 2 and 3 of the variable region having an amino acid sequence of SEQ ID NO: 36, wherein one, two, three, four, five or more amino acids may be substituted by a different amino acid; or
h. the light chain variable region having CDRs 1, 2 and 3 (LCDR1, LCDR2, LCDR3) amino acid sequences which are each at least 60%, 70%, 80%, 85%, 90% or 95% identical to the CDRs 1, 2 and 3 of the variable region having an amino acid sequence of SEQ ID NO: 37, wherein one, two, three, four, five or more amino acids may be substituted by a different amino acid.

In another aspect of any of the embodiments herein, any of the CDRs 1, 2 and 3 of the heavy and light chains may be characterized as having an amino acid sequence that shares at least 50%, 60%, 70%, 80%, 85%, 90% or 95% sequence identity with the particular CDR or set of CDRs listed in the corresponding SEQ ID NO.

In another aspect, the invention provides an antibody that competes for TLR3 binding with a monoclonal antibody of (a) to (h), above.

Antibody 7G11

The amino acid sequence of the heavy chain variable region of 7G11 is listed as SEQ ID NO: 47, the amino acid sequence of the light chain variable region is listed as SEQ ID NO: 48. In a specific embodiment, the invention provides an antibody that binds essentially the same epitope or determinant as monoclonal antibodies 7G11; optionally the antibody comprises an antigen binding region of antibody 7G11. In any of the embodiments herein, antibody 7G11 can be characterized by its amino acid sequence and/or nucleic acid sequence encoding it. In one preferred embodiment, the monoclonal antibody comprises the Fab or F(ab')2 portion of 7G11. Also provided is a monoclonal antibody that comprises the heavy chain variable region of 7G11. According to one embodiment, the monoclonal antibody comprises the three CDRs of the heavy chain variable region of 7G11. Also provided is a monoclonal antibody that further comprises the variable light chain variable region of 7G11 or one, two or three of the CDRs of the light chain variable region of 7G11. Optionally any one or more of said light or heavy chain CDRs may contain one, two, three, four or five amino acid modifications (e.g. substitutions, insertions or deletions). Optionally, provided is an antibody where any of the light and/or heavy chain variable regions comprising part or all of an antigen binding region of antibody 7G11 are fused to an immunoglobulin constant region of the IgG type, optionally a human constant region, optionally a human IgG1 or IgG4 isotype. In another preferred embodiment the antibody is 7G11.

In another aspect, the invention provides an antibody or a purified polynucleotide which encodes an antibody, wherein the antibody comprises: a VHCDR1 region comprising an amino acid sequence as set forth in SEQ ID NO: 49, 50 or 51, wherein one or more amino acids may be substituted by a different amino acid; a VHCDR2 region comprising an amino acid sequence as set forth in SEQ ID NO: 52 or 53, wherein one or more amino acids may be substituted by a different amino acid; a VHCDR3 region comprising an amino acid sequence as set forth in SEQ ID NO: 54, wherein one or more amino acids may be substituted by a different amino acid; a VLCDR1 region comprising an amino acid sequence as set forth in SEQ ID NO: 55, wherein one or more amino acids may be substituted by a different amino acid; a VLCDR2 region comprising an amino acid sequence as set forth in SEQ ID NO: 56, wherein one or more amino acids may be substituted by a different amino acid; a VLCDR3 region comprising an amino acid sequence as set forth in SEQ ID NO: 57, wherein one or more amino acids may be substituted by a different amino acid.

In another aspect, the invention provides an antibody that binds human TLR3, comprising:
  a. the heavy chain variable region of SEQ ID NO: 47, wherein one, two, three or more amino acids may be substituted by a different amino acid; or
  b. the light chain variable region of SEQ ID NO: 48, wherein one, two, three or more amino acids may be substituted by a different amino acid; or
  c. the heavy chain variable region of SEQ ID NO: 47, wherein one, two, three or more amino acids may be substituted by a different amino acid; and the light chain variable region of SEQ ID NO: 48, wherein one, two, three or more amino acids may be substituted by a different amino acid; or
  d. the heavy chain CDRs 1, 2 and 3 (HCDR1, HCDR2, HCDR3) amino acid sequences as shown in SEQ ID NOS: 49-54, wherein one, two, three, four, five or more amino acids may be substituted by a different amino acid; or
  e. the light chain CDRs 1, 2 and 3 (LCDR1, LCDR2, LCDR3) amino acid sequences as shown in SEQ ID NOS: 55-57, wherein one, two, three, four, five or more amino acids may be substituted by a different amino acid; or
  f. the heavy chain CDRs 1, 2 and 3 (HCDR1, HCDR2, HCDR3) amino acid sequences as shown in SEQ ID NOS: 49-54, wherein one, two, three, four, five or more amino acids may be substituted by a different amino acid; and the light chain CDRs 1, 2 and 3 (LCDR1, LCDR2, LCDR3) amino acid sequences as shown in SEQ ID NOS: 55-57, wherein one, two, three, four, five or more amino acids may be substituted by a different amino acid; or
  g. the heavy chain variable region having CDRs 1, 2 and 3 (HCDR1, HCDR2, HCDR3) amino acid sequences which are each at least 60%, 70%, 80%, 85%, 90% or 95% identical to the CDRs 1, 2 and 3 of the variable region having an amino acid sequence of SEQ ID NO: 47, wherein one, two, three, four, five or more amino acids may be substituted by a different amino acid; or
  h. the light chain variable region having CDRs 1, 2 and 3 (LCDR1, LCDR2, LCDR3) amino acid sequences which are each at least 60%, 70%, 80%, 85%, 90% or 95% identical to the CDRs 1, 2 and 3 of the variable region having an amino acid sequence of SEQ ID NO: 48, wherein one, two, three, four, five or more amino acids may be substituted by a different amino acid.

In another aspect of any of the embodiments herein, any of the CDRs 1, 2 and 3 of the heavy and light chains may be characterized as having an amino acid sequence that shares at least 50%, 60%, 70%, 80%, 85%, 90% or 95% sequence identity with the particular CDR or set of CDRs listed in the corresponding SEQ ID NO.

In another aspect, the invention provides an antibody that competes for TLR3 binding with a monoclonal antibody of (a) to (h), above.

CDR sequences for antibodies 7G11 and 32C4 are derived from VL and VH gene rearrangements of the rat IGKV12s30*01 and IGHV1s6*01 genes for the light and heavy chains, respectively. CDR sequences for the heavy chain of antibody 31F6 are also derived from a VH gene rearrangement of the rat IGHV1s6*01 gene while the light chain CDR sequence are derived from a VL gene rearrangement the rat IGKV12s8*0 gene. In one aspect of the invention, the light chain of one antibody according to the present invention is obtained from or encoded by a nucleic acid sequence derived from a VL gene rearrangement selected from IGKV12s30*01 and IGKV12s8*0 for the V gene. In one aspect of the invention, the heavy chain of one antibody according to the present invention is obtained from or encoded by a nucleic acid sequence derived from a VH gene rearrangement selected from IGHV1 s6*01 for the V gene.

In any of the antibodies of the invention, e.g., 11E1, 7G11, 31F6, 32C4 or 37B7, the specified variable region and CDR sequences may comprise conservative sequence modifications. Conservative sequence modifications refers to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are typically those in which an amino acid residue is replaced with an amino acid residue having a side chain with similar physicochemical properties. Specified variable region and CDR sequences may comprise one, two, three, four or more amino acid insertions, deletions or substitutions. Where substitutions are made, preferred substitutions will be conservative modifications. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g. threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the properties set forth herein) using the assays described herein.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

The sequences of the CDRs of the antibodies according to the invention, according to AbM (Oxford Molecular's AbM antibody modelling software definition), Kabat and Chothia definitions systems, have been summarized in Tables 1 and 2 below. The amino acids sequences described herein are numbered according to Abm, Kabat and Chothia numbering systems. While any suitable numbering system may be used to designated CDR regions, in the absence of any other indication, Abm numbering can be used. Such numbering has been established using the following indications: CDR-L1: Start: approx. residue 24, residue before: always a Cys, residue after: always a Trp (typically Trp-Tyr-Gln, but also, Trp-Leu-Gln, Trp-Phe-Gln, Trp-Tyr-Leu), length: 10 to 17 residues; CDR-L2: Start: always 16 residues after the end of L1, Residues before: generally Ile-Tyr (but also, Val-Tyr, Ile-Lys, Ile-Phe), Length: always 7 residues; CDR-L3, Start: always 33 residues after end of L2, Residue before: always Cys, Residues after: always Phe-Gly-Xaa-Gly, Length: 7 to 11 residues; CDR-H1, Start: approx. residue 26 (always 4 after a Cys) (Chothia/AbM definition, the Kabat definition starts 5 residues later), Residues before: always Cys-Xaa-Xaa-Xaa, Residues after: always a Trp (typically Trp-Val, but also, Trp-Ile, Trp-Ala), Length: 10 to 12 residues (AbM definition, Chothia definition excludes the last 4 residues); CDR-H2, Start: always 15 residues after the end of Kabat/AbM definition of CDR-H1, Residues before: typically Leu-Glu-Trp-Ile-Gly (but a number of variations, Residues after Lys/Arg-Leu/Ile/Val/Phe/Thr/Ala-Thr/Ser/Ile/Ala), Length: Kabat definition 16 to 19 residues; AbM (and Chothia) definition ends 7 residues earlier; CDR-H3, Start: always 33 residues after end of CDR-H2 (always 2 after a Cys), Residues before: always Cys-Xaa-Xaa (typically Cys-Ala-Arg), Residues after: always Trp-Gly-Xaa-Gly, Length: 3 to 25 residues.

In an embodiment, the antibodies of the invention are of the human or mouse IgG1 isotype. In another embodiment, the antibodies of the invention are of the human IgG4 isotype. In an embodiment, the antibodies of the invention are antibody fragments that retain their binding and/or functional properties.

TABLE 1

| mAb | CDR definition | HCDR1 SEQ ID | Sequence | HCDR2 SEQ ID | Sequence | HCDR3 SEQ ID | Sequence |
|---|---|---|---|---|---|---|---|
| 11E1 | Kabat | 5 | NYWMN | 8 | MIDPSDSETH YNQMFKD | 10 | GASSDYYYFDY |
|  | Chotia | 6 | GYTFTN | 9 | MIDPSDSETH |  | GASSDYYYFDY |
|  | Abm | 7 | GYTFTN YWMN |  | MIDPSDSETH |  | GASSDYYYFDY |
| 31F6 | Kabat | 16 | YTYMH | 19 | RIDPANGDSI YGEDFKT | 21 | GEFDYFDY |
|  | Chotia | 17 | GYNIRY | 20 | RIDPANGDSI |  | GEFDYFDY |
|  | Abm | 18 | GYNIRY TYMH |  | RIDPANGDSI |  | GEFDYFDY |
| 32C4 | Kabat | 27 | STYIY | 30 | RIDPANGNTI YAEKFKT | 32 | GDHGGYVMDA |
|  | Chotia | 28 | GYNIWS | 31 | RIDPANGNTI |  | GDHGGYVMDA |
|  | Abm | 29 | GYNIWS TYIY |  | RIDPANGNTI |  | GDHGGYVMDA |
| 37B7 | Kabat | 38 | SNYMH | 41 | WIFPGDGDTN YNQKFNG | 43 | SDGDWYFDF |
|  | Chotia | 39 | GYTFTS | 42 | WIFPGDGDTN |  | SDGDWYFDF |
|  | Abm | 40 | GYTFTS NYMH |  | WIFPGDGDTN |  | SDGDWYFDF |
| 7G11 | Kabat | 49 | YTYMH | 52 | RIDPANGNTI YGEKFKN | 54 | GEFDYFDH |
|  | Chotia | 50 | GYNITY | 53 | RIDPANGNTI |  | GEFDYFDH |
|  | Abm | 51 | GYNITY TYMH |  | RIDPANGNTI |  | GEFDYFDH |

TABLE 2

| mAb | CDR definition | LCDR1 SEQ ID | Sequence | LCDR2 SEQ ID | Sequence | LCDR3 SEQ ID | Sequence |
|---|---|---|---|---|---|---|---|
| 11E1 | Abm Chotia Kabat | 11 | ITSTDIHDDIN | 12 | EGNTLRP | 13 | LQSDNLPRT |
| 31F6 | Abm Chotia Kabat | 22 | LASEGISNDLA | 23 | AASRLQD | 24 | QQNYKYPLT |
| 32C4 | Abm Chotia Kabat | 33 | LASEDIYS YLA | 34 | AANRLED | 35 | LQGSEFPYT |
| 37B7 | Abm Chotia Kabat | 44 | QASEDIYS GLA | 45 | AASRLQD | 46 | QQGVKYPNT |
| 7G11 | Abm Chotia Kabat | 55 | LASEDISNDLA | 56 | AASRLED | 57 | QQSYKYPVT |

TABLE 3

| Antibody portion | SEQ ID NO: | Variable region amino acid sequence |
|---|---|---|
| 11E1 VH | 3 | Q V Q L Q Q P G A E L V R P G A S V K L S C K A S G Y T F T N Y W M N W V K Q R P G Q G L E W I G M I D P S D S E T H Y N Q M F K D K A T L T V D K S S S T A Y M Q L S S L T S E D S A V Y Y C A R G G A S S D Y Y F D Y W G Q G T T L T V S S A S T K |
| 11E1 VL | 4 | E T T V T Q S P A S L S M A I G E K V T I R C I T S T D I H D D I N W Y Q Q K P G E P P K L L I S E G N T L R P G V P S R F S S S G Y G T D F V F T I E N M L S E D V A D Y Y C L Q S D N L P R T F G G G T K L E I K R T |
| 31F6 VH | 14 | E V Q L Q Q S G A E L G K P G T S V K L S C K V S G Y N I R Y T Y M H W V N Q R P G K G L E W I G R I D P A N G D S I Y G E D F K T K A T L T A D T S S N T A Y M Q L S Q L K S D D T A I Y F C A M G E F D Y F D Y W G Q G V M V T V S S A S T K |
| 31F6 VL | 15 | D I Q M T Q S P P S L S A S L G E T V S I E C L A S E G I S N D L A W Y Q Q R S G K S P Q L L I Y A A S R L Q D G V P S R F S G S G S G T R Y S L K I S G M Q P E D E A D Y F C Q Q N Y K Y P L T F G S G T K L E I K |
| 32C4 VH | 25 | E V Q L Q Q Y G A E L G K P G T S V K L S C K V S G Y N I W S T Y I Y W V N Q R P G K G L E W I G R I D P A N G N T I Y A E K F K T K A T L T A D T S S N T A Y M Q L S Q L K S D D T A I Y F C A M G D H G G Y V M D A W G Q G A S V T V S S |
| 32C4 VL | 26 | D I Q M T Q S P G S L S A S L G E T V S I E C L A S E D I Y S Y L A W Y Q K P G K S P Q L L I Y A A N R L E D G V P S R F S G S G S G T Q Y S L K I S G M Q P E D E G D Y F C L Q G S E F P Y T F G T G T K L E L K |
| 37B7 VH | 36 | Q V Q L Q Q S G T E L V K P G S S V K I S C K A S G Y T F T S N Y M H W I R Q L P G N G L E W I G W I F P G D G D T N Y N Q K F N G K A T L T A D K S S S T A Y M Q L S S L T S E D Y A V Y F C A R S D G D W Y F D F W G P G T M V T V S S |
| 37B7 VL | 37 | D I Q M T Q S P G S L S A S L G E T V T I Q C Q A S E D I Y S G L A W Y Q Q K P R K S P Q L L I S A A S R L Q D G V P S R F S G S G S G T Q Y S L K I S S M Q T E D E G V Y F C Q Q G V K Y P N T F G P G T K L E L K |
| 7G11 VH | 47 | E V Q L Q Q Y G A E L G K P G T S V K L S C K V S G Y N I T Y T Y M H W V N Q R P G K G L E W I G R I D P A N G N T I Y G E K F K N K A T L T A D T S S N T A Y M Q L S Q L K S D D T A I Y F C A M G E F D Y F D H W G Q G V M V T V S S |
| 7G11 VL | 48 | D I Q M T Q S P A S L S A S L G E T V S I E C L A S E D I S N D L A W Y Q Q K S G K S P Q V L I Y A A S R L E D G V P S R F S G S G S G T R Y S L K I S G M Q P E D E A D Y F C Q Q S Y K Y P V T F G S G T K L E I K |

Fragments and Derivatives of the present Monoclonal Antibodies

Fragments and derivatives of antibodies of this invention (which are encompassed by the term "antibody" or "antibodies" as used in this application, unless otherwise stated or clearly contradicted by context), preferably a 11E1, 7G11, 31F6, 32C4 or 37B7-like antibody, can be produced by techniques that are known in the art. "Fragments" comprise a portion of the intact antibody, generally the antigen binding site or variable region. Examples of antibody fragments include Fab, Fab', Fab'-SH, F (ab') 2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments. Included, inter alia, are a nanobody, domain antibody, single domain antibody or a "dAb".

Fragments of the present antibodies can be obtained using standard methods. For instance, Fab or F (ab') 2 fragments may be produced by protease digestion of the isolated antibodies, according to conventional techniques. It will be appreciated that immunoreactive fragments can be modified using known methods, for example to slow clearance in vivo and obtain a more desirable pharmacokinetic profile the fragment may be modified with polyethylene glycol (PEG). Methods for coupling and site-specifically conjugating PEG to a Fab' fragment are described in, for example, Leong et al, 16 (3): 106-119 (2001) and Delgado et al, Br. J. Cancer 73 (2): 175-182 (1996), the disclosures of which are incorporated herein by reference.

Alternatively, the DNA of a hybridoma producing an antibody of the invention, preferably a 11E1, 7G11, 31F6, 32C4 or 37B7-like antibody, may be modified so as to encode a fragment of the invention. The modified DNA is then inserted into an expression vector and used to transform or transfect an appropriate cell, which then expresses the desired fragment.

In certain embodiments, the DNA of a hybridoma producing an antibody of this invention, preferably a 11E1, 7G11, 31F6, 32C4 or 37B7-like antibody, can be modified prior to insertion into an expression vector, for example, by substituting the coding sequence for human heavy- and light-chain constant domains in place of the homologous non-human sequences (e.g., Morrison et al., PNAS pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody of the invention.

Thus, according to another embodiment, the antibody of this invention, preferably a 11E1, 7G11, 31F6, 32C4 or 37B7-like antibody, is humanized. "Humanized" forms of antibodies according to this invention are specific chimeric immunoglobulins, immunoglobulin chains or fragments thereof (such as Fv, Fab, Fab', F (ab') 2, or other antigen-binding subsequences of antibodies) which contain minimal sequence derived from the murine or rat immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody.

In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature, 321, pp. 522 (1986); Reichmann et al, Nature, 332, pp. 323 (1988); Presta, Curr. Op. Struct. Biol., 2, pp. 593 (1992); Verhoeyen et Science, 239, pp. 1534; and U.S. Pat. No. 4,816,567, the entire disclosures of which are herein incorporated by reference.) Methods for humanizing the antibodies of this invention are well known in the art.

The choice of human variable domains, both light and heavy, to be used in making the humanized antibodies is very important to reduce antigenicity. According to the so-called "best-fit" method, the sequence of the variable domain of an antibody of this invention is screened against the entire library of known human variable-domain sequences. The human sequence which is closest to that of the mouse is then accepted as the human framework (FR) for the humanized antibody (Sims et al., J. Immunol. 151, pp. 2296 (1993); Chothia and Lesk, J. Mol. 196, 1987, pp. 901). Another method uses a particular framework from the consensus sequence of all human antibodies of a particular subgroup of light or heavy chains. The same framework can be used for several different humanized antibodies (Carter et al., PNAS 89, pp. 4285 (1992); Presta et al., J. Immunol., 151, p. 2623 (1993)).

It is further important that antibodies be humanized with retention of high affinity for TLR3 receptors and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen (s), is achieved. In general, the CDR residues are directly and most substantially involved in influencing antigen binding.

Another method of making "human" monoclonal antibodies is to use a XenoMouse (Abgenix, Fremont, Calif.) as the mouse used for immunization. A XenoMouse is a murine host according to this invention that has had its immunoglobulin genes replaced by functional human immunoglobulin genes. Thus, antibodies produced by this mouse or in hybridomas made from the B cells of this mouse, are human (or already humanized). The XenoMouse is described in U.S. Pat. No. 6,162,963, which is herein incorporated in its entirety by reference.

Human antibodies may also be produced according to various other techniques, such as by using, for immunization, other transgenic animals that have been engineered to express a human antibody repertoire (Jakobovitz et Nature 362 (1993) 255), or by selection of antibody repertoires using phage display methods. Such techniques are known to the skilled person and can be implemented starting from monoclonal antibodies as disclosed in the present application.

The antibodies of the present invention, preferably a 11E1, 7G11, 31F6, 32C4 or 37B7-like antibody, may also be derivatized to "chimeric" antibodies (immunoglobulins) in which a portion of the heavy/light chain(s) is identical with or homologous to corresponding sequences in the original antibody, while the remainder of the chain (s) is identical with or homologous to corresponding sequences in antibodies derived from another species or belonging to another antibody class or subclass, as well as fragments of such antibodies, so long as they exhibit the desired biological activity and binding specificity (Cabilly et al., supra; Morrison et al., Proc. Natl. Acad. Sci. U.S.A., pp. 6851 (1984)).

Dosing Regimens

Based on efficacy data collected during in vivo experiments using anti-TLR3 antibodies, the inventors have established that a dose as low as 100 µg/mouse produces a therapeutic effect. Such dosage is equivalent to 4 mg/kg in the mouse and therefore 0.5 mg/kg in a human subject. Therefore, in the methods of the invention, the anti TLR3-antibody can be administered at a dosage comprised between 0.05 and 20 mg/kg in human, preferably 0.1 and 10 mg/kg, further preferably between 0.5 and 5 mg/kg (for example a unit dose of between about 25 mg and 500 mg).

An exemplary treatment regime entails administration twice per week, once per week, once every two weeks, once every three weeks, once every four weeks, once a month, once every 2 to 3 months, or once every 3 to 6 months. Exemplary dosage regimens for an anti-TLR3 antibody include between 0.05 and 20 mg/kg (preferably 0.1 and 10 mg/kg, further preferably between 0.5 and 5 mg/kg) body weight body weight via intravenous administration or subcutaneous injection, with the antibody being given using one of the following dosing schedules: (i) loading doses about every 1, 2, 3 of 4 weeks (e.g., for 2-4 dosages), then every one to three months; (ii) once per month or once per two month period; (iii) every one to two weeks, or any other optimal dosing.

The anti-TLR3 antibody is optionally administered at a dose that is suitable to induce substantially full TLR3 receptor saturation (90%, optionally 95% receptor saturation), e.g. saturation of TLR3 polypeptide expressed in targeted cells. As the TLR3 receptor is thought to dimerize before signaling, an inhibition of less than fully saturation by at least 20%, 30%, 40%, 50% receptor saturation may be useful in the treatment of a disease. In one embodiment, a dose of anti-TLR3 antibody resulting in at least about 20%, 30%, 40%, 50%, 90% or 95% receptor saturation is administered from about 2 times per week to about once per month, or from about once per month to about once per 2 months. The dose can be, e.g., administered at least 3 times, at least 6 times, or more. For example, the method may comprise administering an anti-TLR3 antibody at a dose and a dosing frequency achieving at least about 20%, 30%, 40%, 50%, 90% or 95% TLR3 receptor saturation on targeted cells for at least about two weeks, one month, 6 months, 9 months or 12 months. In one preferred embodiment, a regimen results in sustained substantially full receptor saturation. A dose of anti-TLR3 antibody resulting in substantially full receptor saturation for a period of at least about 1 week, 2 weeks or 1 month is administered.

Receptor occupancy can be evaluated on human samples where target cells are present (e.g. whole blood, any tissue which is the site of an inflammation, synovial fluid). Saturation percentage of the TLR3 receptor can be measured by FACS analysis using methods known in the art, via intracellular staining since the TLR3 receptor is present in the cells. Alternatively, saturation percentage can be determined using a test of cytokine inhibition secretion profile in response to a TLR3 ligand such as a dsRNA (i.e. polyAU) in mononuclear cells (preferable PBMCs) obtained from a patient. An efficient cytokine inhibition is correlated with an efficient therapeutic effect and the dosage can then be adapted for each patient. Cytokines that can be measured in this assay are for instance IP-10 or IL-6. In another embodiment, receptor saturation is assessed as receptor occupancy, for example by conducting free site and bound site assays. Briefly, free and bound TLR3 receptor levels are assessed on target cells from a biological sample obtained from an individual treated with the anti-TLR3 antibody, where a free site assay assesses unbound TLR3 by staining with PE-conjugated form of the anti-TLR3 antibody administered to an individual. A bound site assay assesses TLR3 polypeptides occupied by anti-TLR3 antibody by staining with a PE-conjugated mouse anti-human IgG4 monoclonal antibody (when the anti-TLR3 antibody is of human IgG4 isotype) that recognizes the anti-TLR3 antibody bound to the TLR3 polypeptides. In one embodiment, the invention further provides a method for treating an individual comprising: (a) administering an anti-TLR3 antibody to an individual and (b) determining TLR3 receptor saturation in the individual, optionally further determining a dosage of anti-TLR3 antibody to be administered to the individual.

Dosage Forms

Therapeutic formulations of the antagonists used in accordance with the present invention are prepared for storage by mixing the antagonist having the desired degree of purity with optional pharmaceutically acceptable carriers, excipients, or stabilizers in the form of lyophilized formulations or aqueous solutions. For general information concerning formulations, see, e.g., Gilman et al. (eds.), The Pharmacological Bases of Therapeutics, 8$^{th}$ Ed. (Pergamon Press, 1990); Gennaro (ed.), Remington's Pharmaceutical Sciences, 18$^{th}$ Edition (Mack Publishing Co., Easton, Pa., 1990); Avis et al. (eds.), Pharmaceutical Dosage Forms: Parenteral Medications (Dekker, New York, 1993); Lieberman et al. (eds.), Pharmaceutical Dosage Forms: Tablets (Dekker, New York, 1990); Lieberman et al. (eds.) Pharmaceutical Dosage Forms: Disperse Systems (Dekker, New York, 1990); and Walters (ed.), Dermatological and Transdermal Formulations (Drugs and the Pharmaceutical Sciences), Vol 119 (Dekker, New York, 2002).

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low-molecular-weight (less than about 10 residues) polypeptides; proteins such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as ethylenediaminetetraacetic acid (EDTA); sugars such as sucrose, mannitol, trehalose, or sorbitol; salt-forming counter-ions such as sodium; metal complexes (e.g., Zn-protein complexes); and/or non-ionic surfactants such as TWEEN™, PLURONICS™, or PEG.

Exemplary antibody formulations are described for instance in WO 1998/56418, which describes a liquid multidose formulation for an anti-CD20 antibody, comprising 40 mg/mL rituximab, 25 mM acetate, 150 mM trehalose, 0.9% benzyl alcohol, and 0.02% polysorbate20™ at pH 5.0 that has a minimum shelf life of two years storage at 2-8° C. Another anti-CD20 formulation of interest comprises 10 mg/mL rituximab in 9.0 mg/mL sodium chloride, 7.35 mg/mL sodium citrate dihydrate, 0.7 mg/mL polysorbate80™, and Sterile Water for Injection, pH 6.5.

Lyophilized formulations adapted for subcutaneous administration are described, for example, in U.S. Pat. No. 6,267,958 (Andya et al.). Such lyophilized formulations may be reconstituted with a suitable diluent to a high protein concentration and the reconstituted formulation may be administered subcutaneously to the mammal to be treated herein.

Crystallized forms of the antagonist are also contemplated. See, for example, US 2002/0136719A1 (Shenoy et al.).

The formulation herein may also contain more than one active compound (a second medicament as noted above), preferably those with complementary activities that do not adversely affect each other. The type and effective amounts of such medicaments depend, for example, on the amount and type of B-cell antagonist present in the formulation, and clinical parameters of the subjects. The preferred such second medicaments are noted above.

The active ingredients may also be entrapped in microcapsules prepared, e.g., by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's Pharmaceutical Sciences, supra, for example.

Sustained-release formulations may be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes. Pharmaceutically acceptable carriers that may be used in these compositions include, but are not limited to, ion exchangers, alumina, aluminium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. The antibodies of this invention may be employed in a method of modulating, e.g. inhibiting, the activity of TLR3-expressing cells in a patient. This method comprises the step of contacting a patient with said composition (e.g. administering said composition to the patient). Such method will be useful for both prophylaxis and therapeutic purposes.

Formulations may be adapted to nasal or inhalation routes. A formulation may comprise a pharmaceutically acceptable nasal carrier. For nasal delivery, any well-known delivery methods such as drops, a nasal spray, a nasal liquid or powder aerosol, a capsule or a nasal insert can be used. For aerosol delivery, any well-known delivery methods such as a nebulizer, inhaler, atomizer, aerosolizer, mister, dry powder inhaler, metered dose inhaler, metered dose sprayer, metered dose mister, metered dose atomizer, or other suitable delivery device can be used.

Further aspects and advantages of this invention will be disclosed in the following experimental section, which should be regarded as illustrative and not limiting the scope of this application.

Treatment of Disease

The present invention provides methods for the treatment of an individual having an autoimmune or inflammatory disease, comprising administering to the individual an anti-TLR3 antibody of the invention. The antibody may be comprised in a composition that further comprises a pharmaceutically acceptable carrier. Such compositions are also referred to as "antibody compositions" of the invention. In one embodiment, antibody compositions of this invention comprise an antibody disclosed in the antibody embodiments above.

The invention further provides a method of modulating TLR3-expressing cell activity in a patient in need thereof, comprising the step of administering to said patient a composition according to the invention. The method is more specifically directed at decreasing TLR3 cell activity in patients having a disease in which decreased TLR3 cell activity is beneficial (e.g., autoimmune diseases, inflammatory diseases, infectious disease, viral infection), or which is caused or characterized by excessive TLR3 cell activity. In one embodiment, the TLR3-expressing cell activity is inhibited, wherein the patient has a disease or disorder wherein such inhibition may promote, enhance, and/or induce a therapeutic effect (or promotes, enhances, and/or induces such an effect in at least a substantial proportion of patients with the disease or disorder and substantially similar characteristics as the patient, as may be determined by, e. g., clinical trials).

Diseases and conditions in which the present methods can be used include all diseases where modulating TLR3 can be beneficial, including for example diseases mediated or exacerbated partially or totally by TLR3 signaling or by cytokines produced upon said TLR3 signaling. In particular, where antibodies that inhibit TLR3 signaling are used, such disorders include any disorders mediated or exacerbated partially or totally by TLR3 signaling or by cytokines produced upon said TLR3 signaling, including inter alia immune disorders such as inflammatory diseases and autoimmune diseases. More specifically, the methods of the present invention are utilized for the treatment of a variety of immune disorders and other diseases including, but not limited to autoimmunity, inflammation, allergy, asthma, infections (e.g. chronic infection, viral infection) and sepsis. Examples of diseases which can be treated with the antibodies that inhibit TLR3 signaling include, but are not limited to arthritis, systemic lupus erythematosus, sepsis, asthma, osteoporosis, autoimmunity to central nervous system antigens, autoimmune diabetes, inflammatory bowel disease, autoimmune carditis and autoimmune hepatitis.

In a further embodiment, an anti-TLR3 antibody of the invention that inhibitors signalling by a TLR3 polypeptide is used for the treatment or prevention of graft-versus-host disease (GvHD), e.g. in transplantation or transfusions. Particularly, after bone marrow transplantation, T cells present in the graft, either as contaminants or intentionally introduced into the host, attack the tissues of the transplant recipient after perceiving host tissues as antigenically foreign. The T cells produce an excess of cytokines, including TNF-α and interferon-gamma (IFNγ). Anti-TLR3 antibodies can be administered before, during or following a transplantation or transfusion, e.g. allogeneic bone marrow transplantation, particularly in the treatment of cancer, for example leukemias. The antibody may be any anti-TLR3 antibody that inhibits signalling of a TLR3 polypeptide. Since GvHD is believed to be largely driven by antigen presenting cells, anti-TLR3 antibodies that inhibit TLR3 signalling in DC are believed to be particularly useful.

Other immune disorders treatable using the antibodies that inhibit TLR3 signaling according to the invention include, inter alia, autoimmune disorders and inflammatory disorders, including, but not limited to, Crohn's disease, Celiac disease, ulcerative colitis, irritable bowel syndrome, acute disseminated encephalomyelitis (ADEM), Addison's disease, antiphospholipid antibody syndrome (APS), aplastic anemia, autoimmune hepatitis, Diabetes mellitus, Goodpasture's syndrome, Graves' disease, Guillain-Barré syndrome (GBS), Hashimoto's disease, lupus erythematosus, demyelinating conditions, Multiple sclerosis, Myasthenia gravis, opsoclonus myoclonus syndrome (OMS), optic neuritis, Ord's thyroiditis, pemphigus, cirrhosis, psoriasis, rheumatoid arthritis, Reiter's syndrome, Takayasu's arteritis, temporal arteritis, warm autoimmune hemolytic anemia, Wegener's granulomatosis, appendicitis, arteritis, arthritis, blepharitis, bronchiolitis, bronchitis, bursitis, cervicitis, cholangitis, cholecystitis, chorioamnionitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, gingivitis, hepatitis, hidradenitis suppurativa, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, and vulvitis.

One aspect of the invention is to provide a composition which is able to treat a SIRS, a sepsis, a severe sepsis or a septic shock. Another aspect of the invention is to provide a method for the prophylactic treatment of patients who is at risk of developing a sepsis. For instance, patients that have had their spleen surgically removed, patients with an impaired immune system (i.e. chemotherapy treatment, immunodepression) but also other causes such as long term steroids medication, diabetes, AIDS, or cirrhosis, large burns or severe injuries, infections such as pneumonia, meningitis, peritonitis, appendicitis, cellulitis, urinary tract infection or infections occurring after a major surgical act.

In one embodiment, the individual has an autoimmune or inflammatory disease that has been declared for an extended period of time (e.g. more than one year), has signs of ongoing or active inflammation, has physical signs of disease (e.g. joint swelling, lesions, neurological symptoms, etc.), has chronic disease, has severe disease (as assessed by applicable criteria, e.g. DAS or ACR criteria in rheumatoid arthritis) or has progressing disease.

In one embodiment, the present invention provides methods for the treatment of an individual having an established autoimmune or inflammatory disease, comprising administering to the individual an anti-TLR3 antibody. In one embodiment, the present invention provides methods for the treatment of acute phases, or of an attack, crisis, exacerbation or flare, of autoimmune or inflammatory diseases using a TLR3 antibody (or related compositions), preferably wherein the antibody is administered to an individual during an acute phase or during an attack, crisis, exacerbation or flare of an autoimmune or inflammatory disease. In one embodiment, the disease is selected from the group consisting of rheumatoid arthritis, Juvenile idiopathic arthritis, multiple sclerosis, Crohn's disease or rectocolitis, Lupus erythematosus, hepatitis, chronic obstructive pulmonary disease (COPD) or asthma, ankylosing spondylitis and related diseases. In one embodiment, the disease is characterized by the presence of a TLR3 ligand (e.g. extracellular dsRNA). In one embodiment, the disease is characterized by the presence of detectable levels of a proteolytic enzyme, an inflammatory mediator, a marker of ongoing inflammation or a proinflammatory cytokine (e.g. TNF-α and/or interleukin-1 (IL-1)). Preferably the antibody inhibits signaling by the TLR3 polypeptide, optionally further in acid conditions and with high binding affinity, optionally in a human dendritic cell.

Treatment generally involves the delivery of an effective amount of a composition comprising an anti-TLR3 antibody with the purpose of preventing any symptoms or disease state to develop or worsen, or with the purpose of preventing (e.g. preventing or postponing progression), easing, ameliorating, or eradicating (curing) such symptoms or disease states already developed. Disease diagnosis, evolution and rating (or staging) can be defined by standard medical criteria for the particular type of disease in order to determine whether an individual has disease that is established, is in an acute phase, is progressing, is chronic, has physical symptoms, or is of a certain level of severity. Likewise, attack, crisis, exacerbation or flares can be identified by any suitable medical criteria.

In one embodiment, the invention will comprises a step of conducting an evaluation or testing step to assess the presence, stage, evolution or rating of disease. Thus, in one aspect, the invention provides a method for the treatment of an autoimmune or inflammatory disease in a patient, comprising: (a) conducting an evaluation of disease in the patient; and (b) if said patient has a disease suitable for treatment with an anti-TLR3 antibody of the invention, administering to said patient an effective dose of anti-TLR3 antibody. Optionally such evaluation step may involve obtaining a biological sample from a patient suspected of having an autoimmune or inflammatory disease. Methods for evaluating disease (e.g. diagnosing, staging, etc.) can be achieved by any suitable technique known in the art, for example by performing a laboratory-based test. Examples of suitable techniques include conducting a PCR or RT-PCR based assay (e.g., to detect disease associated nucleic acids or genes, often referred to as "markers" or "biomarkers"), biopsy, endoscopy, stool studies, any noninvasive laboratory tests (e.g. anemia and infection, liver function tests to screen for liver and bile duct problems, tests for bacterial, viral and parasitic infections), ultrasound, CT, MRE, MRI and other imaging techniques, chromosomal analysis, immunoassay/immunocytochemical detection techniques (e.g. presence of autoantibodies), histological and/or histopathologic assays, serum protein electrophoresis, flow cytometry (e.g. detection of immune cells, T cells, etc.), arterial blood gas (ABG) analysis (in asthma or COPD), and physical examination techniques (e.g., for physical symptoms, numbers of joints with synovitis, etc.). In one embodiment, the methods comprise detecting the presence of auto-antibodies, for example detecting rheumatoid factor (RhF), anti-cyclic citrullinated peptide antibodies, anti-ssRNA, anti-dsRNA, anti-Smith, anti-phospholipid, anti-nuclear and/or anti-actin antibodies. In one embodiment, the methods comprise assessing levels of a proteolytic enzyme, an inflammatory mediator, a marker of ongoing inflammation or a proinflammatory cytokine. In one embodiment, the methods comprise determining c-reactive protein (CRP) level and/or erythrocyte sedimentation rate. A determination that an individual has abnormal results (indicative of disease, exacerbation, ongoing inflammation, etc.), for example abnormal levels of ABG, autoantibodies, CRP, any proteolytic enzyme, inflammatory mediator or marker of ongoing inflammation indicates the individual is suitable for treatment with an anti-TLR3 antibody.

Delivering anti-TLR3 antibodies to a subject (either by direct administration or expression from a nucleic acid therein, such as from a pox viral gene transfer vector comprising anti-TLR3 antibody-encoding nucleic acid sequence(s)) and practicing the other methods of the invention can be used to reduce, treat, prevent, or otherwise ameliorate any suitable aspect of disease or disease progression. The methods of the invention can be particularly useful in the reduction and/or amelioration of inflammation and/or tissue damage, and any parameter or symptom associated therewith (e.g. the presence of a marker of inflammation, number of pro-inflammatory cells in circulation or in a particular tissue).

Anti-TLR3 antibodies can advantageously be used to treat established disease. "Established disease" refers to an autoimmune or inflammatory disease which has been declared for an extended period of time, e.g. more than one year. Depending on the specific disease, established disease also means a disease which is not controlled e.g. which is still progressing or for which the patient does not experience remission, in the presence or in the absence of a treatment. In one aspect, the invention provides a method for the treatment of an autoimmune or inflammatory disease in a patient, comprising: (a) determining whether said patient has an established disease; and (b) if said patient has an established diseases, administering to said patient an effective dose of anti-TLR3 antibody.

Anti-TLR3 antibodies can also advantageously be used to treat chronic disease. "Chronic disease" refers to a disease that persists for an extended period of time. For instance, a chronic disease can be a disease lasting 3 months or more, as defined by the U.S. National Center for Health Statistics. In one aspect, the invention provides a method for the treatment of an autoimmune or inflammatory disease in a patient, comprising: (a) determining whether said patient has chronic disease; and (b) if said patient has chronic diseases, administering to said patient an effective dose of anti-TLR3 antibody.

Anti-TLR3 antibodies can also advantageously be used to treat individuals having an attack, crisis, exacerbation or flare. The terms "attack", "crisis", "exacerbation" and "flare", designate a more rapid evolution of new symptoms or worsening of old symptoms related to an inflammatory or an autoimmune disease. Such phases last over a period of hours or days, as opposed to a slow progression of the disease that occurs over months and years. During such attacks, the patient experiences fever, pain, inflammatory syndrome (flu-like syndrome). In RA, the joints of the patient are swollen and painful. The patient can experience flu-like syndromes. A crisis can last from a few hours to many weeks. In Multiple Sclerosis, flare-ups can feature a new symptom or the worsening of an existing symptom but must last at least 24 hours to be considered a true exacerbation, a flare up denotes new lesions forming in the brain or spinal cord that disrupt neural transmission. Most flare-ups last a few days or weeks but can last for several months. Effects can for instance be: movement difficulties or spasms, balance and coordination problems; vision problems, unco-ordinated eye movements, blurred vision or double vision, partial blindness during a flare-up; bladder and bowel symptoms; sexual problems, changes in mental function: memory loss, inattention and poor judgment or depression. In COPD, an exacerbation can be defined as "an event in the natural course of the disease characterized by a change in the patient's baseline dyspnea, cough, and/or sputum that is beyond normal day-to-day variations, is acute in onset and may warrant a change in medication in a patient with underlying COPD". The patient experiencing an exacerbation has one of the following symptoms: increased cough and sputum production, change in the color and/or thickness of the sputum, wheezing, chest tightness, fever. In Crohn's disease or rectocolitis, a flare up is mainly the exacerbation of usual Crohn's disease symptoms: diarrhea, crampy abdominal pain, fever, loss of appetite. In one aspect, the invention provides a method for the treatment an autoimmune or inflammatory disease in a patient comprising: (a) determining whether said patient is experiencing an attack, crisis, exacerbation or flare; (b) if said patient experiences an attack, crisis, exacerbation or flare, administering to said patient an effective dose of anti-TLR3 antibody.

Anti-TLR3 antibodies can also advantageously be used to treat individuals having a relapse. The term "relapse" refers to improvement or stabilization in a patient's symptoms. A disease is relapsing when the health or condition of the patient improves. In one aspect, the invention provides a method for the treatment an autoimmune or inflammatory disease in a patient comprising: (a) determining whether said patient is experiencing a relapse, crisis, exacerbation or flare; (b) if said patient experiences a relapse, administering to said patient an effective dose of anti-TLR3 antibody.

Optionally, an assessment step can be carried out, comprising assessing the expression of a TLR3 polypeptide on cells (e.g. pro-inflammatory cells, dendritic cells, T cells, etc.) from a patient prior to treatment with an anti-TLR3 antibody. Generally, in this step, a sample of cells is taken from a patient, typically as a biopsy, and tested, e.g., using immunoassays, to determine the expression and optionally relative prominence of the TLR3 polypeptide on the cells. In one aspect, a determination that a patient has cells that prominently express the TLR3 polypeptide indicates that the anti-TLR3 antibody (and optionally any further therapeutic agent) is suitable for said patient. In a further step, the patient can then be treated with the anti-TLR3 antibody.

Optionally, in one embodiment, a TLR3 ligand detection step can be carried out, comprising detecting the presence of a TLR3 ligand in a patient, prior to treatment with an anti-TLR3 antibody. Generally, in this step, biological sample is taken from a patient, for example a sample of synovial fluid, e.g. in a patient having rheumatoid arthritis. The biological sample is assessed for the presence of a TLR3 ligand, such as the presence of extracellular dsRNA. If the biological sample is positive for the presence of a TLR3 ligand, the patient can then advantageously be treated with the anti-TLR3 antibody, preferably with an antibody that inhibits TLR3 signaling in a TLR3-expressing cell in the presence of a dsRNA TLR3 ligand.

The anti-TLR3 antibody administered to an individual having a disease can be any monoclonal antibody that specifically binds a TLR3 polypeptide, preferably any antibody inhibits signaling by the TLR3 polypeptide, as described herein. For example, the anti-TLR3 antibody is an antibody that specifically binds TLR3, wherein the antibody has a $K_D$ for binding to a human TLR3 polypeptide of less than $10^{-9}$M under acid conditions, and optionally further also a $K_D$ of less than $10^{-9}$M under neutral conditions.

In one embodiment, the anti-TLR3 antibody is used as monotherapy (the sole therapeutic agent).

According to another embodiment, the treatment methods this invention may further comprise treatment an individual with an anti-TLR3 antibody and a second therapeutic agent, including agents normally utilized for the particular therapeutic purpose for which the antibody is being administered. The anti-TLR3 antibody and second therapeutic agent can be administered separately, together or sequentially, or in a cocktail. The second therapeutic agent will normally be administered in amounts typically used for that agent in a monotherapy for the particular disease or condition being treated. In one embodiment, the second therapeutic agent is administered in a dose less than the generally accepted efficacious dose; for example, in various embodiments, the composition comprises a dosage that is less than about 10% to 75% of the generally accepted efficacious dose is administered. In one embodiment, the second therapeutic agent is a corticosteroid, e.g. a corticosteroid selected from the group consisting of dexamethasone, hydrocortisone (Cortisol), cortisone acetate, prednisone, prednisolone, methylprednisolone, deflazacort, betamethasone, triamcinolone, beclometasone, paramethasone, fluticasone, fludrocortisone acetate, deoxycorticosterone acetate (DOCA), fluprednisolone, fluticasone propionate, budesonide, beclomethasone dipropionate, flunisolide and triamcinolone acetonide. Preferably, the second therapeutic agent is an agent that reduces proteolytic enzymes, an inflammatory mediator, or a proinflammatory cytokine such as TNF-α and/or interleukin-1 (IL-1). Preferably, the second therapeutic agent is DMARD or a DMD, optionally further wherein the second therapeutic agent is methotrexate (Rheumatrex™, Trexall™), hydroxychloroquine (Plaquenil™), sulfasalazine (Azulfidine®), leflunomide (Arava™), a tumor necrosis factor inhibitor (e.g. etanercept (Enbrel®, adalimumab (Humira™), and infliximab (Remicade™)), a T-cell costimulatory blocking agent (e.g. abatacept (Orencia™)), a B cell depleting agent (e.g. rituximab (Rituxan™)), an interleukin-4 (IL-4) antagonist therapy (e.g., anti-IL4 antibodies or anti-IL4 receptor antibodies), an interleukin-5 (IL-5) antagonist therapy (e.g., anti-IL5 antibodies or anti-IL5 receptor antibodies), an interleukin-6 (IL-6) antagonist therapy (e.g., anti-IL6 antibodies or anti-IL6 receptor antibodies), an interleukin-1 (IL-1) receptor antagonist therapy (anakinra (Kineret™)), an anti-BlyS antibody (Benlysta™), intramuscular gold, or another immunomodulatory or cytotoxic agent (e.g. azathioprine (Imuran™), cyclophosphamide, or cyclosporine A (Neoral™, Sandimmune™)). In one embodiment, when treating respiratory disease the second therapeutic agent is a PDE-4 inhibitor.

In some embodiments, the anti-TLR3 antibody is administered prior to the administration of the second therapeutic agent. For example, an anti-TLR3 antibody can be administered approximately 0 to 30 days prior to the administration of the second therapeutic agent. In some embodiments, an anti-TLR3 antibody is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days prior to the administration of the second therapeutic agent. In some embodiments, the anti-TLR3 antibody is administered concurrently with the administration of the therapeutic agents. In some embodiments, the anti-TLR3 antibody is administered after the administration of the second therapeutic agent. For example, an anti-TLR3 antibody can be administered approximately 0 to 30 days after the administration of the second therapeutic agent. In some embodiments, an anti-TLR3 antibody is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days after the administration of the second therapeutic agent.

For use in administration to a patient, the composition will be formulated for administration to the patient. The compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques.

The present antibodies can be included in kits. The kits may optionally further contain any number of antibodies and/or other compounds, e.g., 1, 2, 3, 4, or any other number of therapeutic antibodies and/or compounds (e.g. second therapeutic agent(s)). It will be appreciated that this description of the contents of the kits is not limiting in any way. For example, the kit may contain other types of therapeutic compounds. Preferably, the kits also include instructions for using the antibodies, e.g., detailing the herein-described methods.

Further aspects and advantages of this invention will be disclosed in the following experimental section, which should be regarded as illustrative and not limiting the scope of this application.

EXAMPLES

Materials and Methods
Materials
293T Human Embryonic Kidney cells (#CRL-1573) was purchased from the ATCC. Antibodies (antigen, supplier, reference): AP-coupled F(ab')$_2$ Fragment Goat Anti-Mouse IgG (H+L), Jackson Immunoresearch, ref. 115-056-003, PE-coupled goat anti-mouse IgG Fc, Beckman Coulter, IM0551 Instrumentation: FACSCanto II® flow cytometer (BD Biosciences). TLR3 ligands (name, supplier, reference): poly(IC) HMW, InvivoGen, ref. tlrl-pic. PolyAU, also referred to as IPH3102, is an at least partially double stranded molecule made of polyadenylic acid(s) and polyuridylic acid(s), prepared as described in WO2009/130616 (Innate Pharma), the disclosure of which is incorporated herein by reference. PolyAU was a high molecular weight polyAU having an M$_n$ (also referred to as "number average molecular weight" or "mean molecular weight") above 2000 kD, a PI of 1.4-1.6, and thermal stability: 62.3-63.2° C., hyperchromicity of 53-60%. Antibody 31C3 is described in PCT application No. WO2011/004028, the disclosure of which is incorporated herein by reference.

Surface Plasmon Resonance (SPR)

General Biacore T100 procedures. SPR measurements were performed on a Biacore T100 apparatus (Biacore GE Healthcare) at 25° C. In all Biacore experiments HBS-EP+ or HBS-P buffer (Biacore GE Healthcare) served as running buffer and sensorgrams were analyzed with Biaevaluation 4.1 and Biacore T100 Evaluation software.

For bivalent affinity measurement, unless indicated otherwise, TLR3-His protein was immobilized on a Sensor Chip CM5 (carboxymethylated dextran layer) by amine coupling. Anti-TLR3 antibodies were diluted to a concentration series (0.01 to 100 nM) in the running buffer HBS-EP+ (for affinity at neutral pH) or 10 mM acetate pH5.6, 150 mM NaCl (for affinity at acidic pH), injected over the immobilized antigen for two minutes at a flow rate of 40 µl/min and allowed to dissociate for 3 minutes before regeneration by a 5 to 30s injection of 0.5M NaCl, 10 mM NaOH buffer. The resulting sensorgrams were analysed by global fitting using the appropriate model.

Luciferase Reporter Assay.

A reporter gene assay using as promoter ISRE (IFN-stimulated response element) and as reporter gene and protein luciferase was set up. A 293T cell line (ATCC, #CRL-1573) was stably transfected with pISRE-luc plasmid (#219089—Stratagene), further selected by cloning as inducing optimal response to IFN-alpha stimulation and referred to as control 293T-ISRE. This cell line was further stably transfected with pUNO-humanTLR3 plasmid (#puno-htlr3—InVivogen) and referred to as 293T-TLR3-ISRE.

Efficacy assay was performed as described: on day 0, cells are seeded at 4×105 cells/mL in complete culture medium in 96-well culture plate (100 µl/well). Cells are first incubated at 37° C. for 20 hours, then 50 µL of medium are discarded and cells are activated with 25 µl/well final of fixed amounts of polyAU together with increasing concentrations of anti-TLR3 antibodies. Cells incubated with fresh medium will be used as background luciferase activity (50 µl/well). Cells are incubated at 37° C. for 6 hours. 100 µL of freshly thawed Steady Glo (Promega) are added to each well, plates were incubated 10 min at RT in the dark and the light emitted in each well is quantified as Count Per Second (CPS) on a gamma-counter (TopCount) apparatus.

Generation of Mutant TLR3 Constructs K145E, D116R, K182E, N196A and E171A

The generation of the TLR3 mutants K145E, D116R, K182E, N196A and E171A was performed using the Stratagene's QuikChange® Site-Directed Mutagenesis Kit according to the manufacturer instructions. The oligonucleotides used are listed in Table 4A. Mutagenesis was performed on wild type human TLR3 inserted into a pcDNA3.1 vector. After sequencing, the vectors containing the mutated sequences were prepared as Maxiprep using the Promega PureYield™ Plasmid Maxiprep System. Vectors were then used for HEK-293T cell transfection using Invitrogen's Lipofectamine 2000 according to the manufacturer instructions.

TABLE 4A

| Oligonucleotide name | Sequence |
|---|---|
| K145E forward | 5' GAA AAT TAA AAA TAA TCC CTT TGT CGA GCA GAA GAA TTT AAT CAC ATT AG 3' (SEQ ID NO: 65) |
| K145E reverse | 5' CT AAT GTG ATT AAA TTC TTC TGC TCG ACA AAG GGA TTA TTT TTA ATT TTC 3' (SEQ ID NO: 66) |
| D116R forward | 5' CAA TGA GCT ATC TCA ACT TTC TCG TAA AAC TTT GCT CTG CAC 3' (SEQ ID NO: 67) |
| D116R reverse | 5' GTG CAG AAG CAA AGT TTA CGA GAA AGT TGA GAT AGC TCA TTG 3' (SEQ ID NO: 68) |
| K182E forward | 5' CAA GAG CTT CTA TTA TCA AAC AAT GAG ATT CAA GCG CTA AAA GTG AAA G 3' (SEQ ID NO: 69) |
| K182E reverse | 5' C TTC ACT TTT AGC GCT TGA ATC TCA TTG TTG TAA TAG AAG CTC TTG 3' (SEQ ID NO: 70) |
| N196A forward | 5' GAA GAA CTG GAT ATC TTT GCC GCT TCA TCT TTA AAA AAA TTA GAG TTG 3' (SEQ ID NO: 71) |
| N196A reverse | 5' CAA CTC TAA TTT TTT TAA AGA TGA AGC GGC AAA GAT ATC CAG TTC TTC 3' (SEQ ID NO: 72) |
| E171A forward | 5' GGA ACT CAG GTT CAG CTG GCC AAT CTC CAA GAG CTT CTA TTA TCA 3' (SEQ ID NO: 73) |
| E171A reverse | 5' TGA TAA TAG AAG CTC TTG GAG ATT GGC CAG CTG AAC CTG AGT TCC 3' (SEQ ID NO: 74) |

Generation of N-terminal Mutant TLR3 Constructs 1-19

The generation of the TLR3 mutants (V5-TLR3-CD32 constructs) were generated by PCR (see Table 4B below). All the Mx-R primers were used with the following 5' primer ACCCAAGCTGGCTAGCATGAGACAGACTTTGC-CTTG (SEQ ID NO: 121). All the Mx-F primers were used with the following 3' primer AGCACAGTGGCGGCCGCT-TAGTTATTACTGTTGACATGG (SEQ ID NO: 122). The sequences amplified were run on agarose gel then purified using the Qiagen Gel Extraction kit. The two PCR product generated for each mutant were then ligated into a pcDNA3.1 vector, digested with the restriction enzyme NheI and NotI, with the InFusion system (Clontech) according to the manufacturer's instructions.

After sequencing, the vectors containing the mutated sequences were prepared as Maxiprep using the Promega PureYield™ Plasmid Maxiprep System. Vectors were then used for HEK-293T cell transfection using Invitrogen's Lipofectamine 2000 according to the manufacturer instructions.

TABLE 4B

| Mutants | Reverse primers | Forward primers |
|---|---|---|
| Number 1<br>Q44H + V45I | M1-R<br>5'-gggtatatgagtcaacttcagg tggctg-3' (SEQ ID NO: 75) | M1-F<br>5'-ttgactcatataccgatgatc taccc-3' (SEQ ID NO: 76) |
| Number 2<br>R64Q + R65Q | M2-R<br>5'-taattgttggagttgattatgg gtaagg-3' (SEQ ID NO: 77) | M2-F<br>5'-caactccaacaattaccagccg ccaacttc-3'<br>(SEQ ID NO: 78) |
| Number 3<br>T86S + K89Q | M3-R.2<br>5'-ctccagttgtgagat ggagtt aaatcctacatccaagc-3'<br>(SEQ ID NO: 79) | M3-F.2<br>5'-atctcacaactggagccagaat tgtgccagaaactt c-3'<br>(SEQ ID NO: 80) |
| Number 4<br>K97I + M100L | M4-R<br>5'-taacaagggaagtatctggcac aattctggctcc-3'<br>(SEQ ID NO 81) | M4-F<br>5'-atacttcccttgttaaaagttt tgaacctcc-3'<br>(SEQ ID NO 82) |
| Number 5<br>K117Q +<br>A120V | M5-R<br>5'-gaagacaaaggtttgatcagaa agttgagatagctc-3'<br>(SEQ ID NO: 83) | M5-F<br>5'-caaacctttgtcttctgcacga atttgact-3'<br>(SEQ ID NO: 84) |
| Number 6<br>Q136H | M6-R<br>5'-gtggattgagttggacatgaga tgg-3' (SEQ ID NO: 85) | M6-F<br>5'-tccaactcaatccacaaaatta aaataatccc-3'<br>(SEQ ID NO: 86) |
| Number 7<br>N140S | M7-R<br>5'-attagatttaattttctggatt gagttgg-3'<br>(SEQ ID NO: 87) | M7-F<br>5'-aaaattaaatctaatccctttg tcaagcag-3'<br>(SEQ ID NO: 88) |

TABLE 4B-continued

| Mutants | Reverse primers | Forward primers |
|---|---|---|
| Number 8<br>V144K +<br>K145N | M8-R<br>5'-ctgattcttaaagggattattt<br>ttaattttc-3'<br>(SEQ ID NO: 89) | M8-F<br>5'-ccctttaagaatcagaagaatt<br>taatcacattag-3'<br>(SEQ ID NO: 90) |
| Number 9<br>K147-A147 | M9-R<br>5'-tgtgattaaaattcgcctgcttg<br>acaaagggatt-3'<br>(SEQ ID NO: 91) | M9-F<br>5'-gcgaatttaatcacattagatc<br>tg -3' (SEQ ID NO: 92) |
| Number 10<br>K163-A163 | M10-R<br>5'-agttcctaatgctgtagatgac<br>aagcc-3' (SEQ ID NO: 93) | M10-F<br>5'-acagcattaggaactcaggttc<br>ag-3' (SEQ ID NO: 94) |
| Number 11<br>Q167G | M11-R<br>5'-ttccagctgaaccccagttcct<br>aattttgtag-3'<br>(SEQ ID NO: 95) | M11-F<br>5'-ggggttcagctggaaaatctc<br>c-3' (SEQ ID NO: 96) |
| Number 12<br>Q184L +<br>K187R | M12-R<br>5'-acttcgtagcgctagaatttta<br>ttgtttgataatag-3'<br>(SEQ ID NO: 97) | M12-F<br>5'-ctagcgctacgaagtgaagaac<br>tggatatc-3'<br>(SEQ ID NO: 98) |
| Number 13<br>Q184L +<br>K187Q | M13-R<br>5'-actttgtagcgctagaatttta<br>ttgtttgataatag-3'<br>(SEQ ID NO: 99) | M13-F<br>5'-ctagcgctacaaagtgaagaac<br>tggatatc-3'<br>(SEQ ID NO: 100) |
| Number 14<br>D192E +<br>A195G | M14-R<br>5'-attgccaaagatctccagttct<br>tcacttttttagcg-3'<br>(SEQ ID NO: 101) | M14-F<br>5'-gagatctttggcaattcatctt<br>taaaaaaa-3'<br>(SEQ ID NO: 102) |
| Number 15<br>Q208P +<br>I209L | M15-R<br>5'-ctctttaagtggattcgatgac<br>aactct-3'<br>(SEQ ID NO: 103) | M15-F<br>5'-aatccacttaaagagttttctc<br>cag-3' (SEQ ID NO: 104) |
| Number 16<br>H218Q | M16-R<br>5'-tcttccaattgcctgaaaacac<br>cctggagaaaactc-3'<br>(SEQ ID NO: 105) | M16-F<br>5'-caggcaattggaagattatttg<br>g-3' (SEQ ID NO: 106) |
| Number 17<br>A219T | M17-R<br>5'-tcttccaattgtgtgaaaacac<br>cctggagaaaactc-3'<br>(SEQ ID NO: 107) | M17-F<br>5'-cacacaattggaagattatttg<br>g-3' (SEQ ID NO: 108) |
| Number 18<br>G234N +<br>S236H | M18-R<br>5'-aaggtggggattcagctggaca<br>ttgttcag-3'<br>(SEQ ID NO: 109) | M18-F<br>5'-ctgaatccccaccttacagaga<br>agctatgtttg-3'<br>(SEQ ID NO: 110) |
| Number 19<br>L243W +<br>A246S | M19-R<br>5'-gtttgataattcccaacatagc<br>ttctctgtaagg-3'<br>(SEQ ID NO: 111) | M19-F<br>5'-tgggaattatcaaacacaagca<br>ttcggaatctg-3'<br>(SEQ ID NO: 112) |
| Number 23<br>S112A +<br>Q113S + S115A | M23-R:<br>5'-tagctcattgtgctggaggtt<br>c-3' (SEQ ID NO: 119) | M23-F:<br>5'-aaaacctttgccttctgca<br>c-3' (SEQ ID NO: 120) |
| Number 24<br>K137S +<br>K139A | M24a-R:<br>5'-tgcaattgactggattgagttg<br>gacatgagatggag-3'<br>(SEQ ID NO: 113) | M24a-F:<br>5'-atccagtcaattgcaaataatc<br>cctttgtcaagcag-3'<br>(SEQ ID NO: 114) |

Generation of TLR3 Cell Surface Constructs

The mature wild-type or mutant TLR3 sequence was fused to the CD32 transmembrane and intracellular domains as described by De Bouteiller et al. (2005) *J. Biol. Chem.* 280(46): 38133-38145. A first round of PCR was performed to introduce a V5 tag in N-terminal position of the TLR3-CD32 fusion protein and a second round—using the first PCR as a template—to introduce the TLR3 leader peptide in the construct. Primers used for these steps were summarized in the table below (Table 5). The PCR product was TA-cloned into the pGEMTeasy vector for sequencing and finally cloned into the pcDNA3.1 vector using the NheI and NotI restriction sites.

TABLE 5

| Oligonucleotide Name | Sequence |
|---|---|
| V5 Tag Forward | 5' AA GGT AAG CCT ATC CCT AAC CCT CTC CTC GGT CTC GAT TCT ACG AAG TGC ACT GTT AGC CAT GAA G (SEQ ID NO: 115) |
| V5 Tag Reverse | 3' AA GCG GCC GC TTA GTT ATT ACT GTT GAC ATG GTC G (SEQ ID NO: 116) |
| TLR3 leader peptide Forward | 5' AA GCT AGC ATG AGA CAG ACT TTG CCT TGT ATC TAC TTT TGG GGG GGC CTT TTG CCC TTT GGG ATG CTG TGT GCA TCC TCC ACC ACC GGT AAG CCT ATC CCT AAC CC (SEQ ID NO: 117) |
| TLR3 leader peptide Reverse | 3' AA GCG GCC GC TTA GTT ATT ACT GTT GAC ATG GTC G (SEQ ID NO: 118) |

Titration on Cells Expressing TLR3+ at their Surface

HEK293T cell line was transiently transfected with the wild-type or mutant TLR3 ECD-CD32 construct using lipofectamine 2000 and stained for 30 min at 4° C. with a dose-range of 11E1 or 31C3 Bound mAbs were revealed by addition of a PE-coupled goat anti-mouse IgG Fc antibody for 20 additional min at 4° C. Following two wash cycles, cell MFI was analyzed on a FACS Canto II cytometer. With the aim to study the effect of pH on mAb affinity, staining was performed in staining buffer (0.2% BSA, 2 mM EDTA, 0.02% Sodium Azoture) pH7.4 or in citric acid-acidified staining buffer pH5.6.

Example 1

Generation of TLR3-Specific Monoclonal Mouse and Rat Anti-Human Antibodies

A series of immunization were carried out in order to generate different antibodies that block human TLR3 with improved efficacy over previous antibodies. The primary and secondary screens were as follows.

Immunization #1.

Primary screen. To obtain anti-human TLR3 antibodies, Balb/c mice (3 animals) were immunized with a recombinant human His-tagged TLR3 extracellular domain recombinant protein (R&D systems, #1487-TR-050). Mice were immunized, spleen cells were fused and cultured in the presence of irradiated spleen cells. Mice received one primo-immunisation with an emulsion of 50 µg TLR3 protein and Complete Freund Adjuvant, intraperitoneally, a $2^{nd}$ immunization with an emulsion of 50 µg TLR3 protein and Incomplete Freund Adjuvant, intraperitoneally, and a boost with 10 µg TLR3 protein, intravenously. Hybridomas were plated into culture plates and supernatants (SN) were evaluated in a first screen for TLR3 binding using an ELISA developed for detection of binding to TLR3. Briefly, His-tagged recombinant TLR3 protein (R&D systems, #1487-TR) was coated on Maxisorp® ELISA plates (Nunc). Supernatant from hybridoma culture plates were harvested and incubated onto ELISA plates in the presence of an anti-TLR3 antibody that inhibits TLR3 and binds within the C-terminal portion, and the presence of TLR3 binding Ig was revealed with AP-coupled F(ab')₂ fragment Goat Anti-Mouse IgG (H+L). 358 hybridomas out of 3840 were selected for the secondary screen.

Secondary screen; selection of hybridomas of interest. 358 supernatants were retained and tested in a further screen by FACS staining using a D116R-mutated TLR3 transiently expressing 293T cell line to identify antibodies that do not lose binding to the mutant TLR3 at amino acid position 116. 151 hybridomas on the 358 did not lose binding to D116R. Antagonist activity of hybridomas was also tested in a ISRE-luciferase gene reporter assay on 293T-huTLR3 cells. Wells from supernatants having an inhibitory effect superior to 60% were selected for further cloning. 28 hybridomas had antagonist activity and 25 clones had both antagonist activity and D116R binding.

Cloning of hybridomas of potential interest. Potentially interesting hybridomas from the initial screening were cloned by limiting dilution techniques in 96-wells plates, and clones were tested in the same series of secondary screens as for hybridomas. Clones from 13 hybridomas had both antagonist activity and D116R binding.

With the aim to compare these 13 hybridomas to our reference anti-TLR3 mAbs (notably 31C3), the 13 hybridomas were amplified and their supernatants were purified. Purified mAbs were tested in a gene-reporter assay. Hybridomas were selected for further characterization based on efficiency of blockade of TLR3 signaling in comparison with reference anti-TLR3 mAbs.

2 hybridomas were further assessed for epitope binding to mutant TLR3 K145E and K182E (see also Example 6). Both antibodies did not show any loss of binding to the K145E variant of TLR3 but one of them showed loss in binding to the mutant K182E. Clone 11E1 bound TLR3 even in presence of the mutation K145E or K182E.

Immunization #2.

LOU/c rats were immunized with recombinant His-tagged human TLR3, carrier free extracellular domain recombinant protein (R&D systems, #1487-TR). Rats received, on day 0, one primo-immunisation with an emulsion of 50 µg of human TLR3 diluted in PBS and Complete Freund Adjuvant, intraperitoneally, a $2^{nd}$ immunization on day 14 with an emulsion of 50 µg of human TLR3 diluted in PBS and Incomplete Freund Adjuvant, intraperitoneally, and one boost with 25 µg of human TLR3 diluted in PBS, intravenously. Immune spleen cells were fused with X63.Ag8.653 immortalized B cells, and cultured in the presence of irradiated spleen cells.

Secondary screening was performed as in immunization #1, above. Potentially interesting hybridomas were cloned by limiting dilution techniques in 96-wells plates, and clones were tested in the same series of secondary screens as for hybridomas. With the aim to compare hybridomas to our reference anti-TLR3 mAbs, the hybridomas were amplified and their supernatants were purified. Purified mAbs were tested in a gene-reporter assay. Hybridomas were selected for further characterization based on efficiency of blockade of TLR3 signaling in comparison with reference anti-TLR3 mAbs 31C3. Hybridomas were further assessed for epitope binding to mutant TLR3 polypeptides having K145E and K182E. Clones 7G11, 31F6, 32C4 and 37B7 bound TLR3 even in presence of the mutation K145E or K182E.

Example 2

Generation of TLR3-Specific Monoclonal Rat Anti-Mouse Antibodies

Primary screen. To obtain anti-TLR3 antibodies, LOU/c rats were immunized with a recombinant His-tagged mouse TLR3, carrier free extracellular domain recombinant protein (R&D systems, #3005-TR) and recombinant His-tagged human TLR3, carrier free extracellular domain recombinant protein (R&D systems, #1487-TR). Rats received, on day 0, one primo-immunisation with an emulsion of 50 µg of mouse TLR3+50 µg of human TLR3 diluted in PBS and Complete Freund Adjuvant, intraperitoneally, a $2^{nd}$ immunization on day 14 with an emulsion of 50 µg of mouse TLR3+50 µg of human TLR3 diluted in PBS and Incomplete Freund Adjuvant, intraperitoneally, and one boost with 25 µg of mouse TLR3+25 µg of human TLR3 diluted in PBS, intravenously. Immune spleen cells were fused with X63.Ag8.653 immortalized B cells, and cultured in the presence of irradiated spleen cells.

40 culture plates were obtained and evaluated in a first screen for mouse TLR3 binding using an ELISA developed for detection of binding to TLR3. Briefly, His-tagged recombinant mouse TLR3 protein (R&D systems, #1487-TR-050) was coated on Ni-NTA 96-wells plates (Qiagen). Supernatant (SN) from hybridoma culture plates and incubated in TLR3-plates, and the presence of TLR3 binding Ig was revealed with goat anti-mouse F(ab) IgG-HRP.

Secondary screen: selection of hybridomas of interest. 181 supernatants were retained and tested in a further screen in an inhibition test on 293T-mTLR3 cells. Wells from supernatants having an inhibitory effect superior to 95% were selected for further cloning by limiting dilution.

Cloning of hybridomas of potential interest. 27 potentially interesting hybridomas selected from the initial screening were cloned by limiting dilution techniques in 96-wells plates, and 370 subclones were evaluated in a screen for mouse TLR3 binding using an ELISA as above. The 178 positive clones were tested in a further screen in an inhibition test on 293T-TLR3 cells as above. Among them was supernatant from well G7 from plate 28 (28G7).

Example 3

Binding to Cell Surface TLR3

To investigate the possibility that TLR3 is cycled to the cell surface and that cell surface TLR3 contributes to internalization and efficacy of inhibitory anti-TLR3 antibodies, binding to cell surface TLR3 was tested, in comparison to reference antibody 31C3. Additionally, binding (e.g. affinity) to cell surface TLR3 at neutral pH may differ from that of endosomally-expressed TLR3 at acidic pH. Antibodies were tested for binding to cells expressing human TLR3 solely at the cell surface (TLR3/CD32-expressing 293T cells), at neutral pH conditions since pH could potentially affect TLR3 conformation. Results for neutral pH are shown in FIGS. 1A, 1B, 1C and 1D for antibodies 11E1, 7G11, 32C4 and 31F6, respectively. EC50 values are shown in Table 6. Antibodies 11E1, 7G11, 31F6 and 32C4 each had strong binding to surface-expressed human TLR3 at neutral pH. Affinity of the antibodies for TLR3 was stronger than reference antibody 31C3 at neutral pH.

TABLE 6

| mAb | EC50 (µg/ml) |
|---|---|
| 31C3 | 0.413 |
| 11E1 | 0.016 |
| 7G11 | 0.021 |
| 32C4 | 0.037 |
| 31F6 | 0.026 |

Example 4

Bivalent Affinity at Endosomal and Neutral pH

Binding properties of the antibody 11E1 was determined using the methods described for SPR, item c). Binding to TLR3 at neutral (pH 7.2) and acid (pH 5.6) conditions, and $K_D$ values were calculated. At neutral pH, 11E1 showed strong bivalent affinity ($K_D$) for recombinant human TLR3 (mean $K_D$ (M) at pH 7.2 of $8.75*10^{-11}$). Binding affinity at pH 5.6 was somewhat lower for antibody 11E1 than affinity at pH 7.2, as the mean $K_D$ (M) at pH 5.6 was $1*10^{-9}$).

Similarly, binding of anti-mouse TLR3 antibodies to mouse TLR3 was determined at neutral (pH 7.2) and acid (pH 5.6) conditions, and $K_D$ values were calculated. At neutral and acid pH, mAb 32D4, 28G7 and 13D1 all showed strong and similar bivalent affinity ($K_D$) for recombinant mouse TLR3 better than 500 picomolar. The affinity (mean of 2 or 3 experiments) of mAb 28G7 was $7.05*10^{-13}$ at neutral pH (mean $K_D$ (M) at pH 7.2) and $1.26*10^{-13}$ at acid pH (mean $K_D$ (M) at pH 5.6).

Example 5

Human Reporter Assay

Antibodies were tested for inhibition of TLR3 signaling in a luciferase based reporter gene activity (293T-TLR3-ISRE). Engagement of TLR3 receptor using TLR3-agonists such as poly (I:C) has been reported to activate the type-IFN pathway including the promoter ISRE (Wietek et al. J. Biol. Chem., 278 (51), p50923, 2003). Briefly, dsRNA TLR3 agonists were used to induce TLR3 signaling in the reporter assay in the presence of anti-TLR3 antibodies, and TLR3 signaling was assessed. Antibodies 11E1, 7G11, 31F6, 32C4 and 37B7 were all more potent in this assay than antibody 31C3. The results shown in FIGS. 2A, 2B, 2C, 2D and 2E for antibodies 11E1, 7G11, 32C4, 31F6 and 37B7, respectively, showing dose dependent inhibition of TLR3 signaling using a 293T-human TLR3 luciferase assay with the human anti-TLR3 antibodies. Each antibody is compared with reference antibody 31C3.

Similarly, rat anti-mouse TLR3 antibodies were assessed similarly in separate experiments for their ability to inhibit TLR3 signaling in a murine TLR3 luciferase based reporter gene activity (293T-mTLR3-ISRE). Antibody 28G7 showed dose-dependent inhibition of TLR3 signaling with an IC50 of 2.6 µg/ml.

Example 6

Epitope Mapping

Epitope mapping at neutral pH. Competition assays were conducted by FACS assay on HEK293T-WT TLR3 ECD/CD32 cells. Antibodies 11E1, 7G11, 31F6, 32C4 and 37B7 competed with previously obtained antibody 31C3 for binding to TLR3 since binding by one antibody impaired the binding to TLR3 of the other antibody. Antibody 31C3 binds at least in part to a region of TLR3 corresponding to residues 102 to 204 of the mature TLR3 polypeptide (particularly residues 174 to 191 and residue 182) and compete with each other for binding to human TLR3. Antibodies 11E1, 7G11, 31F6, 32C4 and 37B7 each competed with 31C3, but the degree of competition varied, suggesting that epitopes of 11E1, 7G11, 31F6, 32C4 and 37B7 were in the same region but having differences between each other. Antibody 11E1 competed with each of antibodies 7G11, 31F6, 32C4 and 37B7. Based on the profiles of competition between antibodies 11E1, 7G11, 31F6, 32C4 and 37B7 and antibody 31C3, at least three different epitope bins were determined since at least 11E1, 37B7 seemed to differ from each other and from 7G11, 31F6, 32C4.

Example 7

Epitope Mapping by Binding to TLR3 Mutants

Antibodies 11E1, 7G11, 31F6, 32C4 and 37B7 compete for binding to TLR3 with antibody 31C3. 31C3 has been determined to bind within the N-terminal end of human TLR3, having a principal epitope of the antibody that includes residue 182 but not residues K145, D116, K182, E171 or N196. Antibodies 11E1, 7G11, 31F6, 32C4 and 37B7 were therefore tested for binding to TLR3 mutants. TLR3 mutant polypeptides having mutations K145E, D116R, K182E, N196A and E171A (reference to SEQ ID NO: 1) were prepared as described herein in the Materials and Methods and anti-TLR3 antibody staining to cells expressing TLR3 mutant polypeptides was assessed by FACS. Antibodies 11E1, 7G11, 31F6, 32C4 and 37B7 did not show any loss of binding to unmutated wild type (WT) TLR3 nor to any of K145E, D116R, E171A, K182E or N196A. The principal epitope of antibodies 11E1, 7G11, 31F6, 32C4 and 37B7 while located in the N-terminal region therefore not include residues K145, D116, K182, E171 or N196.

Antibodies were then tested for binding to further set of mutants in the N-terminal portion of TLR3 to identify new epitopes. Antibodies were therefore tested for binding to TLR3 mutants. TLR3 mutant polypeptides having mutations in positions Q44H and V45I, R64Q and R65Q, T86S and K89Q, K97I and M100L, K117Q and A120V, Q136H, N140S, V144K and K145N, K147A, K163A, Q167G, Q184L and K187R, Q184L and K187Q, D192E and A195G, Q208P and I209L, H218Q, A219T, G234N and S236H, L243W and A246S, S112A. Q113S. and S115A, and K137S and K139A (reference to SEQ ID NO: 1) were prepared as described herein in the Materials and Methods and anti-TLR3 antibody staining to cells expressing TLR3 mutant polypeptides was assessed by FACS. Antibody 11E1 showed loss of binding to mutants having the substitutions R64Q and R65Q, and to lesser degree possibly adjacent mutants T86S and K89Q. Antibodies 7G11, 31F6, 32C4 and 37B7 showed loss of binding to mutants having the substitutions K117Q and A120V but not any of the other mutants. Antibodies 11E1 and 37B7 showed complete loss of binding to mutants having the substitutions K137S and K139A, while antibodies 7G11, 31F6 and 32C4 showed partial loss of binding to mutants having the substitutions K137S and K139A. Furthermore, all of the 7G11, 31F6, 32C4 and 37B7 antibodies showed complete loss of binding to mutants having the substitutions S112, Q113 and S115. Antibodies 11E1 and 31C3 did not show loss of binding to mutants having the substitutions S112, Q113, and S115. The principal epitope of antibody 11E1 therefore includes residues R64 and R65 and possibly (to lesser degree) adjacent residues T86 and K89, as well as residues K137 and K139. The principal epitope of antibodies 7G11, 31F6, 32C4 and 37B7 therefore includes residues K117 and/or A120, as well as S112, Q113 and/or S115. Additionally, for antibody 37B7 the principal epitope further includes residues K137 and K139 while for antibodies 7G11, 31F6 and 32C4 the residues K137 and K139 may also be within the epitope. Residues R64Q and R65Q in particular are within the N-terminal dsRNA binding region on the glycan-free lateral surface of TLR3 and residues K117 and A120 although partly on the backbone of the TLR3 molecule, are adjacent to the N-terminal dsRNA binding region. Surface-exposed residues adjacent to these mutated residues may also contribute to the epitopes of the antibodies, including for example residues 41, 43, 60, 61, 62, 64, 65, 67, 68, 88, 91, 92, 93, 96, 97, 108, 110, 112, 113, 114, 115, 121, 132, 134, 137 and/or 139 (reference to SEQ ID NO: 1) located at the surface of TLR3 in the region of the N-terminal dsRNA binding region. Antibodies may as such compete with binding of dsRNA to TLR3. The antibodies may bind within and/or adjacent to the N-terminal dsRNA binding site, including optionally further spanning residues on the backbone of the TLR3 protein.

Figure 2A:
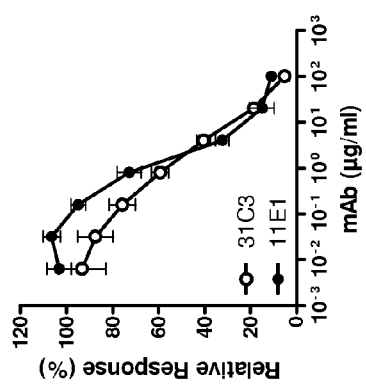
FIGS. 2A, 2B, 2C, 2D and 2E show dose dependent inhibition of TLR3 signaling using a 293T-human TLR3 luciferase assay with the human anti-TLR3 antibodies. Each antibody is compared with reference antibody 31C3; inhibition of dsRNA-induced TLR3 signaling is improved for antibodies 11E1, 7G11, 32C4, 31F6 and 37B7.
Figure 2B:
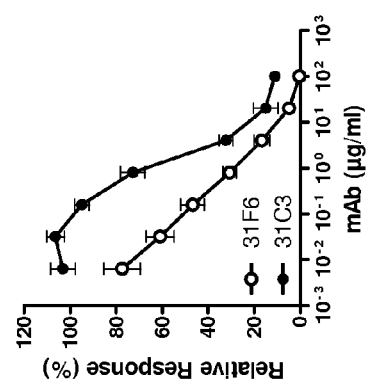
Figure 2C:
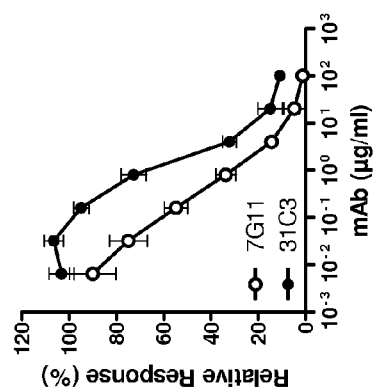
Figure 2D:
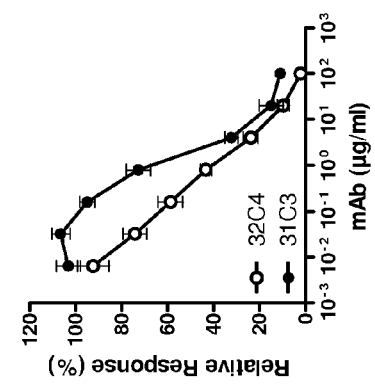
Figure 2E:
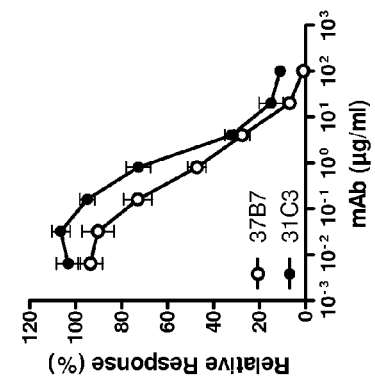
Figure 2F:
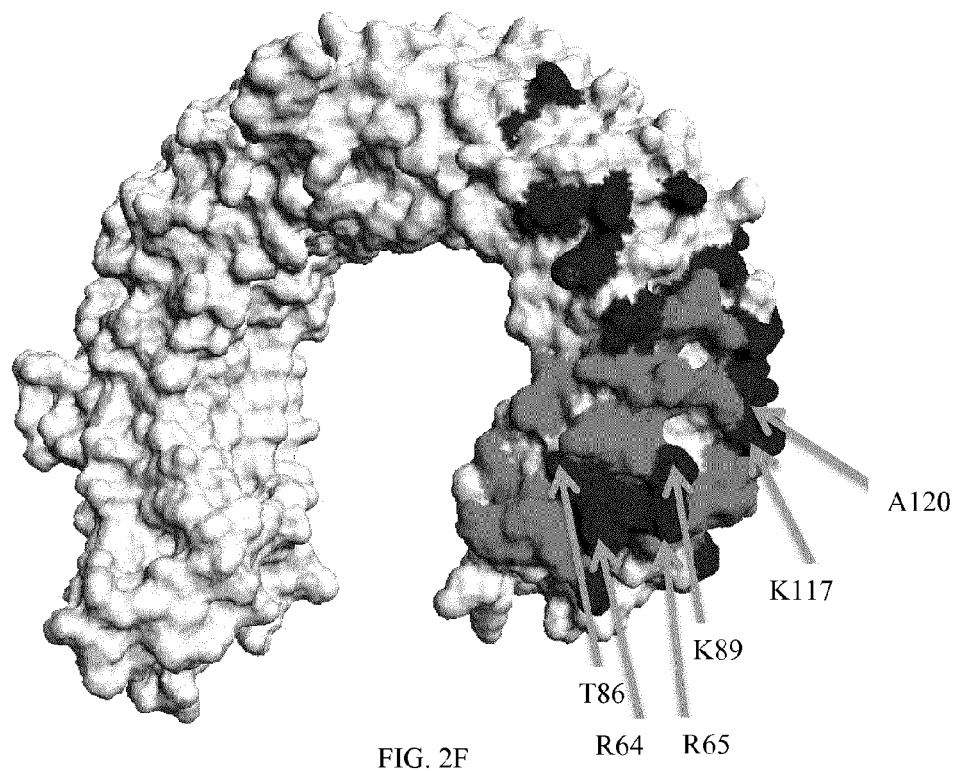
FIGS. 2F, 2G, and 2H show view of the N-terminal end of the TLR3 polypeptide, showing amino acid residues mutated indicated in black and residues adjacent to residues which form part of the principle epitopes in grey.
Figure 2G:
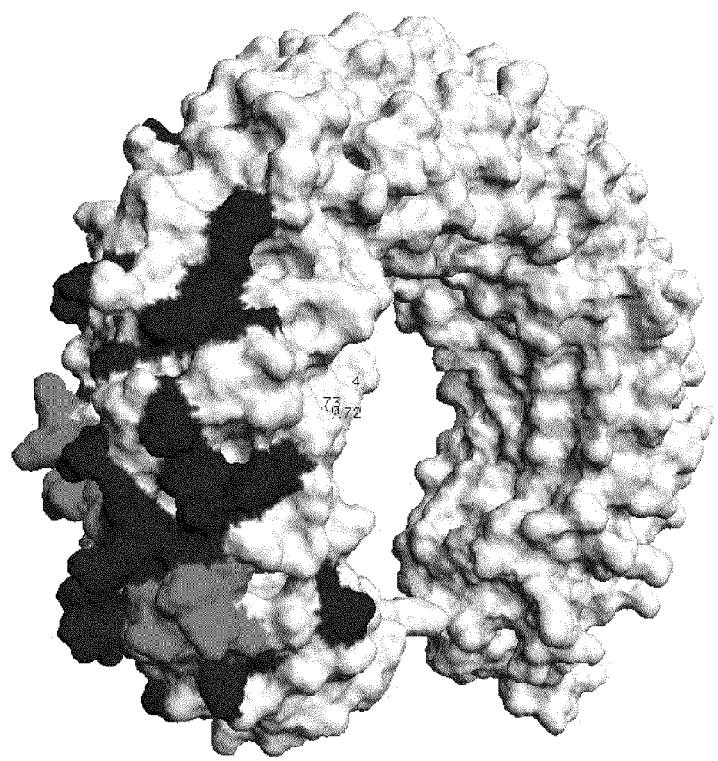
Figure 2H:
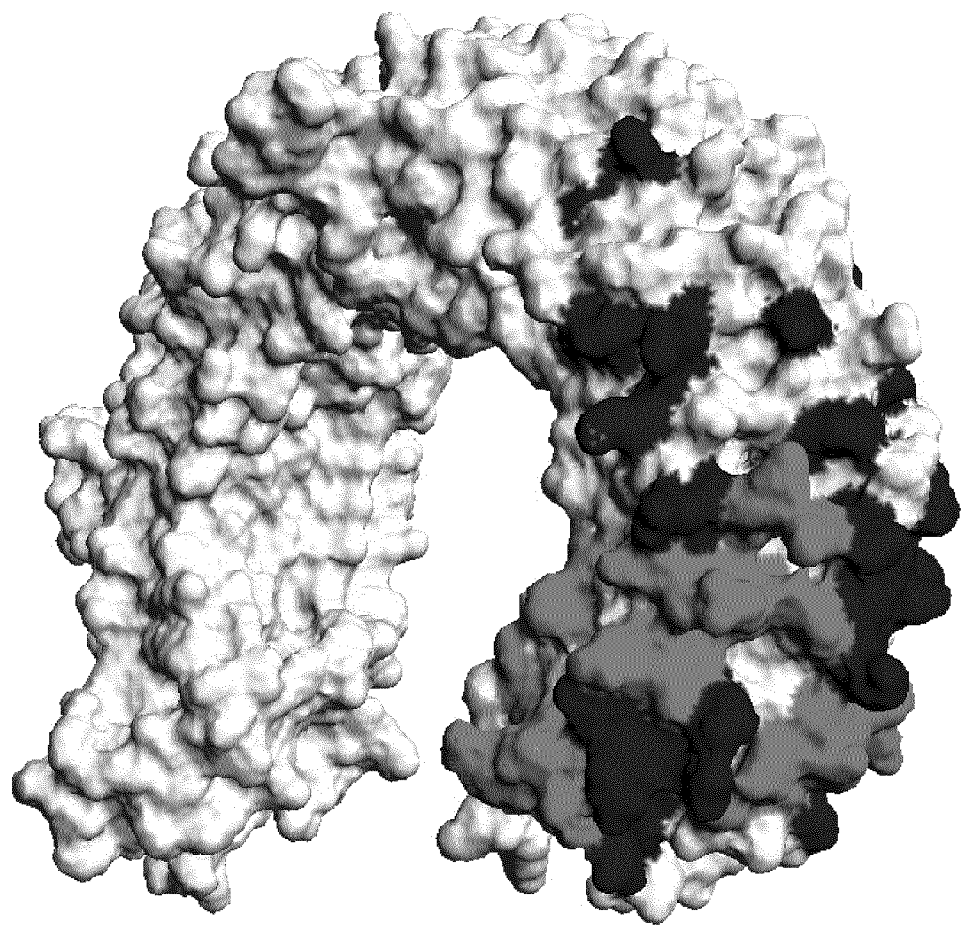

FIGS. 2F, 2G, and 2H show view of the N-terminal end of the TLR3 polypeptide, showing amino acid residues mutated indicated in black (Q44, V45, R64, R65, T86, K89, K97, M100, K117, A120, Q136, N140, V144, K145, K147, K163, Q167, Q184, K187, Q184, K187, D192, A195, Q208, I209, H218, A219, G234 and S236, L243 and A246). Also shown in grey are residues adjacent to residues 86, 89, 117 and 120 (residues 41, 43, 60, 61, 62, 67, 68, 88, 91, 92, 93, 96, 108, 110, 112, 113, 114, 115, 121, 132, 134, 137 and 139); such adjacent residues may also be bound by antibodies indicated. FIG. 2F shows a view of the glycan-free lateral surface of the TLR3 polypeptide; FIG. 2G shows a view of the glycan-containing lateral surface of the TLR3 polypeptide and the backbone, with the N-terminal end of the TLR3 polypeptide in the foreground (at the left of the image). FIG. 2H shows a view of the glycan-free lateral surface of the TLR3 polypeptide and the backbone, with the N-terminal end of the TLR3 polypeptide in the foreground (at the right of the image).

Example 8

In Vivo Efficacy Model for the Treatment of RA—Preventive Setting

Briefly 20 mice were immunized on day 0 with 100 µg of collagen emulsified in CFA complemented with Mycocbater tuberculosis (2 mg/ml) and injected intradermally (ID) at the base of the tail. At day 17, animals were scored (clinical signs often appear prior to the boost), randomized into 2 groups of 8 or 9 mice according to the sum of the 4 limbs clinical score and treated. At days 21, the collagen immunization was boosted by ID administration of collagen alone (100 µg in 50 µl).

The following groups were constituted:
group 1 (PBS, n=9): treated 200 µl twice/week IP
group 2 (28G7, n=8): treated 500 µg/mice twice/week IP
Scoring of the four limbs of the animal was evaluated thrice a week for 3 to 4 weeks. Scoring was evaluated according to Table 7.

TABLE 7

| Score | Inflammation level |
|---|---|
| 0 | No evidence of erythema and swelling |
| 1 | Erythema and mild swelling confined to the tarsals or ankle joint |
| 2 | Erythema and mild swelling extending from the ankle to the tarsals |
| 3 | Erythema and moderate swelling extending from the ankle to metatarsal joints |
| 4 | Erythema and severe swelling encompass the ankle, foot and digits, or ankylosis of the limb |

Figure 3A:
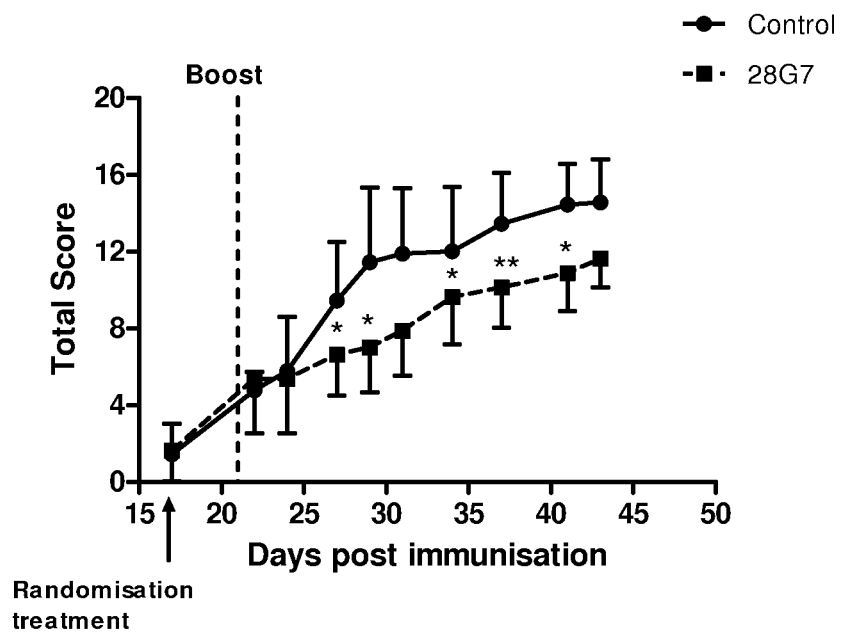
FIG. 3A shows the results of a preventive rheumatoid arthritis mouse model.

The results are reported in FIG. 3A. The present experiment underlines that the anti-TLR3 antibodies are statistically effective (*p>0.05, **p>0.005, in Dunnett's test) in the curative treatment of Rheumatoid Arthritis (RA) in comparison with PBS.

Example 9

In Vivo Efficacy Model for the Treatment of RA—Curative Setting

Experiment #1: 28G7, PBS, MTX

Briefly 30 mice were immunized on day 0 with intradermal injection of 100 µg of collagen emulsified in CFA complemented with Mycobater tuberculosis (2 mg/ml) at the base of the tail. 21 days later, the collagen immunization is boosted by ID administration of collagen alone (100 µg in 50 µl/mice). At day 24, animals were randomized into 3 groups of 10 mice according to the sum of the 4 limbs clinical score and treatment began.

Group 1 (PBS, n=10): treated 200 µl twice/week IP.
Group 2 (Methotrexate—MTX, n=10): treated 2.5 mg/kg twice/week IP.
Group 3 (28G7, n=10): treated 500 µg/mice twice/week IP.

Scoring of the four limbs of the animal was evaluated thrice a week for 3 to 4 weeks. Scoring was evaluated according to Table 7.

Figure 3B:
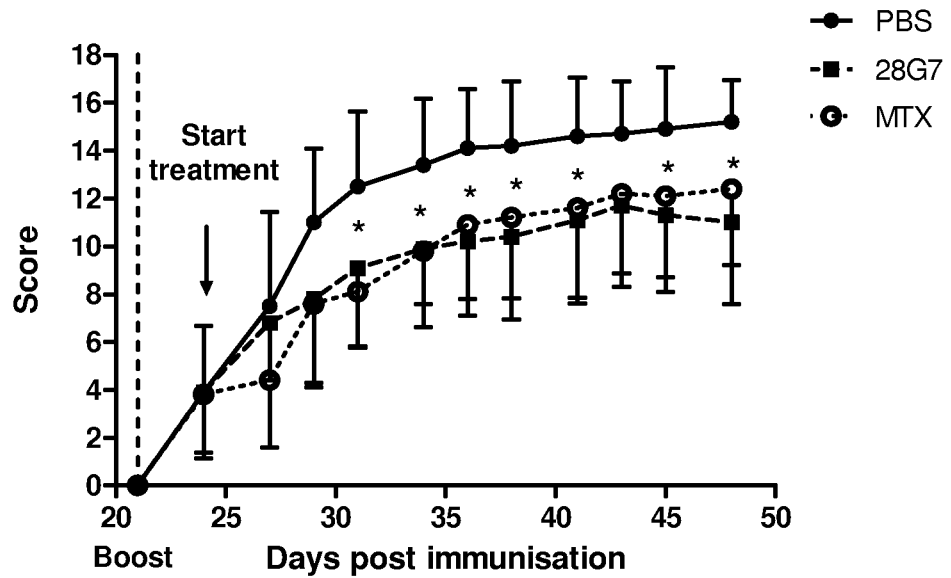
FIG. 3B shows the results of a curative rheumatoid arthritis mouse model.

The results are reported in FIG. 3B. The present experiment underlines that the anti-TLR3 antibodies are statistically effective in the treatment of an established Rheumatoid Arthritis (RA) in comparison with PBS and Methotrexate (*p>0.05, in Dunnett's test). MTS having a different mechanism of action than the anti-TLR3 antibody, a combination of the two drugs could be beneficial.

Experiment #2: 28G7, PBS, anti-TNFα Humira™

Briefly 35 mice were immunized on day 0 with intradermal injection of 100 µg of collagen emulsified in CFA complemented with Mycobater tuberculosis (2 mg/ml) at the base of the tail. 21 days later, the collagen immunization is boosted by ID administration of collagen alone (100 µg in 50 µl/mice). At day 24, animals were randomized into 4 groups according to the sum of the 4 limbs clinical score and treatment began.

Group 1 (PBS, n=9): treated 200 µl twice/week IP.
Group 2 (control Ig antibody, n=9): treated 500 µl twice/week IP.
Group 3 (28G7, n=9): treated 500 µg/mice twice/week IP.
Group 4 (Humira™, n=6): treated 100 µl twice/week IP.

Scoring of the four limbs of the animal was evaluated thrice a week for 3 to 4 weeks. Scoring was evaluated according to Table 7.

Figure 3C:
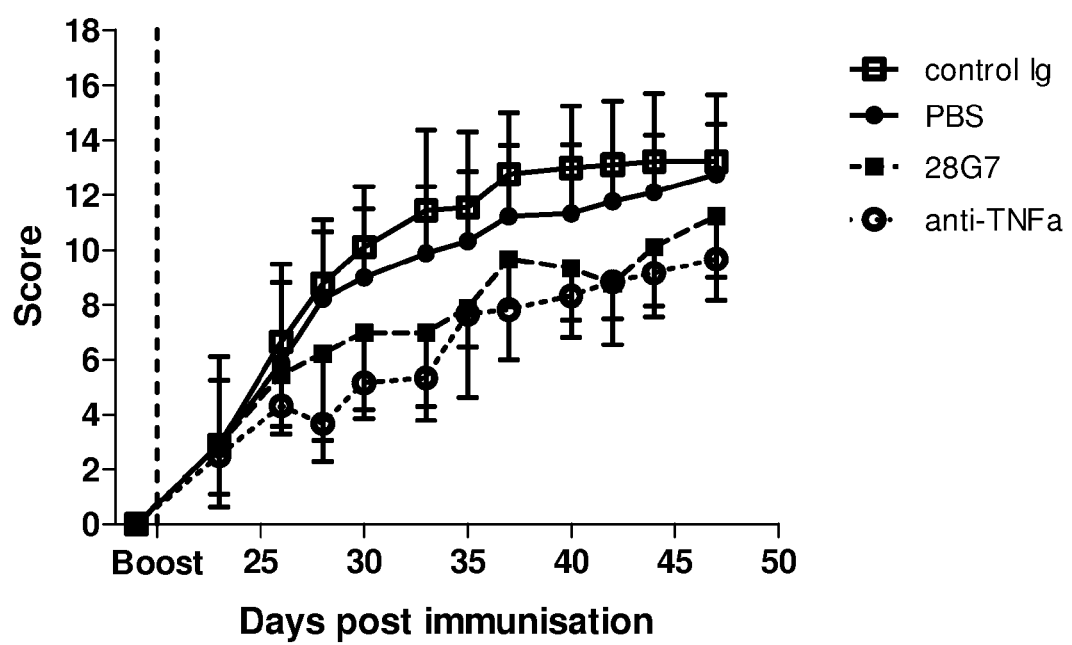
FIG. 3C shows the results of a curative rheumatoid arthritis mouse model when mice are treated with PBS, a control antibody, 28G7 and an anti-TNFα antibody (Humira™).

The results are reported in FIG. 3C. The present experiment underlines that the anti-TLR3 antibodies are effective in the treatment of an established Rheumatoid Arthritis (RA) in comparison with PBS and anti-TNFα antibody Humira™. The anti-TNFα having a different mechanism of action than the anti-TLR3 antibody, a combination of the two drugs could be beneficial.

Example 10

In Vivo Efficacy Model for the Treatment of Colitis

Four groups of 10 male mice (Balb/c) were used for the model of TNBS-induced colitis and one extra group of 8 mice without colitis were used as control (no dosage, intracolonic instillation of saline).

The treated groups were divided as follows:
Group 1: 10 mice received antibody 28G7 (ip, 500 µg/mouse).
Group 2: 10 mice received a non TLR3-relevant antibody administration (ip, 500 µg/mouse).
Group 3: 10 mice received the rat anti-mouse TNF antibody (ip, 15 mg/kg, Humira™)
Group 4: 10 mice received a PBS (ip, 200 µg/mouse).

One hour after in injections, colitis was induced by intracolonic instillation of 2,4,6-trinitrobenzen-sulfonic acid (TNBS) (2 mg/mouse in 40% ethanol of TNBS) in male Balb/C mice (5 to 6 weeks-old). In groups 1, 2 and 3, another injection of either 28G7 or non TLR3-relevant antibody or the anti-TNF antibody was repeated 72 hours after the first antibody injection.

For all groups, several parameters of disease progression were assessed daily: body weight, presence of blood in the feces, presence and severity of diarrhea. All animals were sacrificed for tissue collection 7-days after the induction of colitis. Macroscopic damage score, wall thickness and myeloperoxydase activity (index of granulocyte infiltration), were measured in colonic tissues. Macroscopic damage score is evaluated by observing fecal blood, diarrhea, haemorrhage, adhesion, mucus, erythema, edema, ulcer and stricture.

Figure 4A:
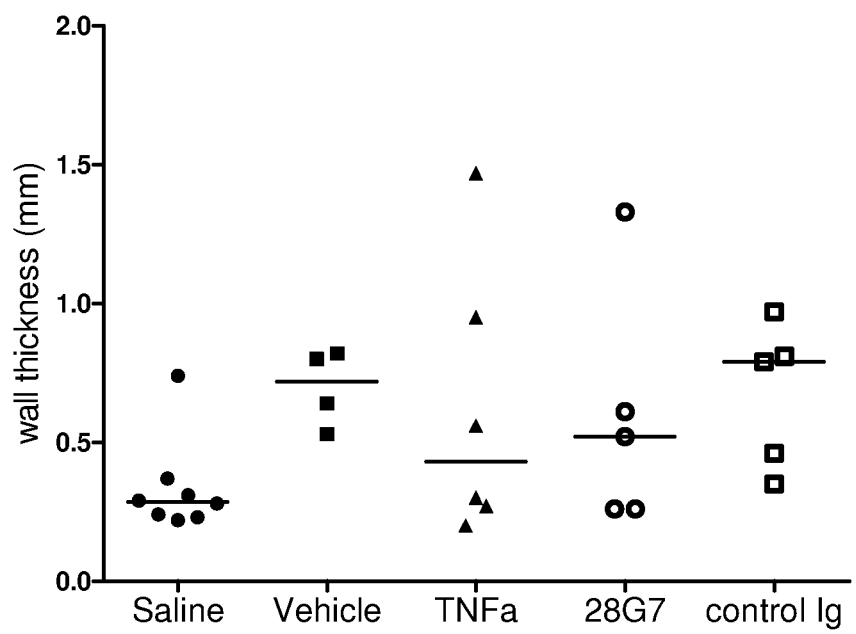
FIG. 4A shows the wall thickness measurements for the mice treated with saline (black dots), with TNBS only (black squares) with an anti-TNFα antibody and TNBS (black triangles), with 28G7 and TNBS (open dots), and with a control Ab and TNBS (open squares).
Figure 4B:
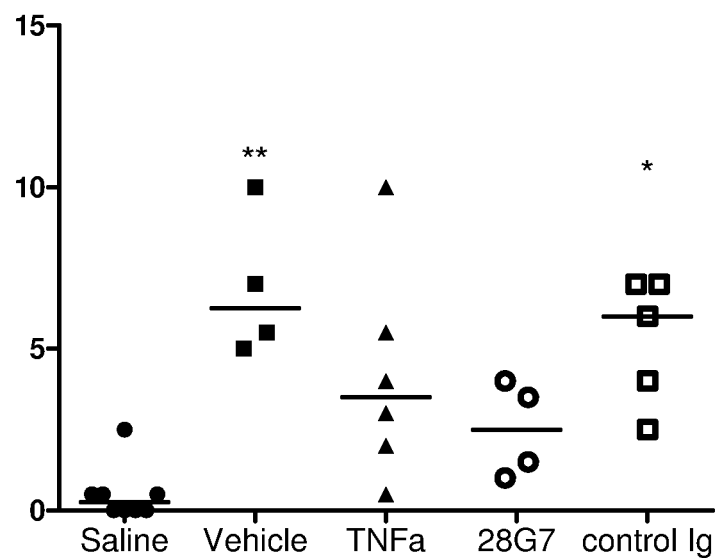
FIG. 4B shows the macroscopic damage score for the mice treated with saline (black dots), with TNBS only (black squares) with an anti-TNFα antibody and TNBS (black triangles), with 28G7 and TNBS (open dots), and with a control Ab and TNBS (open squares). The anti-TLR3 antibody according to the invention ameliorating the development of the disease, under stringent conditions. (*p<0.05, **p<0.01 vs saline).

FIG. 4 shows the results of the experiment. FIG. 4A shows the wall thickness measurements for the mice treated with saline (black dots), with TNBS only (black squares) with an anti-TNFα antibody and TNBS (black triangles), with 28G7 and TNBS (open dots), and with a control Ab and TNBS (open squares). FIG. 4B shows the macroscopic damage score for the mice treated with saline (black dots), with TNBS only (black squares) with an anti-TNFα antibody and TNBS (black triangles), with 28G7 and TNBS (open dots), and with a control Ab and TNBS (open squares).

Example 11

In Vivo Efficacy Model for the Treatment of COPD (Chronic Obstructive Pulmonary Disease)

A. Single Agent Study
Three groups of 10 male mice were treated as follows:
1 group of 10 mice with a vehicle.
1 group of 10 mice with the anti-mouse TLR3 28G7 antibody administration (i.p., 500 µg/per mouse) on days 0, 3, 7, 10, 14, 17, 21 and 24.
1 group of 10 mice with the positive control roflumilast (approved as Daxas™; antagonist of PDE-4) (oral, 15 mg/kg, five times per week).

All mice were treated at days 0, 7, 14 and 21 with Elastin and LPS (i.n.), to induce COPD. At day 28 mice were sacrificed for analysis.

The cellular infiltrates into airways was measured by analysis of bronchoalveolar lavage (BAL) fluid by differential cell count on day 28. The oxygenation of venous blood was measured by gasometry on day 28. The level inflammatory mediators in BALF, through the analysis for protein levels of TNF-alpha, IL-6, IL-17A and IP-10 was performed by multiplex assay. Results are shown in FIG. 5. The figures show that the anti-TLR3 antibodies were highly effective in treating COPD, including in decreasing neutrophil airway infiltration, venous blood oxygen saturation and pro-inflammatory cytokines. Statistical analysis was performed on all data utilizing a Student's t test: '*' $p<0.05$; '' $p<0.005$; '*' $p<0.0005$.

Figure 5A:
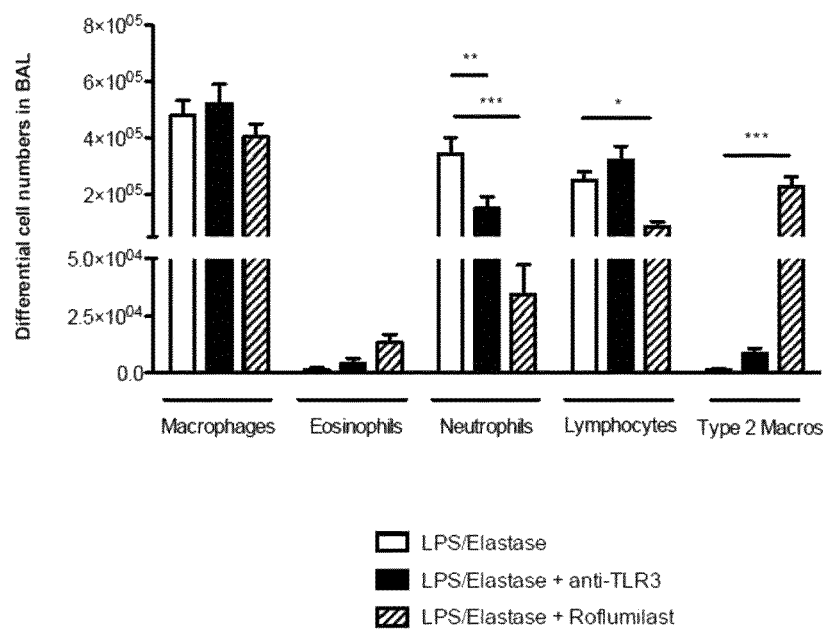
FIG. 5A shows BAL differential cell counts for macrophages, eosinophils, neutrophils and lymphocytes. The anti-TLR3 antibodies strongly decreased the infiltration of neutrophils into the airways, while not substantially affecting macrophages eosinophils or lymphocytes.

FIG. 5A shows BAL differential cell counts for macrophages, eosinophils, neutrophils and lymphocytes. The anti-TLR3 antibodies strongly decreased the infiltration of neutrophils into the airways, while not substantially affecting macrophages eosinophils or lymphocytes. COPD is primarily mediated by neutrophils rather than macrophages or eosinophils (nor lymphocytes, used here as a control).

Figure 5B:
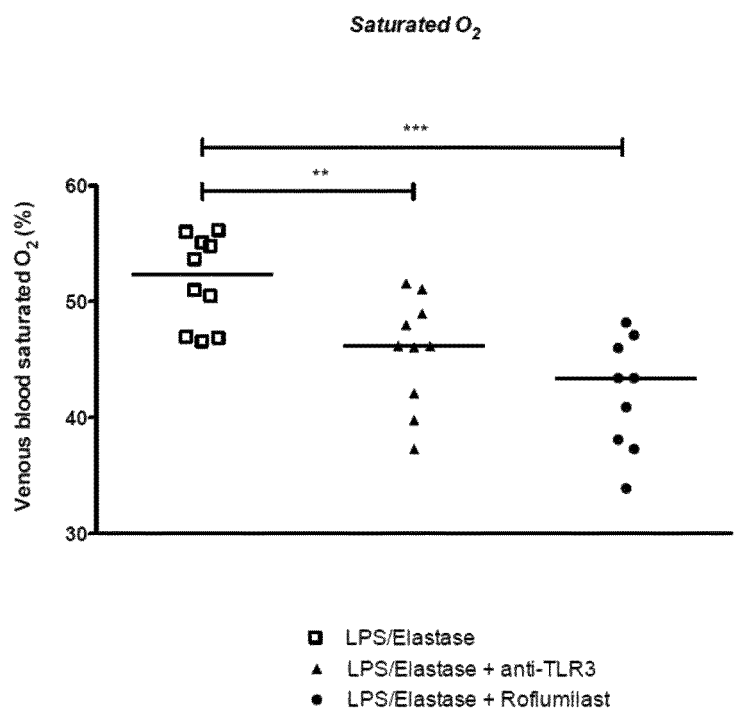
FIG. 5B shows venous blood saturated oxygen (in percent) for each of LPS/elastase alone and LPS/elastase in combination with anti-TLR3 antibodies or roflumilast.

FIG. 5B shows venous blood saturated oxygen (in percent) for each of LPS/elastase alone and LPS/elastase in combination with anti-TLR3 antibodies or roflumilast. The percent saturation of oxygen in arterial blood is diminished in COPD patients compared to healthy individuals, while the venous blood saturation in oxygen is increased in COPD patients compared to healthy individuals. A decrease in percent of $O_2$ in venous blood is therefore an important indicator of a favourable response in disease treatment (see O'Connor et al. Respiration 2011; 81:18-25). It can be seen that anti-TLR3 antibodies decreased percent of $O_2$ in venous blood substantially, almost as much as roflumilast. Anti-TLR3 antibodies are therefore effective in treating COPD. In medical practice, arterial blood gas (ABG) analysis is used both in the acute setting and for assessing patients' gas exchange status during periods of clinical stability. Blood gas analysis, including ABG analysis can therefore be a particularly useful tool to assess whether patients are suitable for treatment with anti-TLR3 antibodies and to assess or monitor whether treatment with anti-TLR3 antibodies is effective, during an acute phase or a phase of clinical stability.

Figure 5C:
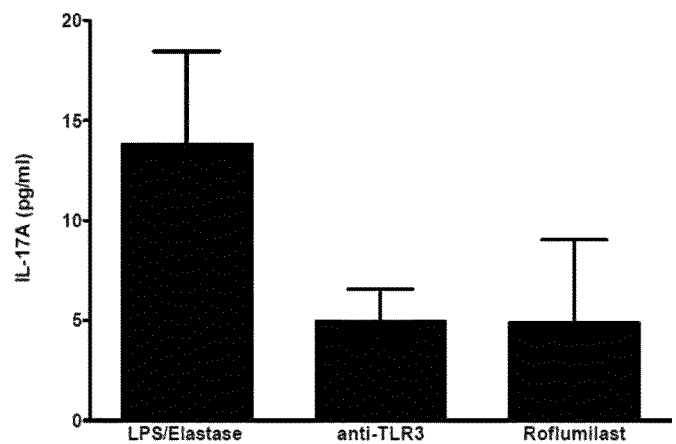
FIG. 5C shows IL17A in BAL fluid (BALF), where anti-TLR3 antibodies decreased IL17A (pg/ml) substantially, and as much as roflumilast.
Figure 5D:
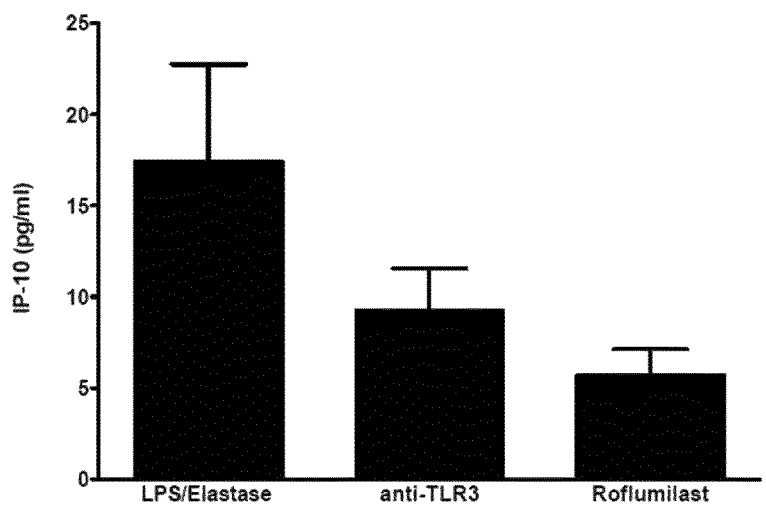
FIG. 5D shows IP-10 in BALF, where -TLR3 antibodies decreased IP-10 (pg/ml) substantially.

FIG. 5C shows IL17A in BAL fluid (BALF). Anti-TLR3 antibodies decreased IL17A (pg/ml) substantially, and as much as roflumilast. FIG. 5D shows IP-10 in BALF. Anti-TLR3 antibodies decreased IP-10 (pg/ml) substantially.

B. Drug Combination Study

Four groups of mice were treated as follows:
1 group of mice with a vehicle (PBS, i.p., twice per week).
1 group of mice with the anti-mouse TLR3 28G7 antibody administration (i.p., 500 µg/per mouse, twice per week).
1 group of mice with the positive control roflumilast (approved as Daxas™; antagonist of PDE-4) (3 mg/kg, oral, five times per week).
1 group of mice with both roflumilast and 28G7 antibody, each agent according to the schedule used as single agent.

All mice were treated with Elastin and LPS (i.n.), to induce COPD and sacrificed as in study A.

The cellular infiltrates into airways was measured by analysis of bronchoalveolar lavage (BAL) fluid by differential cell count as in Study A.

Figure 5E:
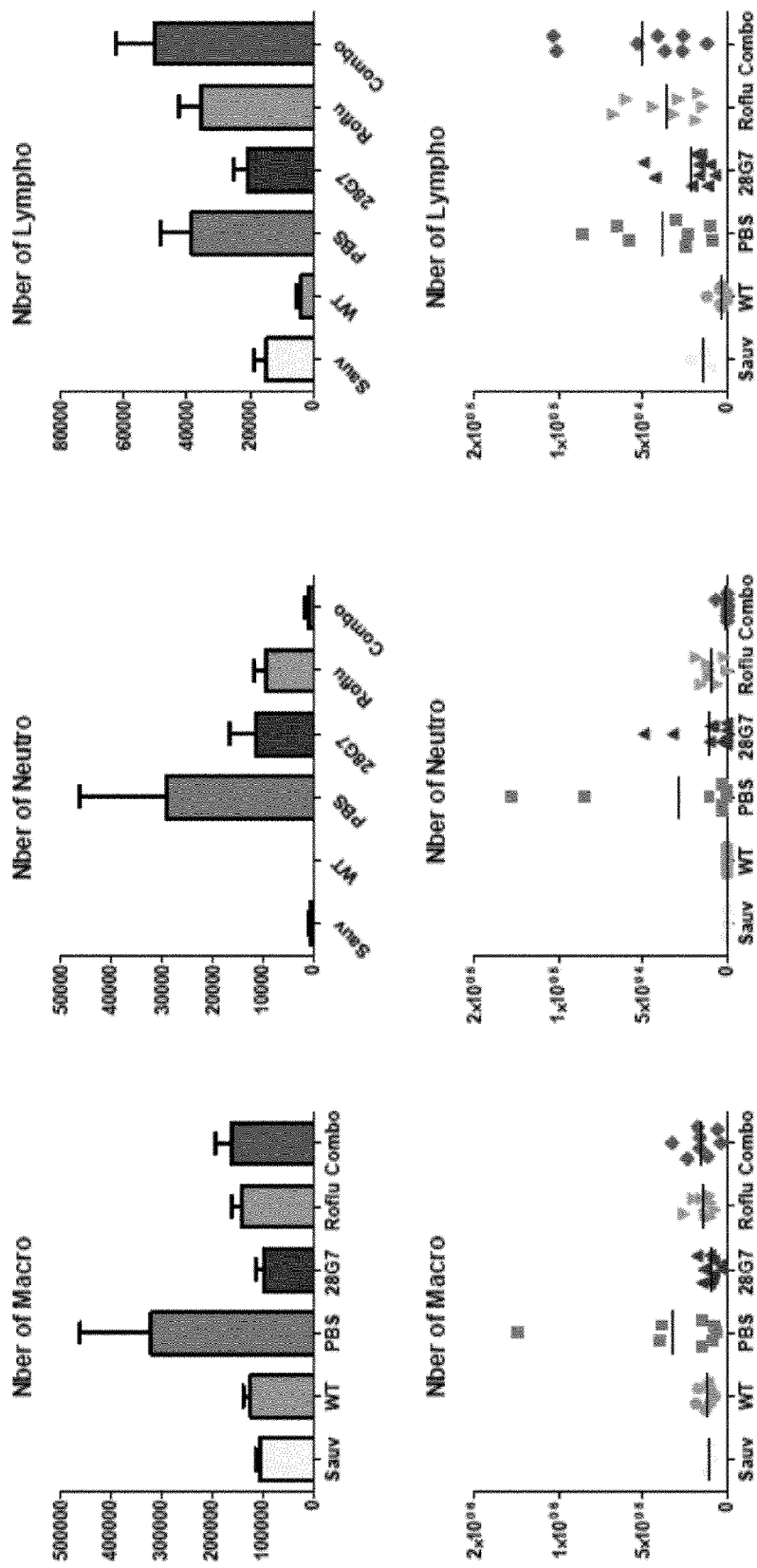
FIG. 5E shows BAL differential cell counts for macrophages, neutrophils and lymphocytes for a second study comparing anti-TLR3 antibodies (28G7), roflumilast (Rofu) and the combination of roflumilast and anti-TLR3 antibodies (combo).

FIG. 5E shows BAL differential cell counts for macrophages, neutrophils and lymphocytes. The anti-TLR3 antibodies strongly decreased the infiltration of neutrophils into the airways, with decreases in macrophages and lymphocytes also observed. COPD is primarily mediated by neutrophils rather than macrophages or eosinophils (nor lymphocytes, used here as a control). Roflumilast also caused decreased infiltration of neutrophils into the airways, together with decreases in macrophages. Interestingly, the combination of anti-TLR3 antibodies and roflumilast caused decreased infiltration of neutrophils into the airways substantially to the level seen in wild-type mice, a decrease far beyond that observed with either agent alone.

Example 12

In Vivo Efficacy Model for the Treatment of Sepsis—Cæcal Ligature and Puncture (CLP)—Curative Setting Briefly 30 mice were operated: the surgery consists in cæcal ligature and puncture. By this way the content of the cæcal lumen is draining of in the abdominal cavity leading to peritonitis and consequently a septic shock. The CLP is mid-grade, e.g. ligature is performed approximately in the middle of the cecum.

Mice were treated with 28G7 (100 µg/mouse, ip), a control antibody with no TLR3 specificity ("control", 100 µg/mouse, ip) or the PBS (300 µl/mouse, ip) 6 hours and 24 hours after operation. Survival was assessed at hours 24, 28, 32, 48, 52, 56, 72, 76, 80, 96, 100, 104, 120, 124, 128, 144, 148, 152, 168, 172, 176, 192, 196, 200, 216, 220, 224, 240, 244, 248, 264, 270, 274, 288, 292, 296, 312, 316, 320 and 336. After 336 hours, the mice which have survived have cleared the acute phase infection. The experiment was stopped and mice were sacrificed.

Figure 6:
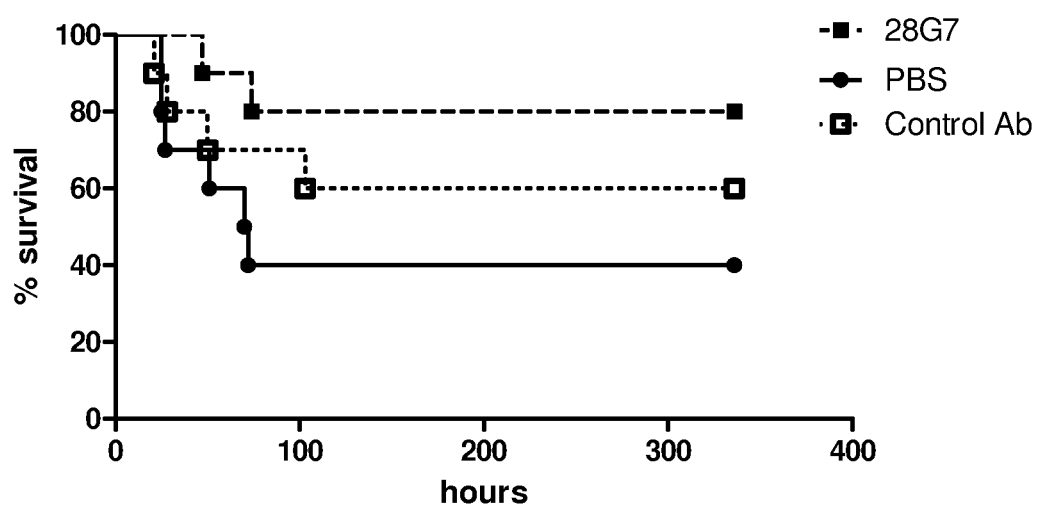
FIG. 6 shows results of a CLP (cecal ligation and puncture—sepsis) mouse model. In this acute model, mice experience an acute infection, mimicking septic shock.

FIG. 6 shows the results of the experiment. The 28G7 treated group has a 80% survival whereas the non-treated group experiences a 40% survival. These results demonstrate that TLR3 antibodies are efficient for the treatment of mice in a CLP mouse model. In this acute model, mice experience an acute infection, mimicking septic shock. The mice which survive have efficiently cleared the acute infection. Therefore, the anti-TLR3 antibodies are suitable agents to treat a patient experiencing a severe acute infection such as a SIRS, a sepsis, a severe sepsis or a septic shock.

Example 13

In Vitro Ip-10 Production by Donor PBMCS in Response to DSRNA and Drug Combinations IP-10 production was assessed in human donors in response to pIC. Fresh PBMC were isolated from whole blood of donors and incubated in the presence of 0, 10 or 50 µg/ml anti-human TLR3 mAbs and a dose range of dexamethasone (0.2, 2 and 20 µg/ml) or Humira® (1, 0.1, 0.01 µg/ml). Cells were incubated 30 minutes at 37° C. prior addition of 30 µg/ml poly(I:C). Cells were incubated for 24 additional hours at 37° C. Supernatant were then harvested to quantify IP10 production by ELISA.

Figures 7A, 7B:
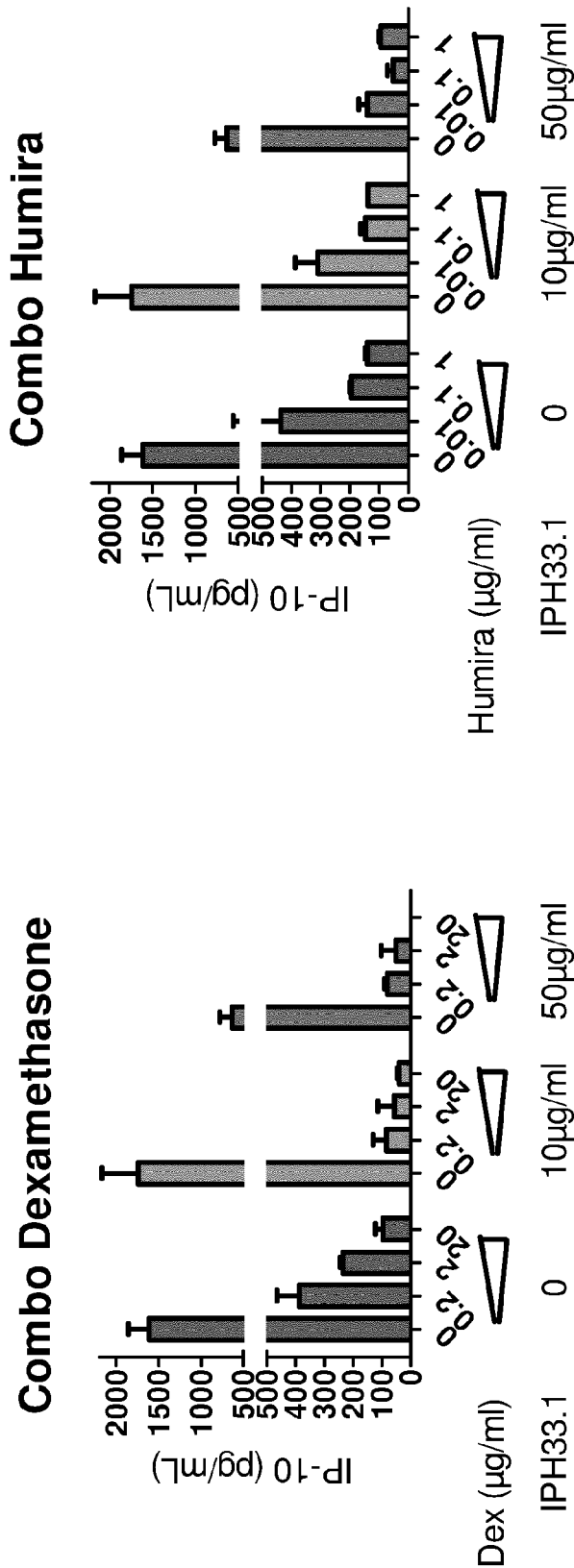
FIGS. 7A and 7B show results of drug combinations with anti-human TLR3 mAbs (labeled IPH33.1) in combination with dexamethasone or Humira® respectively. Antibodies each substantially reduce in vitro IP-10 production by PBMC in response to polyIC further when combined with dexamethasone or Humira®.

Results of drug combinations with anti-human TLR3 mAbs in combination with dexamethasone or Humira® are shown in FIGS. 7A and 7B respectively. Antibodies each substantially reduce IP-10 production in response to polyIC and that the antibodies reduce IP-10 further when combined with dexamethasone or Humira®. Anti-TLR3 antibodies can therefore provide an additional effect when used in combination with dexamethasone or Humira. In particular, in response to polyIC the antibodies potentiate the effects of dexamethasone, the treatment of reference in rheumatoid arthritis. Furthermore, the anti-TLR3 antibodies appeared to potentiate the effects Humira at 0.1 and 1 µg/ml concentrations. The anti-TLR3 antibodies can operate by modulating a signaling pathway that is complementary to those modulated by dexamethasone or Humira®, without antagonistic effects, and can therefore be used advantageously in combination with such drugs.

All headings and sub-headings are used herein for convenience only and should not be construed as limiting the invention in any way. Any combination of the above-described elements in all possible variations thereof is encompassed by the invention unless otherwise indicated herein or otherwise clearly contradicted by context. Recitation of ranges of values herein are merely intended to serve as a shorthand method of referring individually to each separate value falling within the range, unless otherwise indicated herein, and each separate value is incorporated into the specification as if it were individually recited herein.

Unless otherwise stated, all exact values provided herein are representative of corresponding approximate values (e. g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as reference to an element or elements is intended to provide support for a similar aspect or embodiment of the invention that "consists of", "consists essentially of" or "substantially comprises" that particular element or elements, unless otherwise stated or clearly contradicted by context (e. g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

All publications and patent applications cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The invention claimed is:

1. A monoclonal antibody that inhibits Toll-like receptor 3 (TLR3)-mediated signaling in a TLR3-expressing cell, wherein the antibody binds to the glycan-free lateral surface of the N-terminal portion of the TLR3 polypeptide, wherein said antibody has reduced binding to a mutant TLR3 polypeptide comprising a mutation at residue 64, 65, 86, 89, 112, 113, 115, 117, 120, 137 and/or 139 of the TLR3 polypeptide of SEQ ID NO: 1, relative to binding between the antibody and a wild-type TLR3 polypeptide of SEQ ID NO: 1.

2. The antibody of claim 1, wherein the antibody has reduced binding to a TLR3 polypeptide having a mutation at residue 117 and 120 of the TLR3 polypeptide of SEQ ID NO: 1, relative to binding between the antibody and a wild-type TLR3 polypeptide of SEQ ID NO: 1.

3. The antibody of claim 2, wherein the antibody binds said TLR3 polypeptide on the backbone of the TLR3 polypeptide.

4. The antibody of claim 2, wherein the antibody has reduced binding to a TLR3 polypeptide having a mutation at residue 112, 113 and 115 of the TLR3 polypeptide of SEQ ID NO: 1, relative to binding between the antibody and a wild-type TLR3 polypeptide of SEQ ID NO: 1.

5. The antibody of claim 1, wherein the antibody competes with double-stranded ribonucleic acid (dsRNA) for binding to the N-terminal portion of a human TLR3 polypeptide.

6. The antibody of claim 1, wherein the antibody does not substantially bind the glycan-containing lateral surface of the N-terminal portion of the TLR3 polypeptide.

7. The antibody of claim 1, wherein the antibody does not have a significant reduction in binding to a TLR3 polypeptide having a mutation at residues D116 and/or K145 of the TLR3 polypeptide of SEQ ID NO: 1, relative to binding between the antibody and a wild-type TLR3 polypeptide of SEQ ID NO: 1.

8. The monoclonal antibody of claim 1, wherein the antibody comprises:
   (i) a heavy chain comprising CDR 1, 2, and 3 (HCDR1, HCDR2, HCDR3) amino acid sequences as shown in SEQ ID NO: 5, 8, and 10, respectively; and/or a light chain comprising CDR 1, 2 and 3 (LCDR1, LCDR2, LCDR3) amino acid sequences as shown in SEQ ID NO: 11, 12, and 13, respectively;
   (ii) a heavy chain comprising CDR 1, 2 and 3 (HCDR1, HCDR2, HCDR3) amino acid sequences as shown in SEQ ID NO: 16, 19, and 21, respectively; and/or a light chain comprising CDR 1, 2 and 3 (LCDR1, LCDR2, LCDR3) amino acid sequences as shown in SEQ ID NO: 22, 23, and 24, respectively;
   (iii) a heavy chain comprising CDR 1, 2 and 3 (HCDR1, HCDR2, HCDR3) amino acid sequences as shown in SEQ ID NO: 27, 30, and 32, respectively; and/or a light chain comprising CDR 1, 2 and 3 (LCDR1, LCDR2, LCDR3) amino acid sequences as shown in SEQ ID NO: 33, 34, and 35, respectively;
   (iv) a heavy chain comprising CDR 1, 2 and 3 HCDR1, HCDR2, HCDR3) amino acid sequences as shown in SEQ ID NO: 38, 41, and 43, respectively; and/or a light chain comprising CDR 1, 2 and 3 (LCDR1, LCDR2, LCDR3) amino acid sequences as shown in SEQ ID NO: 44, 45, and 46, respectively; or
   (v) a heavy chain comprising CDR 1, 2 and 3 (HCDR1, HCDR2, HCDR3) amino acid sequences as shown in SEQ ID NO: 49, 52, and 54, respectively; and/or a light chain comprising CDR 1, 2 and 3 (LCDR1, LCDR2, LCDR3) amino acid sequences as shown in SEQ ID NO: 55, 56, and 57, respectively.

9. The antibody of claim 8, wherein the antibody competes for binding to a human TLR3 polypeptide with antibody 11E1, 31F6, 32C4, 37B7 or 7G11.

10. The antibody of claim 8, wherein the antibody comprises:
   (i) a heavy chain comprising a heavy chain variable region of SEQ ID NO: 3; and/or a light chain variable region SEQ ID NO: 4;
   (ii) a heavy chain comprising a heavy chain variable region of SEQ ID NO: 14; and/or a light chain variable region SEQ ID NO: 15;
   (iii) a heavy chain comprising a heavy chain variable region of SEQ ID NO: 25; and/or a light chain variable region SEQ ID NO: 26;
   (iv) a heavy chain comprising a heavy chain variable region of SEQ ID NO: 36; and/or a light chain variable region SEQ ID NO: 37; or
   (v) a heavy chain comprising a heavy chain variable region of SEQ ID NO: 47; and/or a light chain variable region SEQ ID NO: 48.

11. A method for inhibiting Toll-like receptor 3 (TLR3)-mediated signaling in a TLR3-expressing cell, the method comprising contacting the TLR3-expressing cell with a monoclonal antibody of claim 8.

12. The method of claim 11, wherein the TLR3-expressing cell is in a subject in vivo, and wherein contacting the TLR3-expressing cell with the antibody comprises administering the antibody to the subject.

13. The antibody of claim 1, wherein said antibody comprises a heavy chain constant region that does not substantially bind a human FcγRIIIa polypeptide.

14. The antibody of claim 13, wherein said antibody comprises an IgG4 heavy chain comprising a serine to proline mutation at residue 228 according to the EU-index.

15. The antibody of claim 1, wherein said antibody is a chimeric, human or humanized antibody.

16. The antibody of claim 1, wherein said antibody is an antibody fragment selected from Fab, Fab', Fab'-SH, F (ab') 2, Fv, diabodies, single-chain antibody fragment, or a multispecific antibody comprising multiple different antibody fragments.

17. The antibody of claim 1, wherein said antibody is capable of being internalized by a TLR3-expressing cell.

18. The antibody of claim 17, wherein said antibody is conjugated or covalently bound to a toxic moiety.

19. A pharmaceutical composition comprising an antibody of claim 1, and a pharmaceutically acceptable carrier.

20. The composition of claim 19, wherein the antibody is present in an amount of between about 25 mg and 500 mg.

21. An article of manufacture comprising:
   (a) a container comprising an anti-Toll-like receptor 3 (TLR3) antibody of claim 1; and
   (b) a package insert with instructions for treating an autoimmune or an inflammatory disease in a patient, wherein the instructions indicate that a dose of the anti-TLR3 antibody of between about 0.05 and 20 mg/kg is administered to the patient at a frequency of from about once per week to about once every 2 months.

22. A hybridoma or recombinant host cell producing the antibody of claim 1.

23. A method of treating an individual having an autoimmune or an inflammatory disease, the method comprising administering to the individual having an autoimmune or an inflammatory disease an effective amount of an antibody of claim 1, wherein said autoimmune or inflammatory disease is responsive to treatment with an inhibitor of TLR3-mediated signaling.

24. The method of claim 23, wherein the effective amount is between about 0.05 and 20 mg/kg, administered to the individual at a frequency of from about once per week to about once every 2 months.

25. The antibody of claim 1, wherein the antibody has reduced binding to a TLR3 polypeptide having a mutation at residue 64 and 65 of the TLR3 polypeptide of SEQ ID NO: 1, relative to binding between the antibody and a wild-type TLR3 polypeptide of SEQ ID NO: 1.

26. The antibody of claim 25, wherein the antibody competes with dsRNA for binding to the N-terminal portion of a human TLR3 polypeptide.

27. A method for inhibiting Toll-like receptor 3 (TLR3)-mediated signaling in a TLR3-expressing cell, the method comprising contacting the TLR3-expressing cell with an antibody of claim 1.

28. The method of claim 27, wherein the TLR3-expressing cell is in a subject in vivo, and wherein contacting the TLR3-expressing cell with the antibody comprises administering the antibody to the subject.

* * * * *